(12) United States Patent
Bock et al.

(10) Patent No.: US 9,339,501 B2
(45) Date of Patent: May 17, 2016

(54) 17A-HYDROXYLASE/C17,20-LYASE INHIBITORS

(71) Applicants: Mark Gary Bock, Boston, MA (US); Christoph Gaul, Aesch (CH); Venkateshwar Rao Gummadi, Bangalore (IN); Saumitra Sengupta, Kolkata (IN)

(72) Inventors: Mark Gary Bock, Boston, MA (US); Christoph Gaul, Aesch (CH); Venkateshwar Rao Gummadi, Bangalore (IN); Saumitra Sengupta, Kolkata (IN)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/682,504

(22) Filed: Apr. 9, 2015

(65) Prior Publication Data

US 2015/0209356 A1    Jul. 30, 2015

Related U.S. Application Data

(62) Division of application No. 14/113,718, filed as application No. PCT/US2012/035583 on Apr. 27, 2012, now Pat. No. 9,029,399.

(30) Foreign Application Priority Data

Apr. 28, 2011  (IN) ............................ 1256/DEL/2011

(51) Int. Cl.

| C07D 401/04 | (2006.01) |
|---|---|
| C07D 401/14 | (2006.01) |
| C07D 409/14 | (2006.01) |
| A61K 31/506 | (2006.01) |
| C07D 405/14 | (2006.01) |
| A61K 31/4439 | (2006.01) |
| A61K 31/444 | (2006.01) |
| A61K 45/06 | (2006.01) |

(52) U.S. Cl.
CPC ............. *A61K 31/506* (2013.01); *A61K 31/444* (2013.01); *A61K 31/4439* (2013.01); *A61K 45/06* (2013.01); *C07D 401/04* (2013.01); *C07D 401/14* (2013.01); *C07D 405/14* (2013.01); *C07D 409/14* (2013.01)

(58) Field of Classification Search
CPC ... C07D 401/04; C07D 401/14; C07D 409/14
See application file for complete search history.

(56) References Cited

U.S. PATENT DOCUMENTS

| 3,832,352 | A | 8/1974 | Ilvespaa |
|---|---|---|---|
| 5,145,845 | A | 9/1992 | Johnson et al. |
| 5,519,036 | A | 5/1996 | Himmelsbach et al. |
| 5,789,425 | A | 8/1998 | Takano et al. |
| 7,405,233 | B2 | 7/2008 | Wilde et al. |
| RE45,173 | E | 9/2014 | Bock et al. |
| 8,946,260 | B2 | 2/2015 | Bock et al. |
| 2005/0154028 | A1 | 7/2005 | Bromidge et al. |
| 2006/0167065 | A1 | 7/2006 | Wilde et al. |
| 2009/0264650 | A1 | 10/2009 | Cho et al. |
| 2010/0222588 | A1 | 9/2010 | Peterson et al. |
| 2011/0039893 | A1 | 2/2011 | Kori et al. |
| 2014/0228386 | A1 | 8/2014 | Bock et al. |

FOREIGN PATENT DOCUMENTS

| EP | 0719773 B1 | 11/2001 |
|---|---|---|
| JP | 8-176111 A1 | 7/1996 |
| WO | 97/08150 A1 | 3/1997 |
| WO | 01/54694 A1 | 8/2001 |
| WO | 02/20493 A2 | 3/2002 |
| WO | 03/027085 A2 | 4/2003 |
| WO | 03/027096 A1 | 4/2003 |
| WO | 03/027101 A1 | 4/2003 |
| WO | 03/027105 A1 | 4/2003 |
| WO | 03/027107 A1 | 4/2003 |
| WO | 03/057220 A1 | 7/2003 |
| WO | 2004/009558 A2 | 1/2004 |
| WO | 2006/078698 A1 | 7/2006 |
| WO | 2007/109330 A2 | 9/2007 |
| WO | 2008/094556 A2 | 8/2008 |
| WO | 2009/078992 A1 | 6/2009 |
| WO | 2009/097567 A1 | 8/2009 |
| WO | 2009/143039 A2 | 11/2009 |
| WO | 2009/156484 A2 | 12/2009 |

(Continued)

OTHER PUBLICATIONS

Abad, A. et al., "Regioselective Preparation of Pyridin-2-yl Ureas from 2-Chloropyridines Catalyzed by Pd(0)", Synthesis, 2005, No. 6, pp. 0915-0924.

(Continued)

*Primary Examiner* — Brian McDowell

(74) *Attorney, Agent, or Firm* — Qian Zhang

(57) ABSTRACT

The present invention provides compounds of Formula (I), or a pharmaceutically acceptable salt thereof,

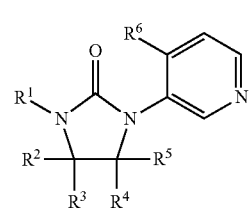

(I)

where $R^1$, $R^2$, $R^3$, $R^4$, $R^5$ and $R^6$ are as defined herein. The compounds of the present invention have been found to be useful as 17α-hydroxylase/$C_{17,20}$-lyase inhibitors.

2 Claims, No Drawings

(56) References Cited

FOREIGN PATENT DOCUMENTS

| WO | 2009/158473 | A1 | 12/2009 |
|---|---|---|---|
| WO | 2010/045303 | A2 | 4/2010 |
| WO | 2010/149755 | A1 | 12/2010 |
| WO | 2011/017534 | A2 | 2/2011 |
| WO | 2011/059969 | A2 | 5/2011 |
| WO | 2011/088160 | A2 | 7/2011 |
| WO | 2011/098776 | A1 | 8/2011 |

OTHER PUBLICATIONS

Anjaneyulu, B. et al., Nitroimidazoles: Part XXII-Synthesis of potential metabolites of satranidazole by non-nitroreductive and nitroreductive routes, Indian J. of Chem., 1991, vol. 30B, pp. 399-406.

Arya, V. P. et al., "Nitroimidazoles: Part XVI-Some 1-Methyl-3-nitro-5-substituted Imidazoles", Indian J. of Chem, 1982, vol. 21B, pp. 1115-1117.

Babczinski, P. et al., "Substituted Tetrahydropyrimidones: A New Herbicidal Class of Compounds Including Chlorosis by Inhibition of Phytoene Desaturation", Pesticide Biochem. and Physiology, 1995, 52, pp. 45-59.

El-Metwally, S. et al., "Reactions of 1,3-Diphenyl-2-pyrazolin-5-one and 4-Amino-1,5-dimethyl-2-phenyl-1H-pyrazol-3(2H)-one. Synthesis of Some New Pyrazoles and Pyrazolones", Acta Chim. Slov., 2010, vol. 57, No. 4, pp. 941-947.

Ghandi, M. et al., "Synthesis of New Unsymmetrical 4,5-Dihydroxy-2imidazolidinones", Molecules, 2006, 11, pp. 768-775.

Goodacre, C. J. et al., "A series of bisaryl imidazolidin-2-ones has shown to be selective and orally active 5-HT2c receptor antagonists", Bioorg. Med. Chem. Lett. 2005, 15, pp. 4989-4993.

Hafner et al., "Synthesis of Symmetrically and Unsymmetrically Substituted N, Nc-Diarylimidazolin-2-ones by Copper-Catalyzed Arylamidation under Microwave-Assisted and Conventional Conditions", Synthesis, 2007, No. 9, pp. 1403-1411.

Johnson et al., "A New Synthesis of 2-Chloroalkyl Isocyanates", J. Org. Chem., 1967, vol. 32, pp. 1508-1510.

King, F. D. (Ed.), "Bioisosteres, conformational restriction and pro-drugs-case-history: an example of a conformational restriction approach", Medical Chemistry: Principles and Practice, 1994, Chapter 14, pp. 206-209.

Leroux, F., "Inhibition of P450 17 as a new strategy for the treatment of prostate cancer", Current Medicinal Chemistry, Bentham Science Publishers BV, BE, vol. 12, No. 14, Jan. 1, 2005, pp. 1623-1629.

Meth-Cohn O, Yan Z., Linear and macrocyclid ligands containing alternating pyridine and imidazolidin-2-one units. 1998, J. Chem. Soc. Perkin Trans 1, pp. 423-436.

Nagarajan, K. et al., "Nitroimidazoles: Part XIX-Structure-activity Relationships", Indian J. of Chem., 1984, vol. 23B, pp. 342-362.

Nagarajan, K. et al., "Nitroimidazoles, Part XXIII*-Activity of satranidazole series against anerobic infections", Indian J. of Experimental Bio., 1992, vol. 30, pp. 193-200.

Njar, V. C. et al., "Inhibitors of 17alpha-hydroxylase/17,20-lyase (CYP17): potential agents for the treatment of prostate cancer", Curr Pharm Des., Mar. 1999, 5(3), pp. 163-180. Abstract Only.

Saczewski, F., "2-Chloro-4,5-dihydroimidazole", Synthesis, 1984, pp. 170-172.

Saczewski, F., "2-Chloro-4,5-dihydroimidazole, Part X[1]", J. Heterocyclic Chem., 2002, vol. 39, pp. 911-915.

Shia et al., "Design, Synthesis, and Structure-Activity Relationship of Pyridyl Imidazolidinones: A Novel Class of Potent and Selective Human Enterovirus 71 Inhibitors", J. Med. Chem., 2002, vol. 45, pp. 1644-1655.

17A-HYDROXYLASE/C17,20-LYASE INHIBITORS

This application is a divisional of U.S. application Ser. No. 14/113,718, filed Apr. 25, 2014, which is a US National Phase 371 Application of International Application Number PCT/US2012/035583, filed Apr. 27, 2012, which claims benefit of Indian Provisional Application Number 1256/DEL/2011 filed Apr. 28, 2011, the content of which is incorporated herein by reference in its entirety.

FIELD OF THE INVENTION

The present invention relates to cyclic urea derivatives and their use for the treatment of various disease conditions mediated by the regulation of 17α-hydroxylase/$C_{17,20}$-lyase.

BACKGROUND

The number of people diagnosed with cancer world wide has significantly increased and continues to rise at an alarming rate. Cancer is characterized by an increase in the number of abnormal cells derived from a given normal tissue, invasion of adjacent tissues by these abnormal cells, or lymphatic or blood-borne spread of malignant cells to regional lymph nodes and to distant sites (i.e., metastasis).

Of special interest are individuals diagnosed with androgen-dependent disorders, such as prostate cancer, estrogen-dependent disorders (such as breast, uterine, and ovarian cancer), Cushing's syndrome, polycyctic ovary syndrome (PCOS), and aldo-producing adenoma (APA).

Prostate cancer is currently the most common non-skin cancer and the second leading cause of cancer-related death in men after lung cancer. The primary course of treatment for patients diagnosed with organ-confined prostate cancer is usually prostatectomy or radiotherapy. These treatments for prostate and breast cancer are highly invasive and characterized by undesirable and serious side effects. Furthermore, a large percent of individuals who receive localized treatments such as surgery or radiotherapy may suffer from recurring cancer and widespread metastases. As with surgery and radiation therapies, there are several drawbacks to chemotherapy, including the fact that almost all chemotherapeutic agents are toxic, and chemotherapy causes significant, and often dangerous, side effects, such as severe nausea, bone marrow depression, and immunosuppression. Additionally, many tumor cells are resistant or become resistant to chemotherapeutic agents through multi-drug resistance.

Treatments such as hormone therapy are another option for individuals diagnosed with hormone-dependent, hormone-responsive, or hormone-sensitive cancers, such as prostate or breast cancer. However, some individuals who have been administered current hormone therapy treatments may not show a significant response to such treatments and some may suffer from relapsing of cancer.

Currently chemo-refractory and hormone-refractory cancer patients are left with very few treatment options and there remains an unmet need for more effective ways to treat cancer such as, but not limited to, prostate cancer and breast cancer.

The demonstration by Huggins and Hodges C. V., (Cancer Res., 1941, 1, 293) and Huggins et al in Arch. Surg., 1941, 43, 209 lead to androgen ablation being considered as a possible approach to treatment. It has been demonstrated that testosterone levels are reduced by orchidectomy or by administration of GnRH analogs (gonadotropic releasing hormones). GnRH analogs can have side effects such as cardiovascular degeneration and osteoporosis, which are the two most potentially serious conditions induced by the continuous presence of GnRH. Moreover these treatment options only eliminate testosterone production from the testes and not that produced by the adrenal.

In the adrenal glands, the biosynthetic cascade also leads to the formation of gluco- and mineralcorticoids.

Since androgen and estrogen are hormones having various physiological activities such as differentiation and proliferation of cells and the like, it was thought that potent and specific compounds that inhibit androgen synthesis in the testes, adrenals, and other tissue may be more effective for the treatment of PCa (Njar, V. C. O.; Brodie, A. M. H., "Inhibitors of 17α-hydroxylase-$C_{17,20}$-lyase (CYP17): Potential agents for the treatment of prostate cancer", Current Pharm. Design, 1999, 5: 163-180).

In order to avoid unwanted side effects, androgen biosynthesis inhibitors have to be specific enough not to influence corticosteroid biosynthesis. A promising novel strategy for the treatment of prostrate cancer is the development of strong and selective inhibitors of CYP17 as this would result in complete and exclusive elimination of androgen biosynthesis as suggested in Current Medicinal Chemistry, 2005, 12, 1623-1629.

Steroid-type compounds and non-steroid-type compounds are already known as steroid $C_{17,20}$-lyase inhibitors. The steroid-type compounds are disclosed in, for example, WO 92/15404, WO 93/20097, EP-A 288053, EP-A 413270 and the like. As non-steroid-type compounds, for example, in WO94/27989, WO96/14090 and WO97/00257 azole derivatives are described in WO95/09157 1H-benzimidazole derivatives are described in U.S. Pat. No. 5,491,161, dihydronaphthalene derivatives are described in WO99/18075, and naphthalene derivatives are shown in WO99/54309.

A variety of potent steroidal and non-steroidal inhibitors of CYP17 have been reported and some have been shown to be potent inhibitors of testosterone production in rodent models (Njar and Brodie, above). Jarman and colleagues have described the hormonal impact of their most potent CYP17 inhibitor, abiraterone in patients with prostate cancer (O'Donnell et al., "Hormonal impact of the 17α-hydroxylase/C17,20-lyase inhibitors abiraterone acetate (CB7630) in patients with prostate cancer", Br. J. Cancer, 2004, 90: 2317-2325). Abiraterone has been discussed in patents such as WO 200900132, WO 2008024485, WO 2006021776, WO 09509178, WO 09320097

Non-steroidal small molecule inhibitors have been described for example in BMC 2004, 12, (4313), YM116, 2-(1H-imidazol-4-ylmethyl)-9H-carbazole, and their effects in decreasing adrenal androgen synthesis by inhibiting C17-20 lyase activity in NCI-H295 human adrenocortical carcinoma cells has been described by Ideyama Y, Kudoh M, Tanimoto K, Susaki Y, Nanya T, Nakahara T, Ishikawa H, Fujikura T, Akaza H, Shikama H in "Jpn. J. Pharmacol., 1999, 79: No. 2(213-20)". Novel non-steroidal inhibitor of cytochrome P450 (17 alpha-hydroxylase/C17-20 lyase), YM116, and its role in decreased prostatic weights by reducing the serum concentrations of testosterone and adrenal androgens in rats has been reported by Ideyama Y, Kudoh M, Tanimoto K, Susaki Y, Nanya T, Nakahara T, Ishikawa H, Yoden T, Okada M, Fujikura T, Shikama H Proc. Am. Assoc. Cancer Res., 1998, 39:89 Meet. (384)

Synthesis and biological evaluation of novel non-steroidal inhibitors of steroid 17,20 lyase has been described by—Yoden T, Okada M, Kawaminami E, Kinoyama I, Ideyama Y, Isomura Y in Abstr. Pap. Am. Chem. Soc., 1997, 213 Meet.: Pt. 2(MEDI206)

Further illustrative of the background of the invention are patent applications such as US20080280864A1 or WO28154382A1.

SUMMARY

The compounds described herein have been shown to be inhibitors of 17α-hydroxylase/C$_{17,20}$-lyase.

One embodiment of the present invention provides compounds of Formula (I)

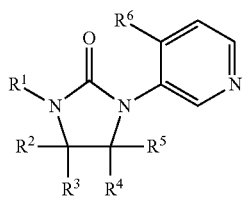

(I)

wherein $R^1$ is (i) phenyl optionally substituted with 1 to 3 substituents selected from halo, —CN, —OH, (C$_1$-C$_6$)alkyl, halo-substituted (C$_1$-C$_6$)alkyl, (C$_1$-C$_6$)alkoxy, —NH$_2$, —NH(C$_1$-C$_4$)alkyl, —N((C$_1$-C$_4$)alkyl)$_2$, —NHC(O)—(C$_1$-C$_4$)alkyl, —C(O)NH$_2$, —C(O)—NH(C$_1$-C$_4$)alkyl, —C(O)—N((C$_1$-C$_4$)alkyl)$_2$, (C$_3$-C$_5$)cycloalkyl, or a 5- to 6-membered heterocycle, (ii) phenyl fused to an additional phenyl, a 5- to 6-membered heteroaryl, a 5- to 6-membered partially or fully saturated cycloalkyl, or a 5- to 6-membered partially or fully saturated heterocycle, where said fused phenyl is optionally substituted with 1 to 4 substituents each independently selected from halo, —CN, (C$_1$-C$_6$)alkyl, (C$_1$-C$_6$)alkoxy, hydroxy-substituted (C$_1$-C$_4$)alkyl, halo-substituted (C$_1$-C$_4$)alkyl, (C$_3$-C$_5$)cycloalkyl, oxo, —NH$_2$, —NH(C$_1$-C$_4$)alkyl, —N((C$_1$-C$_4$)alkyl)$_2$, —NHC(O)—(C$_1$-C$_4$)alkyl, or =N—OH, (iii) 5- to 6-membered heteroaryl optionally substituted with 1 to 3 substituents each independently selected from halo, —CN, —OH, (C$_1$-C$_6$)alkyl, halo-substituted (C$_1$-C$_6$)alkyl, (C$_1$-C$_6$)alkoxy, —NH$_2$, —NH(C$_1$-C$_4$)alkyl, —N((C$_1$-C$_4$)alkyl)$_2$, —NHC(O)—(C$_1$-C$_4$)alkyl, —C(O)NH$_2$, —C(O)—NH(C$_1$-C$_4$)alkyl, —C(O)—N((C$_1$-C$_4$)alkyl)$_2$, (C$_3$-C$_5$)cycloalkyl, or a 5- to 6-membered heterocycle, or (iv) 5- to 6-membered heteroaryl fused to another 5- to 6-membered heteroaryl, phenyl, 5- to 6-membered partially or fully saturated cycloalkyl, or a 5- to 6-membered partially or fully saturated heterocycle, where said fused heteroaryl is optionally substituted with 1 to 4 substituents each independently selected from halo, —CN, (C$_1$-C$_6$)alkyl, (C$_1$-C$_6$)alkoxy, hydroxy-substituted (C$_1$-C$_4$)alkyl, halo-substituted (C$_1$-C$_4$)alkyl, cyclopropyl, oxo, —NH$_2$, —NH(C$_1$-C$_4$)alkyl, —N((C$_1$-C$_4$)alkyl)$_2$, —NHC(O)—(C$_1$-C$_4$)alkyl, or =N—OH;

$R^2$ and $R^5$ are each independently CH$_3$ or H;

$R^3$ and $R^4$ are each independently CH$_3$ or H, or taken together with the carbon atoms to which they are attached form a cyclopropyl; and $R^6$ is (C$_3$-C$_5$)cycloalkyl, where the cycloalkyl is optionally substituted with hydroxy; or a pharmaceutically acceptable salt thereof.

In another embodiment, a compound of Formula (I) is provided wherein $R^1$ is (i) phenyl optionally substituted with 1 to 3 substituents selected from halo, —CN, —OH, (C$_1$-C$_6$)alkyl, halo-substituted (C$_1$-C$_6$)alkyl, (C$_1$-C$_6$)alkoxy, —NH$_2$, —NH(C$_1$-C$_4$)alkyl, —N((C$_1$-C$_4$)alkyl)$_2$, —NHC(O)—(C$_1$-C$_4$)alkyl, —C(O)NH$_2$, —C(O)—NH(C$_1$-C$_4$)alkyl, —C(O)—N((C$_1$-C$_4$)alkyl)$_2$, or a 5- to 6-membered heterocycle, (ii) phenyl fused to an additional phenyl, a 5- to 6-membered heteroaryl, a 5- to 6-membered partially or fully saturated cycloalkyl, or a 5- to 6-membered partially or fully saturated heterocycle, where said fused phenyl is optionally substituted with 1 to 4 substituents each independently selected from halo, —CN, (C$_1$-C$_6$)alkyl, (C$_1$-C$_6$)alkoxy, hydroxy-substituted (C$_1$-C$_4$)alkyl, halo-substituted (C$_1$-C$_4$) alkyl, cyclopropyl, oxo, —NH$_2$, —NH(C$_1$-C$_4$)alkyl, —N((C$_1$-C$_4$)alkyl)$_2$, —NHC(O)—(C$_1$-C$_4$)alkyl, or =N—OH, (iii) 5- to 6-membered heteroaryl optionally substituted with 1 to 3 substituents each independently selected from halo, —CN, —OH, (C$_1$-C$_6$)alkyl, halo-substituted (C$_1$-C$_6$) alkyl, cyclopropyl, (C$_1$-C$_6$)alkoxy, —NH$_2$, —NH(C$_1$-C$_4$) alkyl, —N((C$_1$-C$_4$)alkyl)$_2$, —NHC(O)—(C$_1$-C$_4$)alkyl, —C(O)NH$_2$, —C(O)—NH(C$_1$-C$_4$)alkyl, —C(O)—N((C$_1$-C$_4$)alkyl)$_2$, or a 5- to 6-membered heterocycle, or (iv) 5- to 6-membered heteroaryl fused to another 5- to 6-membered heteroaryl, phenyl, 5- to 6-membered partially or fully saturated cycloalkyl, or a 5- to 6-membered partially or fully saturated heterocycle, where said fused heteroaryl is optionally substituted with 1 to 4 substituents each independently selected from halo, —CN, (C$_1$-C$_6$)alkyl, (C$_1$-C$_6$) alkoxy, hydroxy-substituted (C$_1$-C$_4$)alkyl, halo-substituted (C$_1$-C$_4$)alkyl, cyclopropyl, oxo, —NH$_2$, —NH(C$_1$-C$_4$)alkyl, —N((C$_1$-C$_4$)alkyl)$_2$, —NHC(O)—(C$_1$-C$_4$)alkyl, or =N—OH;

$R^2$ and $R^5$ are each independently CH$_3$ or H;

$R^3$ and $R^4$ are each independently CH$_3$ or H, or taken together with the carbon atoms to which they are attached form a cyclopropyl; and $R^6$ is (C$_3$-C$_5$)cycloalkyl, where the cycloalkyl is optionally substituted with hydroxy; or a pharmaceutically acceptable salt thereof.

In one particular embodiment, $R^2$, $R^3$, $R^4$ and $R^5$ are each independently CH$_3$ or H.

In another particular embodiment, $R^2$, $R^3$, $R^4$ and $R^5$ are each H.

In yet another particular embodiment, $R^2$ and $R^5$ are each H, and $R^3$ and $R^4$ are taken together to form a cyclopropyl ring.

Another embodiment provides compounds of Formula (II)

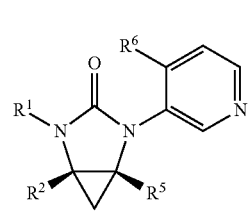

(II)

wherein:

$R^1$ is as defined above for the compound of Formula (I);

$R^2$ and $R^5$ are each independently CH$_3$ or H (alternatively, both $R^2$ and $R^5$ are H); and $R^6$ is $(C_3-C_5)$cycloalkyl, where the cycloalkyl is optionally substituted with hydroxy (e.g., 1-hydroxycyclopropyl, 1-hydroxycyclobutyl, or 1-hydroxycyclopentyl);

or a pharmaceutically acceptable salt thereof.

In yet another embodiment, compounds of Formula (III) are provided

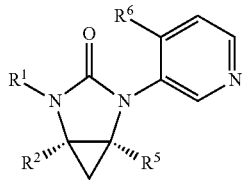

(III)

wherein $R^1$ $R^2$, $R^5$ and $R^6$ are as defined above for the compound of Formula (II); or a pharmaceutically acceptable salt thereof $R^6$ is preferably (for compounds of Formula (I), (II) or (III)) cyclopropyl, where the cyclopropyl is optionally substituted with hydroxy (e.g., 1-hydroxycyclopropyl). In a particular embodiment, $R^6$ is an unsubstituted cyclopropyl.

$R^1$ is preferably (for any of the compounds or embodiments described above) is (i) a phenyl optionally substituted with 1 or 2 substituents each independently selected form fluoro, chloro, cyano, methyl, difluoromethyl, trifluoromethyl, cyclopropyl, methoxy, or —C(O)NHCH₃;

(ii) a fused phenyl selected from naphthalen-2-yl, naphthalen-1-yl, 1H-indol-5-yl, 1H-indol-6-yl, benzothiazol-5-yl, benzothiazol-6-yl, 1,2,3,4-tetrahydro-quinolin-6-yl, benzo[b]thiophen-5-yl, quinolin-6-yl, quinolin-7-yl, indan-5-yl, 1,2-dihydroquinolin-6-yl, 1H-indazol-5-yl, 1H-indazol-6-yl, benzofuran-5-yl, 2,3-dihydrobenzo[1,4]dioxin-6-yl, 2,3-dihydro-benzofuran-5-yl, benzo[1,3]dioxol-5-yl, 1,2,3,4-tetrahydro-quinolin-7-yl, quinoxalin-6-yl, benzooxazol-5-yl, benzo[d]isoxazol-5-yl, benzo[d]isoxazol-6-yl, 1H-benzoimidazol-5-yl, 2,3-dihydro-1H-indazol-5-yl, 2,3-dihydro-1H-indazol-6-yl, indolin-5-yl, or 1H-benzotriazol-5-yl, where said fused phenyl is optionally substituted with 1 to 3 substituents each independently selected from fluoro, chloro, methyl, ethyl, trifluoromethyl, methoxy, oxo, —NH₂, =N—OH or cyclopropyl;

(iii) a 5- to 6-membered heteroaryl selected from thiophen-2-yl, thiophen-3-yl, pyridin-2-yl, pyridin-3-yl, pyridin-4-yl, pyrimidin-2-yl, pyrimidin-4-yl, pyrimidin-5-yl, 1H-pyrazol-4-yl, thiazol-2-yl, or isothiazol-4-yl, where said 5- to 6-membered heteroaryl is optionally substituted with 1 to 3 substituents each independently selected from fluoro, chloro, methyl, ethyl, isopropyl, cyclopropyl, hydroxy, difluoromethyl, trifluoromethyl, methoxy, —NH₂, —NHC(O)CH₃, —C(O)NHCH₃, or pyrrolidin-1-yl; or (iv) a fused heteroaryl selected from benzo[b]thiophen-2-yl, benzo[b]thiophen-3-yl, quinolin-2-yl, quinolin-3-yl, benzooxazol-2-yl, benzothiazol-2-yl, 4,5,6,7-tetrahydro-thieno[2,3-c]pyridin-2-yl, imidazo[1,2-a]pyridin-3-yl, imidazo[1,2-a]pyridin-6-yl, imidazo[1,2-a]pyridin-7-yl, 3H-imidazo[4,5-b]pyridin-6-yl, thieno[3,2-c]pyridin-2-yl, thieno[3,2-c]pyridin-3-yl, or 1H-indol-3-yl, where said fused heteroaryl is optionally substituted with 1 to 4 substituents each independently selected from fluoro, chloro, cyano, methyl, cyclopropyl, or methoxy; or a pharmaceutically acceptable salt thereof.

In another embodiment (for any of the compounds or embodiments described above), $R^1$ is (i) a phenyl optionally substituted with 1 to 2 substituents each independently selected from fluoro, chloro, methyl, methoxy, trifluoromethyl, difluoromethyl, or cyano;

(ii) a fused phenyl selected from naphthalen-2-yl, quinolin-6-yl, 3,4-dihydro-2-oxo-quinolin-6-yl, benzo[b]thiophen-5-yl, benzo[b]thiophen-6-yl, benzo[d]isoxazol-5-yl, 1H-indazol-6-yl, 1H-indazol-5-yl, benzothiazol-6-yl, 1,2-dihydro-3-oxo-indazol-6-yl, indan-5-yl, 1H-benzotriazol-5-yl, benzofuran-5-yl, 2,3-dihydro-benzo[1,4]dioxin-6-yl, 2,3-dihydro-benzofuran-5-yl, or benzo[1,3]dioxol-5-yl where said fused phenyl is optionally substituted with 1 to 2 substituents each independently selected from chloro, fluoro, methyl, ethyl, difluoromethyl, trifluoromethyl, cyclopropyl, cyano, or amino;

(iii) a 5- to 6-membered heteroaryl selected from isothiazol-4-yl, thiophen-2-yl, thiophen-3-yl, pyridin-2-yl, pyridin-4-yl, pyrimidin-4-yl, or pyrimidin-2-yl where said isothiazol-4-yl, said thiophen-2-yl, said thiophen-3-yl, and said pyridin-2-yl, pyridin-4-yl, said pyrimidin-4-yl, and said pyrimidin-2-yl are optionally substituted with fluoro, chloro, methyl, trifluoromethyl, difluoromethyl, cyclopropyl, or methoxy; or (iv) a fused heteroaryl selected from thieno[3,2-c]pyridin-2-yl, thieno[3,2-c]pyridin-3-yl, thieno[3,2-c]pyridin-2-yl, imidazo[1,2-a]pyridin-7-yl, or benzo[b]thiophen-2-yl, where said fused heteroaryl is optionally substituted with 1 to 2 substituents each independently selected from fluoro, chloro, methyl, difluoromethyl, trifluoromethyl, cyclopropyl, or amino; or a pharmaceutically acceptable salt thereof.

In one particular embodiment (for any of the compounds or embodiments described above), $R^1$ is phenyl, 4-chloro-3-fluoro-phenyl, m-tolyl, 3-methoxy-phenyl, 3-chloro-4-fluoro-phenyl, 4-fluoro-3-methyl-phenyl, 3-trifluoromethyl-phenyl, 3-chloro-phenyl, 4-fluoro-3-trifluoromethyl-phenyl, 3-difluoromethyl-4-fluoro-phenyl, 3-cyano-4-fluorophenyl, 3-cyanophenyl, 3-chloro-4-cyanophenyl, 3,4-difluoro-phenyl, 4-trifluoromethyl-phenyl; or a pharmaceutically acceptable salt thereof.

In another particular embodiment (for any of the compounds or embodiments described above), $R^1$ is naphthalen-2-yl, benzo[b]thiophen-5-yl, 3-methylbenzo[b]thiophen-5-yl, 2-fluoro-3-methylbenzo[b]thiophen-5-yl, 3-trifluoromethyl-benzo[b]thiophen-5-yl, 2-fluorobenzo[b]thiophen-5-yl, 2-chlorobenzo[b]thiophen-5-yl, benzo[b]thiophen-6-yl, 2-fluoro-benzo[b]thiophen-6-yl, 3-methylbenzo[b]thiophen-6-yl, 4-fluoro-benzo[b]thiophen-6-yl, 5-fluoro-3-methylbenzo[b]thiophen-6-yl, 3-methyl-benzo[d]isoxazol-5-yl, 1H-indazol-5-yl, 1-methyl-1H-indazol-5-yl, 3-amino-1H-indazol-5-yl, 1H-indazol-6-yl, 3-amino-1H-indazol-6-yl, 3-methyl-1H-indazol-6-yl, 3-trifluoromethyl-1H-indazol-6-yl, benzothiazol-6-yl, 1,2-dihydro-3-oxo-indazol-6-yl, indan-5-yl, 1H-benzotriazol-5-yl, 3-methyl-benzofuran-5-yl, 2,3-dihydro-benzo[1,4]dioxin-6-yl, 2,3-dihydro-benzofuran-5-yl, or 2,2-difluoro-benzo[1,3]dioxol-5-yl; or a pharmaceutically acceptable salt thereof.

In yet another particular embodiment (for any of the compounds or embodiments described above), $R^1$ is benzothiazol-6-yl, 3-methyl-benzofuran-5-yl, 1H-indazol-6-yl, 3-methyl-1H-indazol-6-yl, or 3-trifluoromethyl-1H-indazol-6-yl; or a pharmaceutically acceptable salt thereof.

In yet another particular embodiment (for any of the compounds or embodiments described above), $R^1$ is 5-methyl-thiophen-2-yl, 5-chloro-thiophen-2-yl, 5-fluorobenzo[b]thiophen-2-yl, 5-trifluoromethyl-thiophen-2-yl, 5-difluoromethyl-thiophen-3-yl, 5-methyl-thiophen-3-yl, 2-methyl-pyridin-4-yl, 2-trifluoromethyl-pyridin-4-yl, 4-trifluoromethyl-pyridin-2-yl, 2-chloro-pyridin-4-yl, 2-methoxypyridin-4-yl, 6-chloropyrimidin-4-yl, 6-chloro-2-methylpyrimidin-4-yl, 2-trifluoromethyl-pyrimidin-4-yl, 4-trifluoromethyl-pyrimidin-2-yl, 2-chloro-6-(trifluoromethyl)pyridin-4-yl, 6-cyclopropylpyrimidin-4-yl, 2-cyclopropylpyridin-4-yl, 5-fluoro-4-methylpyridin-2-yl, 2-cyclopropylpyrimidin-4-yl, 6-chloro-2-(trifluoromethyl)pyrimidin-4-yl, 2,6-dichloropyridin-4-yl, 2-chloro-6-cyclopropylpyridin-4-yl, 2-cyclopropyl-6-(trifluoromethyl)pyridin-4-yl, or 2,6-bis(trifluoromethyl)pyridin-4-yl;

In yet another particular embodiment (for any of the compounds or embodiments described above), $R^1$ is 5-methyl-thiophen-2-yl, 5-chloro-thiophen-2-yl, 5-fluorobenzo[b]thiophen-2-yl, 5-trifluoromethyl-thiophen-2-yl, 5-difluoromethyl-thiophen-3-yl, 5-methyl-thiophen-3-yl, 2-methyl-pyridin-4-yl, 2-trifluoromethyl-pyridin-4-yl, 4-trifluoromethyl-pyridin-2-yl, 2-chloro-pyridin-4-yl, 2-methoxypyridin-4-yl, 6-chloropyrimidin-4-yl, 6-chloro-2-methylpyrimidin-4-yl, 2-trifluoromethyl-pyrimidin-4-yl, 4-trifluoromethyl-pyrimidin-2-yl; or 2-chloro-6-(trifluoromethyl)pyridin-4-yl; or a pharmaceutically acceptable salt thereof.

In yet another Particular embodiment, $R^1$ is 4-chloro-thieno[3,2-c]pyridin-2-yl, 4-chloro-thieno[3,2-c]pyridin-3-yl, thieno[3,2-c]pyridin-2-yl, 3-chloro-imidazo[1,2-a]pyridin-7-yl, benzo[b]thiophen-2-yl, or 4-methylthieno[3,2-c]pyridin-2-yl; or a pharmaceutically acceptable salt thereof.

Representative compounds of Formula (I) where $R^2$, $R^3$, $R^4$ and $R^5$ are each H include:
1-(2-Chloropyridin-4-yl)-3-(4-cyclopropylpyridin-3-yl)imidazolidin-2-one;
1-(4-Cyclopropylpyridin-3-yl)-3-(2-(trifluoromethyl)pyridin-4-yl)imidazolidin-2-one;
1-(4-Cyclopropylpyridin-3-yl)-3-(naphthalen-2-yl)imidazolidin-2-one;
1-(Benzo[b]thiophen-5-yl)-3-(4-cyclopropylpyridin-3-yl)imidazolidin-2-one;
1-(4-Cyclopropylpyridin-3-yl)-3-(3-(trifluoromethyl)phenyl)imidazolidin-2-one;
1-(Benzo[b]thiophen-2-yl)-3-(4-cyclopropylpyridin-3-yl)imidazolidin-2-one;
1-(6-Chloro-2-methylpyrimidin-4-yl)-3-(4-cyclopropylpyridin-3-yl)imidazolidin-2-one;
1-(4-Cyclopropylpyridin-3-yl)-3-(4-(trifluoromethyl)pyridin-2-yl)imidazolidin-2-one;
1-(4-Cyclopropylpyridin-3-yl)-3-(2-methoxypyridin-4-yl)imidazolidin-2-one;
1-(6-Chloropyrimidin-4-yl)-3-(4-cyclopropylpyridin-3-yl)imidazolidin-2-one;
1-(4-Cyclopropylpyridin-3-yl)-3-(4-(trifluoromethyl)pyrimidin-2-yl)imidazolidin-2-one;
1-(4-Cyclopropylpyridin-3-yl)-3-(2-(trifluoromethyl)pyrimidin-4-yl)imidazolidin-2-one;
1-(4-Cyclopropylpyridin-3-yl)-3-(3-(trifluoromethyl)benzo[b]thiophen-5-yl)imidazolidin-2-one;
1-(4-Cyclopropylpyridin-3-yl)-3-(2-fluorobenzo[b]thiophen-5-yl)imidazolidin-2-one;
1-(4-Cyclopropylpyridin-3-yl)-3-(3-methylbenzo[b]thiophen-5-yl)imidazolidin-2-one;
1-(Benzo[b]thiophen-6-yl)-3-(4-cyclopropylpyridin-3-yl)imidazolidin-2-one;
1-(4-Cyclopropylpyridin-3-yl)-3-(2,2-difluorobenzo[d][1,3]dioxol-5-yl)imidazolidin-2-one;
1-(4-Cyclopropylpyridin-3-yl)-3-(3-methylbenzo[b]thiophen-6-yl)imidazolidin-2-one;
1-(4-Cyclopropylpyridin-3-yl)-3-(3-methylbenzofuran-5-yl)imidazolidin-2-one;
1-(2-Chlorobenzo[b]thiophen-5-yl)-3-(4-cyclopropylpyridin-3-yl)imidazolidin-2-one;
1-(4-Cyclopropylpyridin-3-yl)-3-(2,3-dihydro-1H-inden-5-yl)imidazolidin-2-one;
1-(4-Cyclopropylpyridin-3-yl)-3-(5-fluorobenzo[b]thiophen-2-yl)imidazolidin-2-one;
1-(4-Cyclopropylpyridin-3-yl)-3-(3-(trifluoromethyl)benzo[b]thiophen-6-yl)imidazolidin-2-one;
1-(4-Cyclopropyl-pyridin-3-yl)-3-(2-fluoro-3-methyl-benzo[b]thiophen-5-yl)-imidazolidin-2-one;
1-(4-Cyclopropyl-pyridin-3-yl)-3-(2-fluoro-benzo(b)thiophene-6-yl)imidazolidin-2-one;
1-(4-Cyclopropyl-pyridin-3-yl)-3-(4-fluoro-benzo[b]thiophen-6-yl)imidazolidin-2-one;
1-(4-Cyclopropyl-pyridin-3-yl)-3-(5-fluoro-benzo[b]thiophen-6-yl)imidazolidin-2-one;
1-(4-Cyclopropylpyridin-3-yl)-3-(6-fluorobenzo[b]thiophen-5-yl)imidazolidin-2-one;
1-(4-Cyclopropylpyridin-3-yl)-3-(5-fluoro-3-methylbenzo[b]thiophen-6-yl)imidazolidin-2-one;
1-(2-Chloro-pyridin-4-yl)-3-[4-(1-hydroxy-cyclobutyl)pyridin-3-yl]-imidazolidin-2-one;
1-(2-Chloropyridin-4-yl)-3-(4-cyclopentyl-pyridin-3-yl)imidazolidin-2-one;
1-(2-Chloropyridin-4-yl)-3-[4-(1-hydroxycyclopentyl)-pyridin-3-yl]imidazolidin-2-one;
1-[4-(1-Hydroxy-cyclopropyl)-pyridin-3-yl]-3-(3-trifluoromethylphenyl)-imidazolidin-2-one;
1-(4-cyclopropylpyridin-3-yl)-3-(6-cyclopropylpyrimidin-4-yl)imidazolidin-2-one;
1-(4-cyclopropylpyridin-3-yl)-3-(2-cyclopropylpyridin-4-yl)imidazolidin-2-one;
1-(4-cyclopropylpyridin-3-yl)-3-(5-fluoro-4-methylpyridin-2-yl)imidazolidin-2-one;
1-(4-cyclopropylpyridin-3-yl)-3-(2-cyclopropylpyrimidin-4-yl)imidazolidin-2-one;
1-(6-chloro-2-(trifluoromethyl)pyrimidin-4-yl)-3-(4-cyclopropylpyridin-3-yl)imidazolidin-2-one;
1-(4-cyclopropylpyridin-3-yl)-3-(2,6-dichloropyridin-4-yl)imidazolidin-2-one;
1-(2-chloro-6-cyclopropylpyridin-4-yl)-3-(4-cyclopropylpyridin-3-yl)imidazolidin-2-one;
1-(2-cyclopropyl-6-(trifluoromethyl)pyridin-4-yl)-3-(4-cyclopropylpyridin-3-yl)imidazolidin-2-one; and
1-(2,6-bis(trifluoromethyl)pyridin-4-yl)-3-(4-cyclopropylpyridin-3-yl)imidazolidin-2-one; or a pharmaceutically acceptable salt thereof.

Representative compounds of Formula (II) or (III) include:
(1S,5R)-2-(4-cyclopropylpyridin-3-yl)-4-(2-(trifluoromethyl)pyridin-4-yl)-2,4-diazabicyclo[3.1.0]hexan-3-one;
(1R,5S)-2-(4-cyclopropylpyridin-3-yl)-4-(2-(trifluoromethyl)pyridin-4-yl)-2,4-diazabicyclo[3.1.0]hexan-3-one;
(1S,5R)-2-(2-chloropyridin-4-yl)-4-(4-cyclopropylpyridin-3-yl)-2,4-diazabicyclo[3.1.0]hexan-3-one;
(1R,5S)-2-(2-chloropyridin-4-yl)-4-(4-cyclopropylpyridin-3-yl)-2,4-diazabicyclo[3.1.0]hexan-3-one;
(1S,5R)-2-(4-cyclopropylpyridin-3-yl)-4-(2-methoxypyridin-4-yl)-2,4-diazabicyclo[3.1.0]hexan-3-one; and
(1R,5S)-2-(4-cyclopropylpyridin-3-yl)-4-(2-methoxypyridin-4-yl)-2,4-diazabicyclo[3.1.0]hexan-3-one; or a pharmaceutically acceptable salt thereof Compounds of particular interest include: 1-(2-chloropyridin-4-yl)-3-(4-cyclopropylpyridin-3-yl)imidazolidin-2-one;
1-(4-cyclopropylpyridin-3-yl)-3-(2-(trifluoromethyl)pyridin-4-yl)imidazolidin-2-one;

1-(4-cyclopropylpyridin-3-yl)-3-(3-(trifluoromethyl)phenyl)imidazolidin-2-one;
1-(2-chloro-pyridin-4-yl)-3-[4-(1-hydroxy-cyclobutyl)-pyridin-3-yl]-imidazolidin-2-one;
1-(6-chloro-2-methylpyrimidin-4-yl)-3-(4-cyclopropylpyridin-3-yl)imidazolidin-2-one;
1-(4-cyclopropylpyridin-3-yl)-3-(2-methoxypyridin-4-yl)imidazolidin-2-one;
(1R,5S)-2-(4-cyclopropylpyridin-3-yl)-4-(2-(trifluoromethyl)pyridin-4-yl)-2,4-diazabicyclo[3.1.0]hexan-3-one;
(1S,5R)-2-(2-chloropyridin-4-yl)-4-(4-cyclopropylpyridin-3-yl)-2,4-diazabicyclo[3.1.0]hexan-3-one;
(1R,5S)-2-(4-cyclopropylpyridin-3-yl)-4-(2-methoxypyridin-4-yl)-2,4-diazabicyclo[3.1.0]hexan-3-one;
1-(2-chloro-6-(trifluoromethyl)pyridin-4-yl)-3-(4-cyclopropylpyridin-3-yl)imidazolidin-2-one;
1-(6-chloro-2-(trifluoromethyl)pyrimidin-4-yl)-3-(4-cyclopropylpyridin-3-yl)imidazolidin-2-one;
1-(4-cyclopropylpyridin-3-yl)-3-(2,6-dichloropyridin-4-yl)imidazolidin-2-one;
1-(2-chloro-6-cyclopropylpyridin-4-yl)-3-(4-cyclopropylpyridin-3-yl)imidazolidin-2-one;
1-(2-cyclopropyl-6-(trifluoromethyl)pyridin-4-yl)-3-(4-cyclopropylpyridin-3-yl)imidazolidin-2-one; and
1-(2,6-bis(trifluoromethyl)pyridin-4-yl)-3-(4-cyclopropylpyridin-3-yl)imidazolidin-2-one; or a pharmaceutically acceptable salt thereof.

Other compounds include those described in the Example section below, in particular, those compounds having an $IC_{50}$ less than 1 μM (or 1,000 nM), preferably, less than 500 nM, more preferably, less than 100 nM.

In another aspect of the present invention a pharmaceutical composition is provided which comprises a compound of Formula (I), (II), or (III), or a pharmaceutically acceptable salt thereof, and a pharmaceutically acceptable carrier or excipient. The pharmaceutical composition optionally comprises at least one additional pharmaceutical agent (suitable pharmaceutical agents are described herein below).

In yet another aspect of the present invention, a method of treating a disease, disorder, or syndrome mediated by Cyp17 inhibition (such as those described herein below) is provided, where the method comprises administering a compound according to Formula (I), (II), or (III), or a pharmaceutical composition comprising the compound of Formula (I), (II), or (III), and pharmaceutically acceptable excipients, to a subject in need thereof.

Another aspect of the present invention includes a compound according to Formula (I), (II), or (III), for use in therapy (e.g., the use of a compound for the treatment of a disease, disorder, or syndrome mediated by Cyp17 inhibition).

Yet another aspect of the present invention includes a method for treating a disease, disorder or syndrome mediated by Cyp17 inhibition comprising the step of administering (i) a first composition comprising a compound according to Formula (I), (II), or (III), or a pharmaceutically acceptable salt thereof, and a pharmaceutically acceptable carrier or excipient; and (ii) a second composition comprising at least one additional pharmaceutical agent and a pharmaceutically acceptable carrier or excipient;

wherein said at least one additional pharmaceutical agent is an anticancer agent, chemotherapy agent, or antiproliferative compound. The first and second compositions may be administered either simultaneously or sequentially in any order.

In one particular embodiment for each of the methods and uses described above, the disease, disorder, or syndrome is selected from the group consisting of cancer (in particular, prostate cancer) and inflammation.

DEFINITIONS

As used herein, the terms "alkyl" refers to a hydrocarbon radical of the general formula $C_nH_{2n+1}$. The alkane radical may be straight or branched. For example, the term "$(C_1-C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above.

"Halo-substituted alkyl" refers to an alkyl group, as defined above, substituted with at least one halogen atom. For example, when the halogen atom is fluoro, common haloalkyl groups include fluoromethyl, difluoromethyl, trifluoromethyl, 2,2,2-trifluoroethyl, 2,2,2,1,1-pentafluoroethyl, and the like. Mixed halogen substitution are also included (e.g., chlorofluoromethyl).

The term "alkenyl" refers to a monovalent group derived from a hydrocarbon having at least one carbon-carbon double bond. The term "$C_2-C_6$-alkenyl" refers to a monovalent group derived from a hydrocarbon having two to six carbon atoms and comprising at least one carbon-carbon double bond. The alkenyl group can be unbranched or branched. Representative examples of alkenyl include vinyl, 1-propenyl, 2-propenyl, 1-methyl-1-propenyl, 1-methyl-2-propenyl, 2-methyl-1-propenyl, 2-methyl-2-propenyl, 1-butenyl, 2-butenyl, 3-butenyl, and so on.

The term "alkynyl" refers to a monovalent group derived from a hydrocarbon having at least one carbon-carbon triple bond. The term "$C_2-C_6$-alkynyl" refers to a monovalent group derived from a hydrocarbon having two to six carbon atoms and comprising at least one carbon-carbon triple bond. The alkynyl group can be unbranched or branched. Representative examples include ethynyl, propynyl, butyn-1-yl, butyn-2-yl, and so on.

The term "hydroxy-substituted alkyl" refers to an alkyl group, as defined above, substituted with one or more hydroxyl (—OH) groups (e.g., —CH$_2$OH, —CH(OH)$_2$, —CH(OH)—CH(OH, —CH(OH)—CH$_3$, and so on). Preferably, the alkyl group is substituted with 1 to 2 hydroxyl groups, more preferably one hydroxyl group.

"Halogen" or "halo" may be fluorine, chlorine, bromine or iodine (preferred halogens as substituents are fluorine and chlorine).

The term "oxo" or —C(O)— refers to a carbonyl group. For example, a ketone, aldehyde, or part of an acid, ester, amide, lactone, or lactam group.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring. For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl(bicyclo[2.2.1]heptyl), norbornenyl, bicyclo[2.2.2]octyl, and the like. When optionally substituted, the group is attached via the carbocyclic ring and not the substituent.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) each independently selected from sulfur, oxygen and/or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When optionally substituted, the group is attached via the heterocyclic ring and not the substituent. Unless specified otherwise, the heterocyclic ring may be attached via any valence available ring member (e.g., replacement of a H attached to the heterocyclic ring).

The term "fused phenyl" refers to a phenyl group fused to another ring, such as another phenyl (i.e., naphthalene (e.g., naphthalen-2-yl, naphthalen-1-yl), a partially or fully saturated cycloalkyl (e.g., indan-5-yl, 2,3-dihydro-1H-indenyl, or tetrahydronaphthalenyl, etc.), a heteroaryl (e.g., 1H-indol-5-yl, 1H-indol-6-yl, benzothiazol-5-yl, benzothiazol-6-yl, benzo[b]thiophen-5-yl, quinolin-6-yl, quinolin-7-yl, isoquinolin-5-yl, isoquinolin-6-yl isoquinolin-7-yl, isoquinolin-8-yl, indazol-4-yl, indazol-5-yl, indazol-6-yl, indazol-7-yl, benzofuran-4-yl, benzofuran-5-yl, benzofuran-6-yl, benzofuran-7-yl, benzimidazol-4-yl, or quinoxalin-6-yl, benzooxazol-5-yl, benzo[d]isoxazol-5-yl, benzo[d]isoxazol-6-yl, 1H-benzoimidazol-4-yl, 1H-benzoimidazol-5-yl, 1H-benzoimidazol-6-yl, 1H-benzoimidazol-7-yl, 1H-benzotriazol-5-yl, etc.) or a partially saturated or fully saturated heterocycle (e.g., indolin-4-yl, indolin-5-yl, indolin-6-yl, indolin-7-yl, 1,2-dihydroquinolin-6-yl, 1,2,3,4-tetrahydro-quinolin-6-yl, 1,2,3,4-tetrahydro-quinolin-7-yl, 2,3-dihydro-1H-benzo[d]imidazolyl, 2,3-dihydro-1H-indazolyl, 2,3-dihydrobenzo[d]oxazolyl, 2,3-dihydrobenzo[1,4]dioxin-6-yl, 2,3-dihydro-benzofuran-5-yl, benzo[1,3]dioxol-5-yl, 2,3-dihydro-1H-indazol-5-yl, 2,3-dihydro-1H-indazol-6-yl, etc.), where the group is attached via one of the phenyl carbon atoms. When substituted, the fused phenyl group is attached via the phenyl and not the substituent. When substituted, the fused phenyl can be substituted on any valence available ring atom (e.g., replacement of a H atom attached to the fused phenyl) within the fused system. For example, a benzofuranyl group may be substituted on the phenyl or furanyl portion of the benzofuranyl group.

The term "heteroaryl" or "heteroaromatic ring" refers to aromatic moieties containing at least one heteroatom (e.g., oxygen, sulfur, nitrogen or combinations thereof) within a 5- to 6-membered aromatic ring system (e.g., pyrrolyl, pyridyl, pyrazolyl, thienyl, furanyl, oxazolyl, imidazolyl, tetrazolyl, triazinyl, pyrimidyl, pyrazinyl, thiazolyl, isothiazolyl, etc.). A typical single heteroaryl ring is generally a 5- to 6-membered ring containing one to three heteroatoms each independently selected from oxygen, sulfur and nitrogen. When optionally substituted, the group is attached via the heteroaryl ring and not the substituent.

The term "fused heteroaryl" refers to a heteroaryl group fused to another ring, such as another heteroaryl (e.g. purinyl, thieno[3,2-c]pyridinyl (e.g., thieno[3,2-c]pyridin-2-yl and thieno[3,2-c]pyridin-3-yl), imidazo[1,2-a]pyridinyl (e.g., imidazo[1,2-a]pyridin-3-yl, imidazo[1,2-a]pyridin-6-yl, imidazo[1,2-a]pyridin-7-yl and 3H-imidazo[4,5-b]pyridin-6-yl), or benzo[b]thiophenyl, etc.), phenyl (e.g., benzo[b]thiophen-2-yl, benzo[b]thiophen-3-yl, quinolin-2-yl, quinolin-3-yl, benzooxazol-2-yl, benzothiazol-2-yl, 1H-indol-2-yl, 1H-indol-3-yl, isoquinolin-1-yl, isoquinolin-3-yl, isoquinolin-4-yl, benzofuran-2-yl, benzofuran-3-yl, indazol-3-yl, benzimidazol-2-yl, etc.), a partially or fully saturated cycloalkyl (e.g., 4,5,6,7-tetrahydrobenzo[d]oxazolyl, 4,5,6,7-tetrahydro-1H-indolyl, 5,6,7,8-tetrahydroquinolinyl, 5,6,7,8-tetrahydroisoquinolinyl, 4,5,6,7-tetrahydrobenzo[b]thiophenyl, 4,5,6,7-tetrahydrobenzofuranyl, 4,5,6,7-tetrahydro-1H-indazolyl, 4,5,6,7-tetrahydro-1H-benzo[d]imidazolyl, or 4,5,6,7-tetrahydrobenzo[d]oxazolyl, etc.), or a partially saturated or fully saturated heterocycle (e.g., 8,9-dihydro-7H-purinyl, 2,3-dihydrothieno[3,2-c]pyridinyl, 4,5,6,7-tetrahydro-thieno[2,3-c]pyridin-2-yl, 4,5,6,7-tetrahydrothieno[3,2-c]pyridinyl, or 5,6,7,8-tetrahydroimidazo[1,2-a]pyridinyl, etc.), where the heteroaryl group is attached via one of the valence available heteroaryl ring atoms. When substituted, the heteroaryl group is attached via the fused heteroaryl and not the substituent. When substituted, the fused heteroaryl can be substituted on any valence available ring atom (e.g., replacement of a H atom attached to the fused heteroaryl) within the fused system. For example, an imidazo[1,2-a]pyridinyl group may be substituted on the imidazole or pyridine portion of the fused system.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The term "animal" refers to humans (male or female), companion animals (e.g., dogs, cats and horses), zoo animals, marine animals, birds and other similar animal species. Preferred animals are mammals, in particular a human.

The phrase "pharmaceutically acceptable" indicates that the substance or composition must be compatible chemically and/or toxicologically, with the other ingredients comprising a formulation, and/or the mammal being treated therewith.

The term "compounds of the present invention" (unless specifically identified otherwise) refer to compounds of Formula (I), (II), or (III), or pharmaceutically acceptable salts of the compounds, as well as, all stereoisomers (including diastereoisomers and enantiomers), tautomers and isotopically labeled compounds.

DETAILED DESCRIPTION

The present invention provides compounds and pharmaceutical formulations thereof that are useful in the treatment of diseases, conditions and/or disorders modulated by the inhibition of 17α-hydroxylase/$C_{17,20}$-lyase.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme I below provides a potential route for synthesizing compounds of Formula (I), where $R^2$, $R^3$, $R^4$ and $R^5$ are each independently $CH_3$ or H (referred to below as a compound of Formula (I-a).

GENERAL SCHEMES

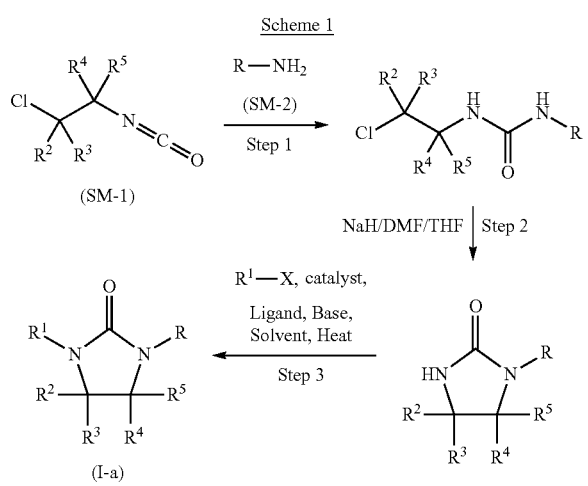

In Scheme I above, R is represented by the following group (where $R^6$ is as defined above).

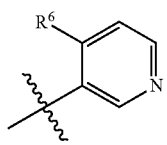

Step-1 & 2:

The intermediate products of Steps 1 and 2 may be synthesized using methods analogous to those described by Kak-Shan Shia, et al., in *J. Med. Chem.*, 2002, 45, 1644-1655 using the desired starting materials which are available commercially or synthesized using known procedures described in the art. For example, a variety of 2-chloroalkyl isocyanates can be prepared using the methods described by C K Johnson in *J Org Chem* (1967), 32(5), 1508-10. The reaction times in certain cases were prolonged to increase the % yield as compared to reported yields in the above mentioned J Med Chem reference.

Step-3:

The products of Step-2 obtained as described above may be converted into the desired products by reacting with the appropriate alkyl or aryl halides preferably chloro/bromo alkyl or aryl derivatives using conditions well know to those of skill in the art, e.g., the Buchwald-Hartwig C—N coupling conditions or NaH/DMF, and the like. Preferred conditions are those known as the 'Buchwald-Hartwig" reaction, e.g., in the presence of (a) a catalyst, such as copper iodide, (b) a base, such as potassium phosphate or cesium carbonate; and (c) a ligand, such as trans-1,2-diamino cyclohexane, in the presence of suitable solvents (e.g., 1,4-dioxane) at temperatures ranging from about room temperature to the refluxing temperature of the solvent. When a protection group is used, then the protecting group is removed using the conditions appropriate for the particular protecting group used to produce compounds of the present invention. For a more detailed description, see the Example section below.

Alternatively, the substituents $R^1$ and R may be introduced in the reverse. For example, instead of starting with R—NH, $R^1$—$NH_2$ is used as the starting material. The R group is then introduced in step 3 by using R—X instead of $R^1$—X.

Scheme 2 describes how one could make the starting material (SM-1) above where $R^2$, $R^3$, $R^4$ and/or $R^5$ are other than hydrogen.

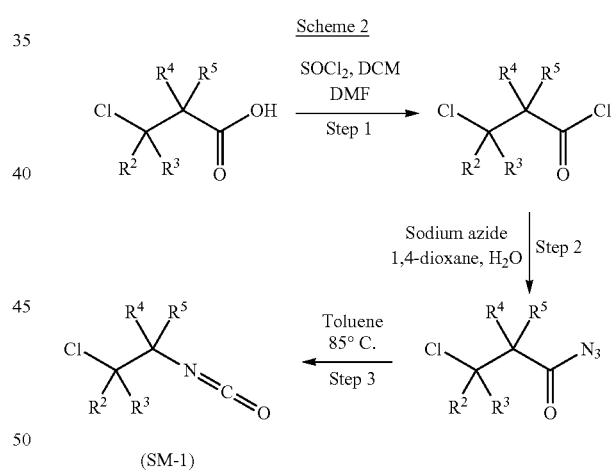

The desired chloro carboxylic acid is first converted to its corresponding acid chloride derivative using procedures well-known to those of skill in the art. For example, the carboxylic acid derivative may be treated with thionyl chloride in the presence of dimethylformamide (DMF) and a solvent (e.g., dichloromethane (DCM)). Other chlorinating agents may be used, e.g., phosphorous trichloride or phosphorous pentachloride. The acid chloride can then be converted to its corresponding azide by treatment with sodium azide. The azide is then converted to the desired isocyanate (SM-1) by the Curtius rearrangement, e.g., heating the azide at elevated temperatures.

Scheme 3 describes a potential route for making SM-2, where $R^6$ is ($C_3$-$C_5$)cycloalkyl.

Scheme 3

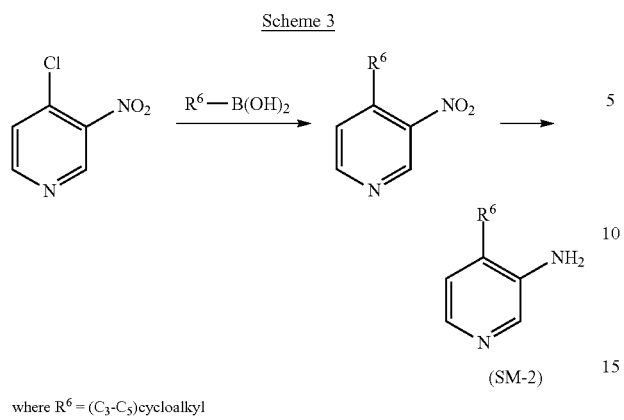

(SM-2)

where $R^6 = (C_3-C_5)$cycloalkyl $R^6$ can be introduced into SM-2 using the desired $(C_3-C_5)$ cycloalkyl boronic acid in the presence of tetrakis(triphenylphosphine)palladium(0) followed by reduction of the nitro group using standard reduction procedures well-known to those of skill in the art (e.g., treatment with ammonium chloride in the presence of zinc powder).

Scheme 4 provides an alternative synthesis for preparing compounds of Formula (I), (II) or (III).

Scheme 4

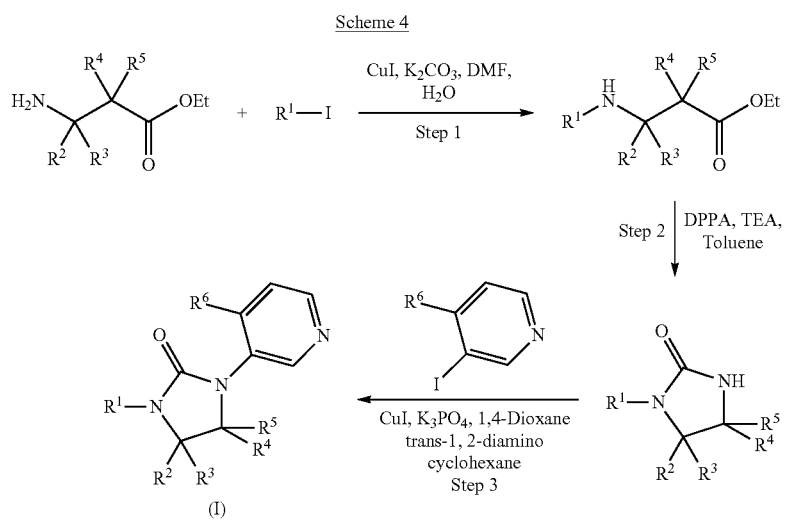

The desired $R^1$ group may be attached to the desired amino carboxylate compound via Buchwald-Hartwig C—N coupling conditions or NaH/DMF, and the like. The cyclic urea is then formed using methods analogous to those described by Kak-Shan Shia, et al., in *J Med. Chem.*, 2002, 45, 1644-1655. The pyridine derivative may then be coupled to the imidazoline via a Buchwald-Hartwig C—N coupling reaction described previously.

Alternatively, the unsymmetrical disubstituted-1H-imidazolin-2(3H)-ones can be prepared by other methods discussed by T. Hafner, et al., in Synthesis (2007) 9, 1403-1411 (e.g., Brazier, S. A, et al., *J Chem Soc* (1912), 101, 2352 and Schonherr, H. J., et al, *Chem Ber* (1970), 103, 1037).

Scheme 5 provides another alternative synthesis for preparing compounds of Formula (I), where $R^2$ (or $R^3$) and $R^4$ (or $R^5$) are H (referred to below as Formula (I-b)).

Scheme 5

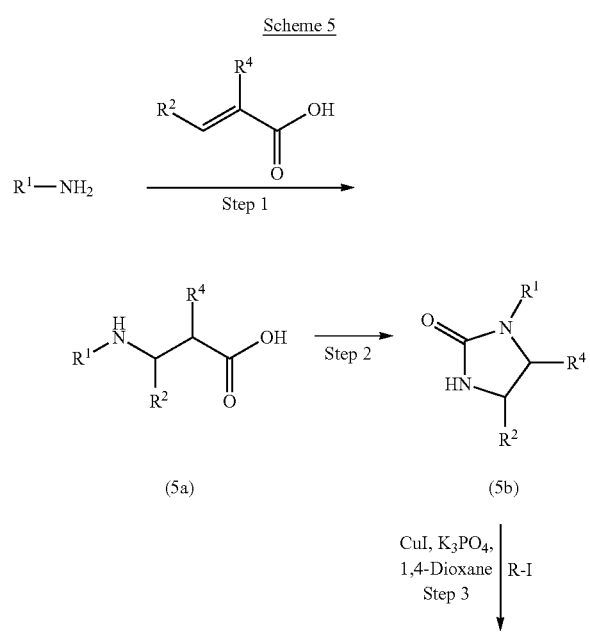

-continued

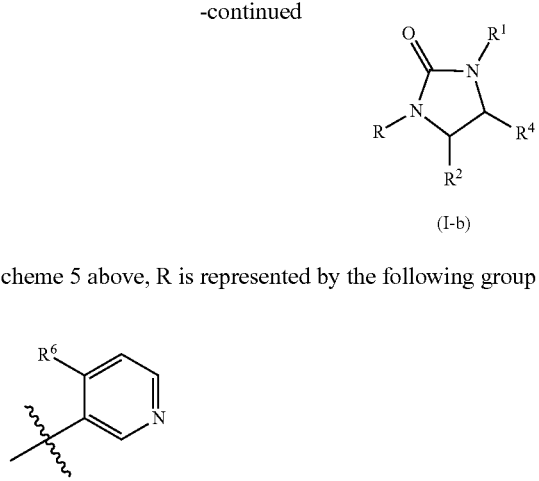

In Scheme 5 above, R is represented by the following group

Intermediate (5a) may be formed via a Michael addition of the desired amine ($R^1$—$NH_2$) to the desired acrylic acid using procedures well-known to those of skill in the art. For example, the amine and acrylic acid in a suitable solvent (e.g., toluene) are heated at an elevated temperature (e.g., about 70° C. to about 100° C.) under an inert atmosphere. The amino acid intermediate (5a) may then be cyclized to form the cyclic urea intermediate (5b). For example, the cyclic urea intermediate (I-4b) may be formed by treating the amino acid intermediate (5a) with an activating agent (e.g., diphenyl phosphoryl azide (DPPA)) in the presence of an amine (e.g., triethylamine) and appropriate solvent (e.g., toluene) at elevated temperatures. The desired A group may be coupled to the cyclic urea intermediate (5b) using standard coupling conditions described above to form the a compound of the Formula (I-b).

Scheme 6 provides a potential route for the synthesis of compounds of Formula (II) or (III).

Scheme 6

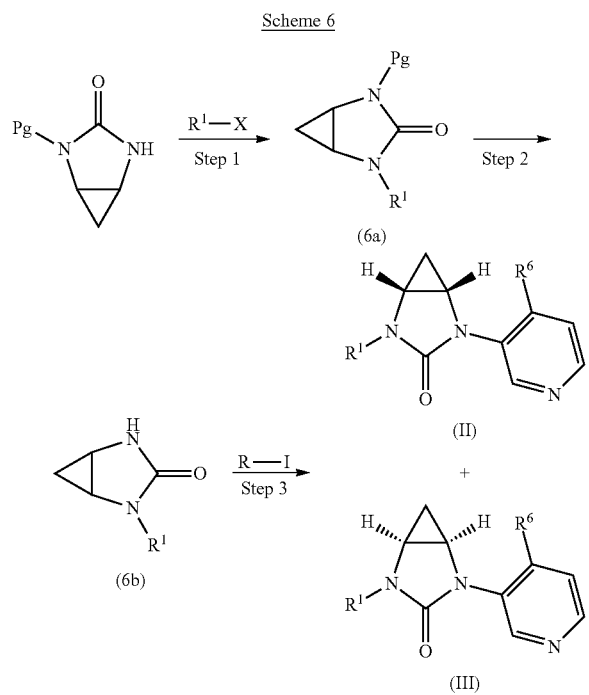

The amino-protected 3-oxo-2,4-diazabicyclo[3.1.0]hexane is generally available from commercial sources (e.g., benzyl 3-oxo-2,4-diazabicyclo[3.1.0]hexane-2-carboxylate which is available from Rare Chemicals Screening Compounds, Maybridge Screening collection, Interchim Screening Library, Ambinter Stock Screening Collection or Aurora Screening Library; or prepared using the procedures described by Witiak, D. T., in *J. Med Chem*, 1978, 21(12) 1194-1197). The $R^1$ group can be introduced using the Buchwald-Hartwig reaction. For example, treating benzyl 3-oxo-2,4-diazabicyclo[3.1.0]hexane-2-carboxylate with the desired halo-substituted aryl or heteroaryl group ($R^1$—X, where X is Br or I) in the presence of Xantphos, a Palladium catalyst (e.g., tris(dibenzylideneacetone(dipalladium(0)) at elevated temperatures (e.g., about 100° C.). The amino-protecting group (Pg) is then removed using the appropriate conditions for the particular protecting group. Once the protecting group is removed, then the desired $R^6$ substituted 3-pyridinyl group may then be coupled to the 3-oxo-2,4-diazabicyclo[3.1.0]hexane derivative (6b) via a Buchwald-Hartwig C—N coupling reaction described previously. In Scheme 6 above, R is represented by the following group

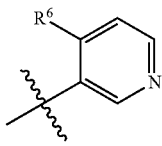

The Example section below provides a more detailed description of the synthetic schemes as well as other alternative processes for making compounds of the present invention which could be easily modified (e.g., substituting different starting materials) by those of skill in the art.

The compounds and intermediates described herein may be isolated and used as the compound per se or its salt. Many of the compounds represented by Formula (I), (II), (III), (I-a), and (I-b) are capable of forming acid addition salts, particularly pharmaceutically acceptable acid addition salts. Pharmaceutically acceptable acid addition salts of the compound of Formula (I), (II), (III), (I-a) and (I-b) include those of inorganic acids, for example, hydrohalic acids such as hydrochloric acid, hydrobromic acid or hydroiodic acid, nitric acid, sulfuric acid, phosphoric acid; and organic acids, for example aliphatic monocarboxylic acids such as formic acid, acetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of Formula (I), (II), (III), (I-a) or (I-b) by known salt-forming procedures.

Compounds of the present invention which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of Formula (I), (II), (III), (I-a) and (I-b) by known salt-forming procedures.

In those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof.

The present invention includes all pharmaceutically acceptable isotopically-labeled compounds of the present invention wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, C chlorine, such as $^{36}Cl$, fluorine, such as $^{18}F$, iodine, such as $^{123}I$ and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of the present invention can generally be prepared by conventional techniques known to those skilled in the art or by processes analogous to those described in the accompanying Examples and Preparations Sections using an appropriate isotopically-labeled reagent in place of the non-labeled reagent previously employed.

The compounds of the present invention may exist in unsolvated as well as solvated forms with pharmaceutically acceptable solvents such as water, ethanol, and the like, and it is intended that the invention embrace both solvated and unsolvated forms. For purposes of the present invention, solvates (including hydrates) are considered pharmaceutical compositions, e.g., a compound of Formula (I), (II), (III), (I-a) or (I-b) (or pharmaceutically acceptable salt thereof) in combination with an excipient, wherein the excipient is a solvent.

Compounds of the present invention are useful for treating diseases, conditions and disorders mediated by the regulation of 17α-hydroxylase/$C_{17,20}$-lyase (e.g., cancer (in particular, prostate cancer) or inflammation); consequently, the compounds of the present invention (including the compositions and processes used therein) may be used in the manufacture of a medicament for the therapeutic applications described herein. Hence, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

A Cyp17 inhibitor of the present invention may be usefully combined with at least one additional pharmacologically active compound, particularly in the treatment of cancer. For example, a compound of the present invention, as defined above, may be administered simultaneously, sequentially or separately in combination with one or more agents selected from chemotherapy agents, e.g. mitotic inhibitors such as a taxane (e.g., paclitaxel or docetaxel), a vinca alkaloid (e.g., vincristine, vinblastine, vinorelbine or vinflunine) or other anticancer agents, e.g. cisplatin, 5-fluorouracil or 5-fluoro-2-4(1H,3H)-pyrimidinedione (5FU), flutamide or gemcitabine. Such combinations may offer significant advantages, including synergistic activity, in therapy.

A compound of the present invention may also be used in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylamino-gelda-namycin, NSC330507), 17-DMAG (17-dimethylaminoethylamino-17-demethoxy-geldana-mycin, NSC707545), IPI-504, CNF1010, CNF2024, CNF1010 from Conforma Therapeutics; temozolomide (TEMODAL); kinesin spindle protein inhibitors, such as SB715992 or SB743921 from GlaxoSmithKline, or pentamidine/chlorpromazine from CombinatoRx; PI3K inhibitors; RAF inhibitors; EDG binders, antileukemia compounds, ribonucleotide reductase inhibitors, S-adenosylmethionine decarboxylase inhibitors, antiproliferative anti-bodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atame-stane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. un-der the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Amino glutethimide can be administered, e.g., in the form as it is marketed, e.g. under the trademark, ORIMETEN. A combination of the invention comprising a chemo-therapeutic agent which is an aromatase inhibitor is particularly useful for the treatment of hormone receptor positive tumors, e.g., breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of in-hibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g., under the trademark HOLOXAN.

The term "antineoplastic antimetabolite" includes, but is not limited to, 5-Fluorouracil or 5-FU, capecitabine, gemcitabine, DNA demethylating compounds, such as 5-azacy-tidine and decitabine, methotrexate and edatrexate, and folic acid antagonists such as pemetrexed. Capecitabine can be administe-red, e.g., in the form as it is marketed, e.g. under the trademark XELODA. Gemcitabine can be administered, e.g., in the form as it is marketed, e.g. under the trademark GEMZAR. The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib; h) compounds targeting, decreasing or inhibiting the activity of members of the c-Abl family, their gene-fusion products (e.g. BCR-Abl kinase) and mutants, such as com-pounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825); i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor); j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (mw<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially WO 96/30347 (e.g. compound known as CP 358774), WO 96/33980 (e.g. compound ZD 1839) and WO 95/03283 (e.g. compound ZM105180); e.g. trastuzumab (Herceptin), cetuximab (Erbitux), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and 1) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g., inhibitors of phosphatase 1, phosphatase 2A, or CDC25, e.g. okadaic acid or a derivative thereof.

Compounds which induce cell differentiation processes are e.g. retinoic acid, or tocopherol or tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune), everolimus (CerticanO), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. An example HSP90 inhibitor is AUY922.

The term "antiproliferative antibodies" as used herein includes, but is not limited to, trastuzumab (Herceptin), Trastuzumab-DM1, erbitux, bevacizumab (Avastin), rituximab (Rituxan), PRO64553 (anti-CD40) and 2C4 Antibody. By antibodies is meant e.g. intact monoclonal antibodies, polyclonal antibodies, multispe-cific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2-alpha-hydroxy ribose (arabinoside) derivative of deoxycytidine. Also included is the purine analog of hypoxanthine, 6-mercaptopurine (6-MP) and fludarabine phosphate.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-epihydrocotisol, cortexolone, 17-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

EXAMPLES

The following abbreviations used in the examples below have the corresponding meanings:
DBU 1,8-Diazabicyclo[5.4.0]undec-7-ene
DIPA Diisopropylamine
DPPA Diphenylphosphoryl Azide
DCM Dichloromethane
DCE Dichloroethane
DMA N,N-dimethylacetamide
DMF N,N-Dimethylformamide
DMSO Dimethylsulfoxide
TEA Triethylamine
THF Tetrahydrofuran
NaBH(OAc)$_3$ Sodium triacetoxy borohydride
Pd$_2$(dba)$_3$ Tris(dibenzylideneacetone)dipalladium(0)
Pd(PPh$_3$)$_4$ Tetrakis(triphenylphosphine)Palladium(0)
PTSA Para-toluene sulphonic acid
TES Triethyl silane
LDA Lithium Diisopropyl amide
LiHMDS Lithium bis(trimethylsilyl)amide
Xantphos 4,5-Bis(diphenylphosphino)-9,9-dimethylxanthene
TLC Thin Layer Chromatography
NMR Nuclear Magnetic Resonance
LCMS Liquid chromatography Mass spectrometry
HPLC High Performance Liquid Chromatography
Benzyl 3-oxo-2,4-diazabicyclo[3.1.0]hexane-2-carboxylate is available from Combi-Blocks, Inc. (USA), Maybridge (United Kingdom), or Interchim (France).

Example 1

Preparation of 1-(2-chloropyridin-4-yl)-3-(4-cyclopropylpyridin-3-yl)imidazolidin-2-one (1A)

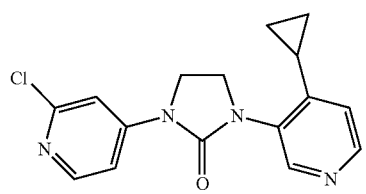

(1A)

Preparation of Intermediate of 4-cyclopropyl-3-nitropyridine (I-1a)

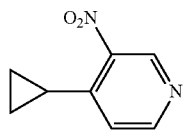

(I-1a)

4-Chloro-3-nitropyridine (100 mg, 0.630 mmol) and cyclopropyl boronic acid (10.0 mg, 0.091 mmol) were added to a solution of xylene (3 mL) previously purged with argon (10 minutes). The reaction mixture was purged with argon for a further 15 minutes, followed by the addition of potassium carbonate (174.35 mg, 1.26 mmol) and Pd(PPh$_3$)$_4$ (34.5 mg, 0.063 mmol). The resulting mixture was heated to reflux at 130° C. overnight. The reaction was monitored by TLC (30% ethylacetate in hexane). The reaction mixture was cooled and concentrated to afford the crude product. Purification by column chromatography on silica gel (15% ethyl acetate in hexane) afforded 110 mg of the product (100% yield). LCMS Purity: 99%, m/z=165 (M+1)

Preparation of Intermediate 4-cyclopropylpyridin-3-amine (I-1b)

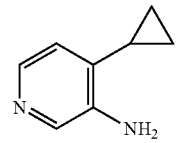

(I-1b)

Zinc powder (223.2 mg, 3.41 mmol) and ammonium chloride solution (365 mg, 6.8 mmol) were added to a stirred solution of 4-cyclopropyl-3-nitropyridine (I-1a: 70 mg, 0.426 mmol) in dry THF (2 mL) at 0° C. and the resulting mixture was stirred at room temperature for 1 hour. The reaction was monitored by TLC (10% methanol in CHCl$_3$). The reaction mixture was filtered over celite bed and washed with THF and filtrate was concentrated. The residue was dissolved in ethyl acetate and washed with water and saturated brine and dried over sodium sulphate and concentrated to afford 450 mg of the product (100% yield).

$^1$H NMR (CDCl$_3$, 300 MH$_z$): δ 8.10 (s, 1H), 7.95 (d, 1H), 6.90 (d, 1H), 4.1 (bs, 2H), 1.75-1.60 (m, 1H), 1.10-0.95 (q, 2H), 0.70-0.60 (q, 2H). LCMS Purity: 85%, m/z=135.1 (M+1)

Preparation of Intermediate 1-(2-chloroethyl)-3-(4-cyclopropylpyridin-3-yl)urea (I-1c

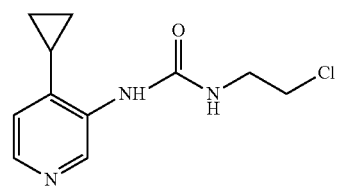

(I-1c)

1-Chloro-2-isocyanatoethane (472 mg, 4.477 mmol) was added drop wise to a stirred mixture of 4-cyclopropylpyridin-3-amine (I-1b: 400 mg, 2.78 mmol) in toluene (10 mL) at 0°

C. The resulting mixture was stirred at room temperature for 2 hours. The reaction was monitored by TLC (10% methanol in CHCl₃). The crude product was concentrated and purified by column chromatography on silica gel (2% methanol in CHCl₃) afforded 200 mg of the product (28% yield).

¹H NMR (DMSO-D₆, 400 MH$_Z$): δ 8.84 (s, 1H), 8.14 (s, 1H), 8.08-8.07 (d, 1H), 6.97-6.94 (t, 1H), 6.88-6.87 (d, 1H), 3.69-3.66 (t, 2H), 3.46-3.42 (dd, 2H), 1.92-1.86 (m, 1H), 1.06-1.01 (q, 2H), 0.73-0.69 (q, 2H). LCMS Purity: 97%, m/z=240.1 (M+1)

Preparation of Intermediate 1-(4-cyclopropylpyridin-3-yl)imidazolidin-2-one (I-1d)

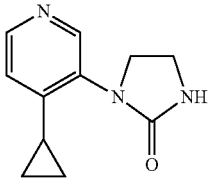

(I-1d)

1-(2-Chloroethyl)-3-(4-cyclopropylpyridin-3-yl)urea (I-1c: 200 mg, 0.836 mmol) in dry THF was added drop wise to a stirred mixture of NaH (40.16 mg, 1.67 mmol) in dry THF (5 mL) at 0° C. over a period of 10 minutes. The resulting mixture was stirred at room temperature for 2 hours. The reaction was monitored by TLC (10% methanol in CHCl₃). The reaction mixture was quenched with methanol and concentrated to afford the crude product. Purification by column chromatography on silica gel (2% methanol in CHCl₃) afforded 140 mg of the product (94% yield).

¹H NMR (DMSO-D₆, 300 MH$_Z$): δ 8.31-8.27 (m, 2H), 6.88-6.83 (m, 2H), 3.81-3.76 (t, 2H), 3.48-3.46 (t, 2H), 2.10-1.95 (m, 1H), 1.07-1.04 (q, 2H), 0.79-0.76 (q, 2H). LCMS Purity: 97% m/z=204.1 (M+1)

Preparation of the title compound 1-(2-chloropyridin-4-yl)-3-(4-cyclopropylpyridin-3-yl)imidazolidin-2-one (1A)

Copper iodide (6.5 mg, 0.034 mmol), trans-N,N'-dimethylcyclohexane-1,2-diamine (4.8 mg, 0.034 mmol) and potassium phosphate (219.3 mg, 1.034 mmol) were added to a solution of 1,4-dioxane (5 mL) previously purged with nitrogen (10 minutes). The reaction mixture was purged with argon for 10 minutes, followed by the addition of 1-(4-cyclopropylpyridin-3-yl)imidazolidin-2-one (I-1d: 70 mg, 0.344 mmol) and 2-chloro-4-iodopyridine (99.09 mg, 0.413 mmol). The reaction mixture was heated to reflux at 120° C. overnight. The reaction was monitored by TLC (10% MeOH in chloroform). The reaction mixture was cooled and partitioned between ethyl acetate and water. The organic layer was concentrated to yield the crude product. Purification by column chromatography on silica gel (2% methanol in CHCl₃) afforded 42 mg of the product (41% yield).

¹H NMR (CDCl₃, 400 MHz): δ 8.70-8.40 (m, 2H), 8.28-8.27 (d, 1H), 7.61-7.59 (dd, 1H), 7.53 (s, 1H), 6.90 (bs, 1H), 4.09-4.02 (m, 4H), 2.0-1.96 (m, 1H), 1.17-1.12 (m, 2H), 0.87-0.83 (m, 2H). LCMS Purity: 99%, m/z=315 (M+1). HPLC Purity: 95%

Example 2

Synthesis of 1-(4-cyclopropylpyridin-3-yl)-3-(2-(trifluoromethyl)pyridin-4-yl)imidazolidin-2-one (2A)

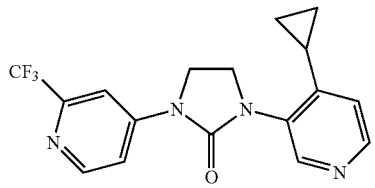

(2A)

Using analogous reagents and reaction conditions as described in Example 1 above, 1-(4-cyclopropylpyridin-3-yl)imidazolidin-2-one (I-1d: 70 mg, 0.344 mmol) was reacted with 4-bromo-2-(trifluoromethyl)pyridine (93.5 mg, 0.413 mmol) 1,4-dioxane (5 mL), copper iodide (6.5 mg, 0.034 mmol), trans-N,N'-dimethylcyclohexane-1,2-diamine (4.8 mg, 0.034 mmol) and potassium phosphate (219 mg, 1.034 mmol) to afford the crude product. Purification by preparative HPLC afforded 40 mg of the product (33% yield).

¹H NMR (CDCl₃, 400 MH$_Z$): δ 8.70-8.40 (m, 2H), 8.28-8.27 (d, 1H), 7.61-7.59 (dd, 1H), 7.53 (s, 1H), 6.90 (bs, 1H), 4.16-4.04 (m, 4H), 2.2-1.95 (m, 1H), 1.17-1.12 (m, 2H), 0.90-0.84 (m, 2H). LCMS Purity: 97%, m/z=349.1 (M+1). HPLC Purity: 94%

Example 3

Preparation of 1-(4-cyclopropylpyridin-3-yl)-3-(naphthalen-2-yl)imidazolidin-2-one (3A)

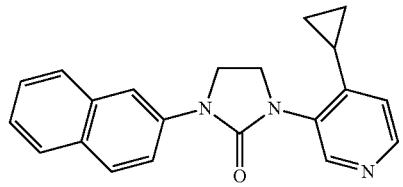

(3A)

Using analogous reagents and reaction conditions as described in Example 1 above, 1-(4-cyclopropylpyridin-3-yl)imidazolidin-2-one (I-1d: 70 mg, 0.344 mmol) was reacted with 2-bromonaphthalene (85.68 mg, 0.413 mmol), 1,4-dioxane (5 mL), copper iodide (6.5 mg, 0.034 mmol), trans-N,N'-dimethylcyclohexane-1,2-diamine (4.8 mg, 0.034 mmol) and potassium phosphate (219 mg, 1.034 mmol) to afford the crude product. Purification by column chromatography on silica gel (2% methanol in CHCl₃), followed by preparative HPLC afforded 13 mg of the product (12% yield).

¹H NMR (CDCl₃, 400 MH$_Z$): δ 8.70-8.30 (m, 2H), 8.15-8.12 (dd, 1H), 7.87 (s, 1H), 7.84-7.79 (m, 2H), 7.73 (s, 1H), 7.47-7.45 (t, 1H), 7.42-7.40 (t, 1H), 7.0-6.70 (m, 1H), 4.23-

4.19 (t, 2H), 4.06-4.02 (t, 2H), 2.15-2.05 (m, 1H), 1.15-1.13 (m, 2H), 0.85-0.84 (m, 2H). LCMS Purity: 100%, m/z=330.2 (M+1). HPLC Purity: 98%

Example 4

Preparation of 1-(benzo[b]thiophen-5-yl)-3-(4-cyclopropylpyridin-3-yl)imidazolidin-2-one (4A)

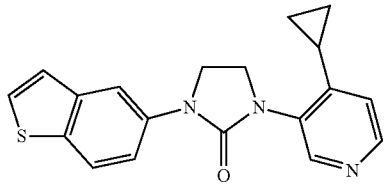

(4A)

Using analogous reagents and reaction conditions as described in Example 1 above, 1-(4-cyclopropylpyridin-3-yl)imidazolidin-2-one (I-1d: 70 mg, 0.344 mmol) was reacted with 5-bromobenzo[b]thiophene (88.1 mg, 0.413 mmol) 1,4-dioxane (5 mL), copper iodide (6.5 mg, 0.034 mmol), trans-N,N'-dimethylcyclohexane-1,2-diamine (4.8 mg, 0.034 mmol) and potassium phosphate (219 mg, 1.034 mmol) to afford the crude product. Purification by preparative HPLC afforded 15 mg of the product (13% yield).

$^1$H NMR (CDCl$_3$, 400 MH$_Z$): δ 8.52 (s, 1H), 8.41 (d, 1H), 7.99-7.98 (d, 1H), 7.87-7.85 (d, 1H), 7.76-7.74 (dd, 1H), 7.47-7.46 (d, 1H), 7.32-7.31 (d, 1H), 6.82-6.80 (d, 1H), 4.17-4.14 (t, 2H), 4.03-3.99 (t, 2H), 2.15-2.05 (m, 1H), 1.15-1.11 (m, 2H), 0.86-0.82 (m, 2H). LCMS Purity: 95%, m/z=336.1 (M+1). HPLC Purity: 98%

Example 5

Preparation of 1-(4-cyclopropylpyridin-3-yl)-3-(3-(trifluoromethyl)phenyl)imidazolidin-2-one (5A)

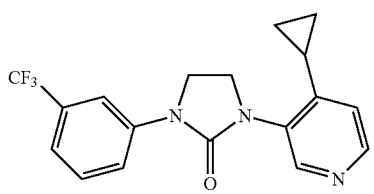

(5A)

Using analogous reagents and reaction conditions as described in Example 1 above, 1-(4-cyclopropylpyridin-3-yl)imidazolidin-2-one (I-1d: 150 mg, 0.738 mmol) was reacted with 1-bromo-3-(trifluoromethyl)benzene (831 mg, 3.69 mmol), 1,4-dioxane (10 mL), copper iodide (14.0 mg, 0.073 mmol), trans-N,N'-dimethylcyclohexane-1,2-diamine (8.4 mg, 0.073 mmol) and potassium phosphate (469.9 mg, 2.21 mmol) to afford the crude product. Purification by column chromatography on silica gel (1.5% methanol in CHCl$_3$) afforded 205 mg of the product (80% yield).

$^1$H NMR (CDCl$_3$, 400 MH$_Z$): δ 8.70-8.40 (m, 2H), 7.90-7.84 (t, 2H), 7.51-7.47 (t, 1H), 7.35-7.27 (t, 1H), 6.85 (bs, 1H), 4.13-4.08 (t, 2H), 4.03-3.99 (t, 2H), 2.07-2.03 (m, 1H), 1.16-1.11 (m, 2H), 0.86-0.82 (m, 2H). LCMS Purity: 94%, m/z=348.1 (M+1). HPLC Purity: 96%

Example 6

Preparation of 1-(benzo[b]thiophen-2-yl)-3-(4-cyclopropylpyridin-3-yl)imidazolidin-2-one (6A)

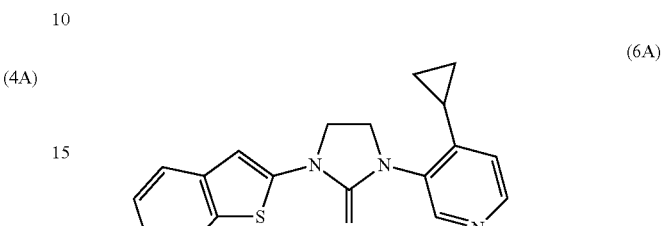

(6A)

Using analogous reagents and reaction conditions as described in Example 1 above, 1-(4-cyclopropylpyridin-3-yl)imidazolidin-2-one (I-1d: 150 mg, 0.738 mmol) was reacted with 2-bromobenzo[b]thiophene (188 mg, 0.886 mmol), 1,4-dioxane (6 mL), copper iodide (14.0 mg, 0.0739 mmol), trans-N,N'-dimethylcyclohexane-1,2-diamine (10.5 mg, 0.0739 mmol) and potassium phosphate (470 mg, 2.21 mmol) to afford the crude product. Purification by column chromatography on silica gel (0.5% methanol in CHCl$_3$) afforded 85 mg of the product (34% yield).

$^1$H NMR (CDCl$_3$, 400 MH$_Z$): δ 8.60-8.30 (m, 2H), 7.74-7.72 (d, 1H), 7.63-7.60 (d, 1H), 7.33-7.19 (m, 2H), 6.82 (s, 1H), 6.56 (s, 1H), 4.20-4.04 (m, 4H), 2.10-2.0 (m, 1H), 1.16-1.10 (m, 2H), 0.85-0.80 (m, 2H). LCMS Purity: 90%, m/z=336.1 (M+1). HPLC Purity: 95%

Example 7

Preparation of 1-(6-chloro-2-methylpyrimidin-4-yl)-3-(4-cyclopropylpyridin-3-yl)imidazolidin-2-one (7A)

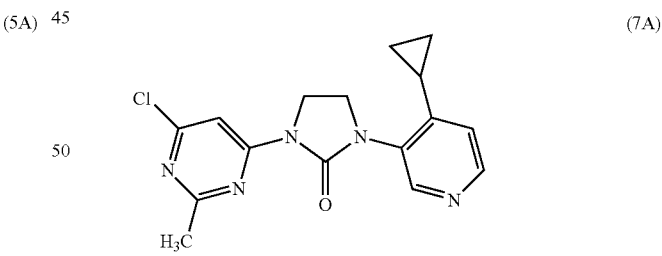

(7A)

Using analogous reagents and reaction conditions as described in Example 1 above, 1-(4-cyclopropylpyridin-3-yl)imidazolidin-2-one (I-1d: 100 mg, 0.492 mmol) was reacted with 4,6-dichloro-2-methylpyrimidine (80.2 mg, 0.492 mmol), 1,4-dioxane (5 mL), copper iodide (9.3 mg, 0.049 mmol), trans-N,N'-dimethylcyclohexane-1,2-diamine (6.9 mg, 0.049 mmol) and potassium phosphate (313 mg, 1.47 mmol) to afford the crude product. Purification by column chromatography on silica gel (1% methanol in CHCl$_3$) afforded 25 mg of the product (15% yield).

$^1$H NMR (CDCl$_3$, 400 MH$_Z$): δ 8.55-8.40 (m, 2H), 8.16 (s, 1H), 6.84 (s, 1H), 4.30-4.26 (q, 2H), 3.99-3.95 (q, 2H), 2.62

(s, 3H), 1.99-1.94 (m, 1H), 1.16-1.11 (m, 2H), 0.86-0.81 (m, 2H). LCMS Purity: 97%, m/z=330.1 (M+1). HPLC Purity: 98%

Example 8

Preparation of 1-(4-cyclopropylpyridin-3-yl)-3-(4-(trifluoromethyl)pyridin-2-yl)imidazolidin-2-one (8A)

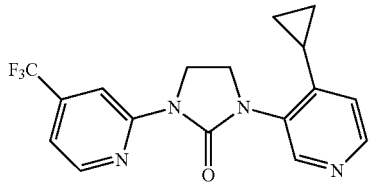

(8A)

Using analogous reagents and reaction conditions as described in Example 1 above, 1-(4-cyclopropylpyridin-3-yl)imidazolidin-2-one (I-1d: 150 mg, 0.738 mmol) was reacted with 2-bromo-4-(trifluoromethyl)pyridine (200.3 mg, 0.88 mmol), 1,4-dioxane (5 mL), copper iodide (14.03 mg, 0.073 mmol), trans-N,N'-dimethylcyclohexane-1,2-diamine (10.49 mg, 0.073 mmol) and potassium phosphate (469.9 mg, 2.21 mmol) to afford the crude product. Purification by column chromatography on silica gel (1% methanol in CHCl$_3$) afforded 182.5 mg of the product (71% yield).

$^1$H NMR (CDCl$_3$, 300 MH$_Z$): δ 8.64 (s, 1H), 8.48-8.46 (d, 2H), 7.17-7.15 (d, 2H), 6.95-6.75 (bs, 1H), 4.34-4.29 (t, 2H), 4.01-3.96 (t, 2H), 2.04-1.99 (m, 1H), 1.17-1.10 (m, 2H), 0.86-0.81 (m, 2H). LCMS Purity: 98%, m/z=349.0 (M+1). HPLC Purity: 98%

Example 9

Preparation of 1-(4-cyclopropylpyridin-3-yl)-3-(2-methoxypyridin-4-yl)imidazolidin-2-one (9A)

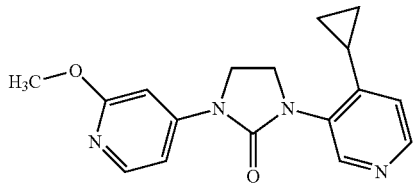

(9A)

Using analogous reagents and reaction conditions as described in Example 1 above, 1-(4-cyclopropylpyridin-3-yl)imidazolidin-2-one (I-1d: 100 mg, 0.492 mmol) was reacted with 4-bromo-2-methoxypyridine (111.1 mg, 0.591 mmol), 1,4-dioxane (5 mL), copper iodide (9.39 mg, 0.049 mmol), trans-N,N'-dimethylcyclohexane-1,2-diamine (6.98 mg, 0.049 mmol) and potassium phosphate (312.9 mg, 1.476 mmol) to afford the crude product. Purification by column chromatography on silica gel (1% methanol in CHCl$_3$) afforded 80 mg of the product (52% yield).

$^1$H NMR (CDCl$_3$, 300 MHz): δ 8.70-8.25 (m, 2H), 8.08-8.06 (d, 1H), 7.46-7.44 (dd, 1H), 6.90-6.80 (bs, 1H), 6.73 (d, 1H), 4.03-4.0 (m, 4H), 3.93 (s, 3H), 2.05-1.95 (m, 1H), 1.14-1.10 (m, 2H), 0.85-0.81 (m, 2H). LCMS Purity: 100%, m/z=311.3 (M+1). HPLC Purity: 96%

Example 10

Preparation of 1-(6-chloropyrimidin-4-yl)-3-(4-cyclopropylpyridin-3-yl)imidazolidin-2-one (10A)

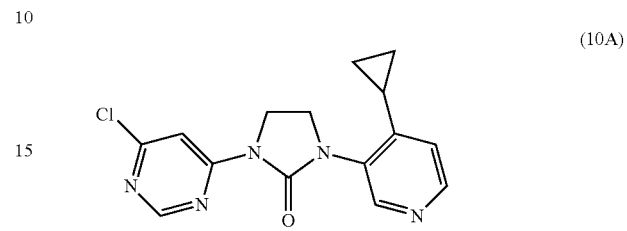

(10A)

Using analogous reagents and reaction conditions as described in Example 1 above, 1-(4-cyclopropylpyridin-3-yl)imidazolidin-2-one (I-1d: 120 mg, 0.591 mmol) was reacted with 4,6-dichloropyrimidine (88.07 mg, 0.591 mmol), 1,4-dioxane (5 mL), copper iodide (11.21 mg, 0.059 mmol), trans-N,N'-dimethylcyclohexane-1,2-diamine (8.39 mg, 0.059 mmol) and potassium phosphate (375.96 mg, 1.77 mmol) to afford the crude product. Purification by column chromatography on silica gel (0.5% methanol in CHCl$_3$) afforded 15.3 mg of the product (9% yield).

$^1$H NMR (CDCl$_3$, 300 MH$_Z$): δ 8.67 (s, 1H), 8.60-8.40 (m, 2H), 8.35 (s, 1H), 6.84 (s, 1H), 4.32-4.26 (t, 2H), 4.0-3.97 (t, 2H), 1.98-1.93 (m, 1H), 1.17-1.11 (m, 2H), 0.87-0.81 (m, 2H). LCMS Purity: 100%, m/z=316.1 (M+1). HPLC Purity: 95%

Example 11

Preparation of 1-(4-cyclopropylpyridin-3-yl)-3-(4-(trifluoromethyl)pyrimidin-2-yl)imidazolidin-2-one (11A)

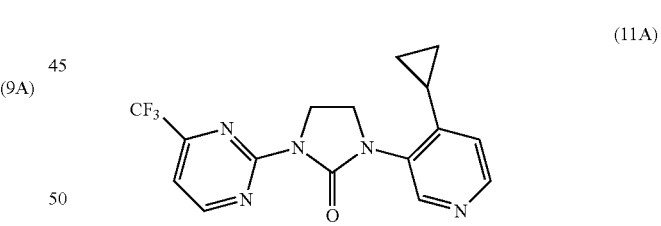

(11A)

Xantphos (23 mg, 0.049 mmol) and Pd$_2$(dba)$_3$ (22.5 mg, 0.024 mmol) were added to a solution of cesium carbonate (400 mg, 1.23 mmol) in toluene (5 mL) previously purged with nitrogen (20 minutes). The reaction mixture was purged with argon for 10 minutes, followed by the addition of, 1-(4-cyclopropylpyridin-3-yl)imidazolidin-2-one (I-1d: 100 mg, 0.492 mmol) and 2-chloro-4-(trifluoromethyl)pyrimidine (0.06 ml, 0.54 mmol). The reaction mixture was heated in seal tube at 110° C. for 16 hours. The reaction was monitored by TLC (10% methanol in chloroform). The reaction mixture was cooled, filtered and the filtrate partitioned between ethyl acetate and water. The organic layer was concentrated to yield the crude product. Purification by column chromatography on silica gel (1.5% methanol in chloroform) afforded 60 mg of the product (35% yield).

$^1$H NMR (CDCl$_3$, 400 MHz): δ 8.95-8.93 (d, 1H), 8.51 (s, 1H), 8.44-8.43 (d, 1H), 7.29-7.28 (d, 1H), 6.83-6.82 (d, 1H), 4.36-4.32 (t, 2H), 4.0-3.96 (t, 2H), 2.10-2.0 (m, 1H), 1.15-1.11 (m, 2H), 0.84-0.82 (m, 2H). LCMS Purity: 100%, m/z=350.1 (M+1). HPLC Purity: 97%

Example 12

Preparation of 1-(4-cyclopropylpyridin-3-yl)-3-(2-(trifluoromethyl)pyrimidin-4-yl)imidazolidin-2-one (12A)

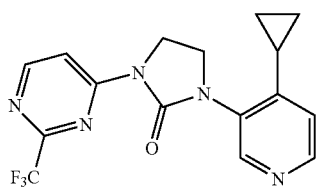

(12A)

Using analogous reagents and reaction conditions as described in Example 1 above, 1-(4-cyclopropylpyridin-3-yl)imidazolidin-2-one (I-1d: 100 mg, 0.492 mmol) was reacted with 4-chloro-2-(trifluoromethyl)pyrimidine (108 mg, 0.591 mmol), 1,4-dioxane (5 mL), copper iodide (9.3 mg, 0.049 mmol), trans-N,N'-dimethylcyclohexane-1,2-diamine (6.9 mg, 0.049 mmol) and potassium phosphate (313 mg, 1.47 mmol) to afford the crude product. Purification by column chromatography on silica gel (1% methanol in CHCl$_3$), followed by preparative HPLC afforded 20 mg of the product (12% yield).

$^1$H NMR (CDCl$_3$, 400 MHz$_Z$): δ 8.64-8.63 (d, 1H), 8.48-8.44 (m, 3H), 6.84-6.83 (d, 1H), 4.38-4.34 (t, 2H), 4.04-4.00 (t, 2H), 2.01-1.95 (m, 1H), 1.17-1.13 (m, 2H), 0.87-0.84 (m, 2H). LCMS Purity: 98%, m/z=350.1 (M+1). HPLC Purity: 99%

Example 13

Preparation of 1-(4-cyclopropylpyridin-3-yl)-3-(3-(trifluoromethyl)benzo[b]thiophen-5-yl)imidazolidin-2-one (13A)

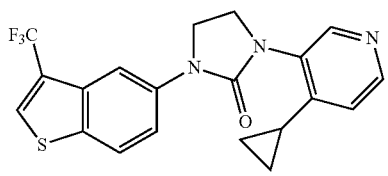

(13A)

Using analogous reagents and reaction conditions as described in Example 1 above, 1-(4-cyclopropylpyridin-3-yl)imidazolidin-2-one (I-1d: 100 mg, 0.492 mmol) was reacted with 5-bromo-3-(trifluoromethyl)benzo[b]thiophene (151 mg, 0.54 mmol), 1,4-dioxane (5 mL), copper iodide (9.3 mg, 0.049 mmol), trans-N,N'-dimethylcyclohexane-1,2-diamine (6.9 mg, 0.049 mmol) and potassium phosphate (313 mg, 1.47 mmol) to afford the crude product. Purification by column chromatography on silica gel (0.5% methanol in CHCl$_3$), followed by preparative HPLC afforded 15.4 mg of the product (8% yield).

$^1$H NMR (CDCl$_3$, 300 MHz$_Z$): δ 8.52 (s, 1H), 8.43-8.41 (d, 1H), 8.15-8.12 (dd, 1H), 7.93 (s, 1H), 7.88-7.85 (d, 1H), 7.81 (s, 1H), 6.81-6.79 (d, 1H), 4.18-4.15 (m, 2H), 4.05-4.02 (m, 2H), 2.15-2.05 (m, 1H), 1.15-1.11 (m, 2H), 0.84-0.82 (m, 2H). LCMS Purity: 98%, m/z=404.1 (M+1). HPLC Purity: 97%

Example 14

Preparation of 1-(4-cyclopropylpyridin-3-yl)-3-(2-fluorobenzo[b]thiophen-5-yl)imidazolidin-2-one (14A)

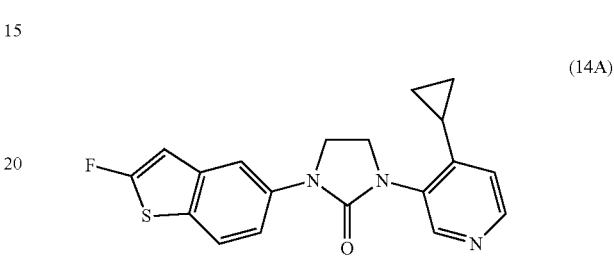

(14A)

Using analogous reagents and reaction conditions as described in step 5 of example 1,1-(4-cyclopropylpyridin-3-yl)imidazolidin-2-one (I-1d: 145 mg, 0.714 mmol) was reacted with 5-bromo-2-fluorobenzo[b]thiophene (165 mg, 0.714 mmol), 1,4-dioxane (5 mL), copper iodide (13.6 mg, 0.071 mmol), trans-N,N'-dimethylcyclohexane-1,2-diamine (10.1 mg, 0.071 mmol) and potassium phosphate (454 mg, 2.14 mmol) to afford the crude product. Purification by column chromatography on silica gel (0.5-1% methanol in CHCl$_3$), followed by preparative HPLC afforded 53 mg of the product (21% yield).

$^1$H NMR (CDCl$_3$, 300 MHz$_Z$): δ 8.50 (s, 1H), 8.42-8.40 (d, 1H), 7.86 (s, 1H), 7.63 (s, 2H), 6.81-6.79 (d, 1H), 6.69-6.68 (d, 1H), 4.14-4.09 (t, 2H), 4.02-3.96 (t, 2H), 2.11-2.03 (m, 1H), 1.16-1.09 (m, 2H), 0.88-0.82 (m, 2H). LCMS Purity: 100%, m/z=354.3 (M+1). HPLC Purity: 98%

Example 15

Preparation of 1-(4-cyclopropylpyridin-3-yl)-3-(3-methylbenzo[b]thiophen-5-yl)imidazolidin-2-one (15A)

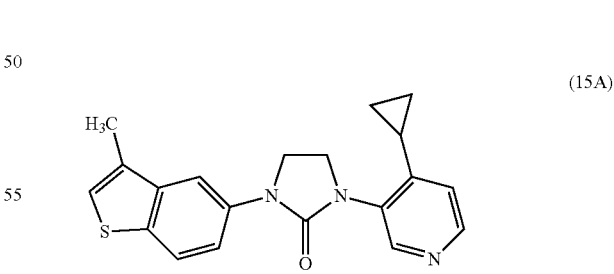

(15A)

Using analogous reagents and reaction conditions as described in Example 1 above, 1-(4-cyclopropylpyridin-3-yl)imidazolidin-2-one (I-1d: 100 mg, 0.492 mmol) was reacted with 5-bromo-3-methylbenzo[b]thiophene (122.4 mg, 0.541 mmol), 1,4-dioxane (5 mL), copper iodide (9.3 mg, 0.049 mmol), trans-N,N'-dimethylcyclohexane-1,2-diamine (5.6 mg, 0.049 mmol) and potassium phosphate (313 mg, 1.477 mmol) to afford the crude product. Purification by column chromatography on silica gel (2% methanol in CHCl₃) afforded 100 mg of the product (58% yield).

¹H NMR (CDCl₃, 400 MH$_Z$): δ 8.70-8.30 (m, 2H), 7.94-7.93 (d, 1H), 7.83-7.81 (d, 1H), 7.66-7.64 (dd, 1H), 7.09 (s, 1H), 6.81 (s, 1H), 4.19-4.15 (m, 2H), 4.03-3.99 (m, 2H), 2.43 (s, 3H), 2.12-2.08 (m, 1H), 1.15-1.10 (m, 2H), 0.85-0.81 (m, 2H). LCMS Purity: 93%, m/z=458.1 (M+1). HPLC Purity: 95%

Example 16

Preparation of 1-(benzo[b]thiophen-6-yl)-3-(4-cyclopropylpyridin-3-yl)imidazolidin-2-one (16A)

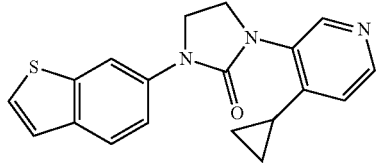

(16A)

Using analogous reagents and reaction conditions as described in Example 1 above, 1-(4-cyclopropylpyridin-3-yl)imidazolidin-2-one (I-1d: 100 mg, 0.492 mmol) was reacted with 6-bromobenzo[b]thiophene (195 mg, 0.541 mmol), 1,4-dioxane (6 mL), copper iodide (9.3 mg, 0.049 mmol), trans-N,N'-dimethylcyclohexane-1,2-diamine (6.9 mg, 0.049 mmol) and potassium phosphate (260 mg, 1.23 mmol) to afford the crude product. Purification by column chromatography on silica gel (0.5% methanol in CHCl₃) afforded 120 mg of the product (73% yield).

¹H NMR (CDCl₃, 400 MH$_Z$): δ 9.20-8.20 (m, 2H), 8.11 (d, 1H), 7.81-7.79 (d, 1H), 7.72-7.69 (dd, 1H), 7.35-7.34 (d, 1H), 7.29-7.27 (d, 1H), 7.15-6.55 (bs, 1H), 4.17-4.13 (m, 2H), 4.03-3.99 (m, 2H), 2.10-2.05 (m, 1H), 1.14-1.10 (m, 2H), 0.88-0.81 (m, 2H). LCMS Purity: 95%, m/z=336.1 (M+1). HPLC Purity: 97%

Example 17

Preparation of 1-(4-cyclopropylpyridin-3-yl)-3-(2,2-difluorobenzo[d][1,3]dioxol-5-yl)imidazolidin-2-one (17A)

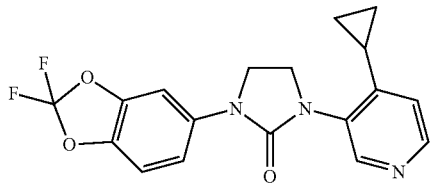

(17A)

Using analogous reagents and reaction conditions as described in Example 1 above, 1-(4-cyclopropylpyridin-3-yl)imidazolidin-2-one (I-1d: 100 mg, 0.492 mmol) was reacted with 5-bromo-2,2-difluorobenzo[d][1,3]dioxole (128.4 mg, 0.541 mmol), 1,4-dioxane (5 mL), copper iodide (9.3 mg, 0.049 mmol), trans-N,N'-dimethylcyclohexane-1,2-diamine (5.6 mg, 0.049 mmol) and potassium phosphate (313.6 mg, 1.447 mmol) to afford the crude product. Purification by column chromatography on silica gel (2.0% methanol in CHCl₃) afforded 105 mg of the product (60% yield).

¹H NMR (CDCl₃, 400 MH$_Z$): δ 8.60-8.40 (d, 2H), 7.72 (s, 1H), 7.03 (s, 2H), 6.81-6.80 (d, 1H), 4.06-3.95 (m, 4H), 2.05-2.01 (m, 1H), 1.14-1.09 (m, 2H), 0.84-0.80 (m, 2H). LCMS Purity: 95%, m/z=360.1 (M+1). HPLC Purity: 98%

Example 18

Preparation of 1-(4-cyclopropylpyridin-3-yl)-3-(3-methylbenzo[b]thiophen-6-yl)imidazolidin-2-one (18A)

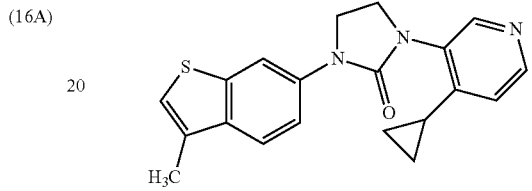

(18A)

Using analogous reagents and reaction conditions as described in Example 1 above, 1-(4-cyclopropylpyridin-3-yl)imidazolidin-2-one (I-1d: 100 mg, 0.492 mmol) was reacted with 6-bromo-3-methylbenzo[b]thiophene (112 mg, 0.492 mmol), 1,4-dioxane (5 mL), copper iodide (9.3 mg, 0.049 mmol), trans-N,N'-dimethylcyclohexane-1,2-diamine (7.0 mg, 0.049 mmol) and potassium phosphate (313.6 mg, 1.447 mmol) to afford the crude product. Purification by column chromatography on silica gel (2.0% methanol in CHCl₃) afforded 45 mg of the product (26% yield).

¹H NMR (CDCl₃, 400 MH$_Z$): δ 8.60-8.40 (m, 2H), 8.05 (d, 1H), 7.76-7.74 (m, 1H), 7.69-7.67 (d, 1H), 6.97 (d, 1H), 6.82 (bs, 1H), 4.20-4.10 (m, 2H), 4.05-3.95 (m, 2H), 2.43 (s, 3H), 2.15-2.05 (m, 1H), 1.15-1.10 (m, 2H), 0.85-0.82 (m, 2H). LCMS Purity: 100%, m/z=350.1 (M+1). HPLC Purity: 98%

Example 19

Preparation of 1-(4-cyclopropylpyridin-3-yl)-3-(3-methylbenzofuran-5-yl)imidazolidin-2-one (19A)

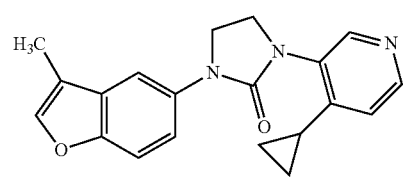

(19A)

Using analogous reagents and reaction conditions as described in Example 1 above, 1-(4-cyclopropylpyridin-3-yl)imidazolidin-2-one (I-1d: 100 mg, 0.492 mmol) was reacted with 5-bromo-3-methylbenzofuran (125 mg, 0.5904 mmol), 1,4-dioxane (4 mL), copper iodide (10 mg, 0.0492 mmol), trans-N,N'-dimethylcyclohexane-1,2-diamine (7.0 mg, 0.0492 mmol) and potassium phosphate (313 mg, 1.476 mmol) to afford the crude product. Purification by column chromatography on silica gel (1.0% methanol in CHCl₃) afforded 69 mg of the product (42% yield).

$^1$H NMR (CDCl$_3$, 300 MH$_z$): δ 8.80-8.30 (m, 2H), 7.76 (s, 1H), 7.55-7.30 (m, 2H), 6.90-6.70 (bs, 1H), 4.13-4.10 (t, 2H), 4.01-3.96 (t, 2H), 2.22 (s, 3H), 2.15-2.05 (m, 1H), 1.20-1.10 (m, 2H), 0.92-0.80 (m, 2H). LCMS Purity: 91%, m/z=334.1 (M+1). HPLC Purity: 95%

Example 20

Preparation of 1-(2-chlorobenzo[b]thiophen-5-yl)-3-(4-cyclopropylpyridin-3-yl)imidazolidin-2-one (20A)

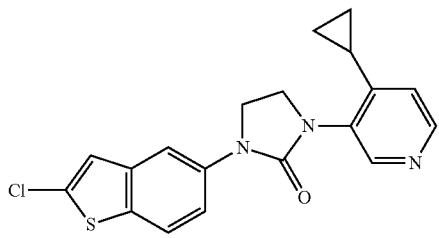

(20A)

Preparation of Intermediate
5-Bromo-2-chloro-benzo[b]thiophene (I-20a)

n-Butyl lithium (0.64 ml, 1.2 mmol) was added drop wise to a solution of diisopropyl amine (0.25 mL, 1.5 mmol) in dry THF at −78° C. under nitrogen atmosphere over a period of 5 minutes. The reaction mixture was stirred at −20° C. for 30 minutes. To this was added 5-bromo-benzo[b]thiophene (200 mg, 0.938 mmol) in dry THF at −78° C., continued stirring for a further 30 minutes at −78° C., followed by the addition of N-chlorosuccinamide (225 mg, 1.68 mmol) in dry THF at −78° C. The resulting mixture was stirred at room temperature for 2 hours. The reaction was monitored by TLC (100% hexane). The reaction mixture was partitioned between ethyl acetate and saturated ammonium chloride. The organic layer was dried over sodium sulfate and concentrated to afford the crude product. Purification by column chromatography on silica gel (100% hexane) afforded 70 mg of the product (30% yield).

$^1$H NMR (CDCl$_3$, 300 MH$_z$): δ7.815-7.811 (d, 1H), 7.57-7.55 (d, 1H), 7.44-7.41 (dd, 1H), 7.12 (s, 1H).

Preparation of the title compound 1-(2-chlorobenzo[b]thiophen-5-yl)-3-(4-cyclopropylpyridin-3-yl)imidazolidin-2-one (20A)

Using analogous reagents and reaction conditions as described in Example 1 above, 1-(4-cyclopropylpyridin-3-yl)imidazolidin-2-one (I-1d: 100 mg, 0.491 mmol) was reacted with 5-bromo-2-chloro-benzo[b]thiophene- (134.6 mg, 0.541 mmol), copper iodide (9.3 mg, 0.049 mmol), trans-N,N'-dimethylcyclohexane-1,2-diamine (7.0 mg, 0.0491 mmol), potassium phosphate (260.9 mg, 1.23 mmol) and 1,4-dioxane (5 mL to yield the crude product. Purification by column chromatography on silica gel (1.5% methanol in DCM), afforded 60.0 mg of the product (33% yield)

$^1$H NMR (CDCl3, 400 MHZ): δ 8.90 (s, 1H), 8.52-8.51 (d, 1H), 7.82-7.81 (d, 1H), 7.71-7.68 (d, 1H), 7.61-7.58 (dd, 1H), 7.17-7.15 (t, 2H), 4.19-4.08 (m, 4H), 2.34-2.29 (m, 1H), 1.50-1.45 (m, 2H), 1.11-1.06 (m, 2H). LCMS Purity: 92%, m/z=370.0 (M+1). HPLC Purity: 94%

Example 21

Preparation of 1-(4-cyclopropylpyridin-3-yl)-3-(2,3-dihydro-1H-inden-5-yl)imidazolidin-2-one (21A)

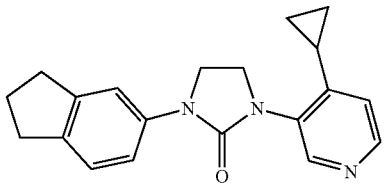

(21A)

Using analogous reagents and reaction conditions as described in Example 1 above, 1-(4-cyclopropylpyridin-3-yl)imidazolidin-2-one (I-1d: 100 mg, 0.492 mmol) was reacted with 5-bromo-2,3-dihydro-1H-indene (132 mg, 0.5418 mmol), 1,4-dioxane (4 mL), copper iodide (9.5 mg, 0.0492 mmol), trans-N,N'-dimethylcyclohexane-1,2-diamine (7.0 mg, 0.0492 mmol) and potassium phosphate (261 mg, 1.231 mmol) to afford the crude product. Purification by column chromatography on silica gel (1.5% methanol in CHCl$_3$) afforded 12 mg of the product (8% yield).

$^1$H NMR (CDCl$_3$, 300 MH$_z$): δ 8.01-7.97 (d, 1H), 7.54 (s, 1H), 7.34-6.90 (m, 3H), 6.83-6.81 (d, 1H), 4.10-3.85 (m, 4H), 3.0-2.8 (m, 4H), 2.15-1.95 (m, 3H), 1.15-1.05 (m, 2H), 0.85-0.75 (m, 2H). LCMS Purity: 95%, m/z=320.1 (M+1). HPLC Purity: 97%

Example 22

Preparation of 1-(4-cyclopropylpyridin-3-yl)-3-(5-fluorobenzo[b]thiophen-2-yl)imidazolidin-2-one (22A)

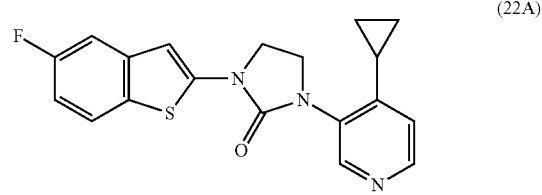 [SMILES: O=C1N(c2cc3cc(F)ccc3s2)CCN1c1cnccc1C1CC1]

(22A)

Using analogous reagents and reaction conditions as described in Example 1 above, 1-(4-cyclopropylpyridin-3-yl)imidazolidin-2-one (I-1d: 100 mg, 0.4926 mmol) was reacted with 2-bromo-5-fluorobenzo[b]thiophene (125 mg, 0.5418 mmol), 1,4-dioxane (4 mL), copper iodide (9.3 mg, 0.0492 mmol), trans-N,N'-dimethylcyclohexane-1,2-diamine (7.0 mg, 0.0492 mmol) and potassium phosphate (261 mg, 1.231 mmol) to afford the crude product. Purification by column chromatography on silica gel (0.5% methanol in CHCl₃) afforded 85 mg of the product (49% yield).

$^1$H NMR (CDCl₃, 300 MH$_Z$): δ 8.55-8.40 (m, 2H), 7.70-7.60 (m, 1H), 7.30-7.20 (m, 1H), 7.0-6.90 (m, 1H), 6.85-6.75 (d, 1H), 6.50 (s, 1H), 4.20-4.0 (m, 4H), 2.10-1.95 (m, 1H), 1.20-1.10 (m, 2H), 0.90-0.82 (m, 2H). LCMS Purity: 98%, m/z=354.1 (M+1), HPLC Purity: 93%

Example 23

Preparation of 1-(4-cyclopropylpyridin-3-yl)-3-(3-(trifluoromethyl)benzo[b]thiophen-6-yl)imidazolidin-2-one (23A)

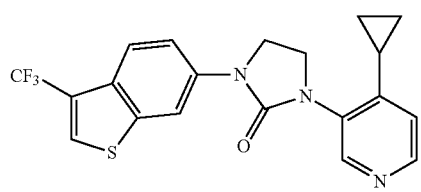

(23A)

Using analogous reagents and reaction conditions as described in Example 1 above, 1-(4-cyclopropylpyridin-3-yl)imidazolidin-2-one (I-1d: 170 mg, 0.837 mmol) was reacted with 6-bromo-3-(trifluoromethyl)benzo[b]thiophene (259 mg, 0.921 mmol), 1,4-dioxane (8 mL), copper iodide (15.9 mg, 0.083 mmol), trans-N,N'-dimethylcyclohexane-1,2-diamine (11.9 mg, 0.083 mmol) and potassium phosphate (533 mg, 2.51 mmol) to afford the crude product. Purification by column chromatography on silica gel (0.4% methanol in CHCl₃) afforded 15 mg of the product (4% yield).

$^1$H NMR (CDCl₃, 300 MH$_Z$): δ 8.70-8.40 (m, 2H), 8.29-8.28 (d, 1H), 7.9-7.89 (d, 1H), 7.79 (s, 1H), 7.70-7.66 (dd, 1H), 6.84-6.80 (bs, 1H), 4.2-4.13 (m, 2H), 4.04-3.99 (m, 2H), 2.10-2.05 (m, 1H), 1.16-1.09 (m, 2H), 0.86-0.82 (m, 2H). LCMS Purity: 95%, m/z=404.1 (M+1). HPLC Purity: 95%

Example 24

Preparation of 1-(4-Cyclopropyl-pyridin-3-yl)-3-(2-fluoro-3-methyl-benzo[b]thiophen-5-yl)-imidazolidin-2-one (24A)

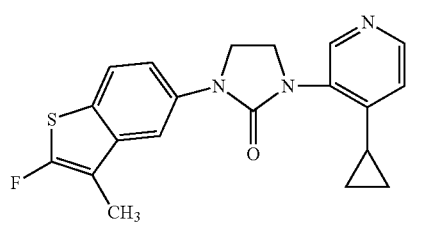

(24A)

Preparation of Intermediate 1-(4-Bromo-phenylsulfanyl)-propan-2-one (I-24a)

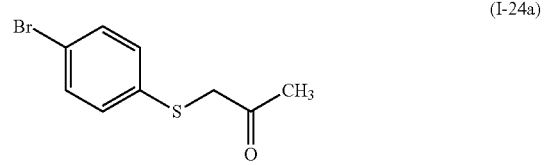

(I-24a)

1-Chloro-propan-2-one (1.0 g, 11.63 mmol) and potassium carbonate (2.9 g, 21.15 mmol) were added to a solution of 4-bromo-benzenethiol (2.0 g, 10.58 mmol) in DMF (5.0 mL) at 0° C. The resulting mixture was stirred at room temperature overnight. The reaction was monitored by TLC (100% hexane). The reaction mixture quenched with ice and extracted with ethyl acetate. The organic layer was dried over sodium sulfate and concentrated to yield the crude product. Purification by column chromatography on silica gel (2% methanol in chloroform) afforded 2.0 g of the product (80% yield).

$^1$H NMR (CDCl₃, 300 MH$_Z$): δ 7.44-7.4 (d, 2H), 7.22-7.16 (d, 2H), 3.6 (s, 2H), 2.25 (s, 3H).

Preparation of Intermediate 5-Bromo-3-methyl-benzo[b]thiophene (I-24b)

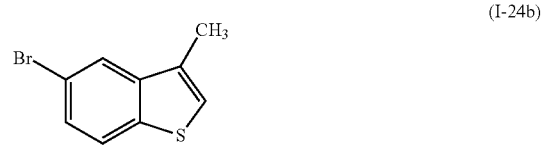

(I-24b)

Polyphosphoric acid (7 g) was added to a solution of 1-(4-bromo-phenylsulfanyl)-propan-2-one (I-24a: 2.0 g, 8.163 mmol) in toluene (10 mL) and the resulting mixture was heated to 100° C. for 5 hours. The reaction was monitored by TLC (100% hexane). The reaction mixture was cooled to room temperature, quenched with ice, basified with potassium carbonate (pH~8) and extracted with ethyl acetate. The organic layer was concentrated to yield the crude product. Purification by column chromatography on silica gel (100% hexane) afforded 1.2 g of product (66% yield)

$^1$H NMR (CDCl₃, 300 MH$_Z$): δ 7.856-7.85 (d, 1H), 7.72-7.69 (d, 1H), 7.45-7.41 (dd, 1H), 7.11 (s, 1H), 2.4 (s, 3H).

Preparation of Intermediate 5-Bromo-2-fluoro-3-methyl-benzo[b]thiophene (I-24c)

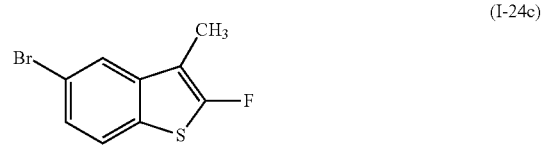

(I-24c)

Using analogous reaction condition and workup as described in Example 20 above from the preparation of I-20a, 5-bromo-3-methyl-benzo[b]thiophene (I-24b: 500 mg, 2.192 mmol) in dry THF was reacted with N-fluoro benzene sulfonimide (1.2 g, 3.94 mmol), diisopropyl amine (266.2 mg, 2.6315 mmol), n-butyl lithium (1.3 mL, 2.6315 mmol) to afford crude product. Purification by column chromatography on silica gel (hexane) afforded 120 mg of the product (22% yield).

$^1$H NMR (CDCl$_3$, 300 MHz): δ 7.72-7.68 (d, 1H), 7.54-7.5 (d, 1H), 7.44-7.39 (dd, 1H), 2.11 (s, 3H).

Preparation of the title compound 1-(4-Cyclopropyl-pyridin-3-yl)-3-(2-fluoro-3-methyl-benzo[b]thiophen-5-yl)-imidazolidin-2-one (24A)

Using analogous reagents and reaction conditions as described in Example 1 above, 1-(4-cyclopropyl-pyridin-3-yl)-imidazolidin-2-one (I-1d: 100 mg, 0.4926 mmol) was reacted with 5-bromo-2-fluoro-3-methyl-benzo[b]thiophene (I-24c: 120 mg, 0.4926 mmol), copper iodide (9.3 mg, 0.04926 mmol), trans-N,N'-dimethylcyclohexane-1,2-diamine (7.0 mg, 0.04926 mmol), potassium phosphate (313 mg, 1.4778 mmol) and 1,4-dioxane (5 ml) to afford the crude product. Purification by column chromatography on silica gel (2% methanol in chloroform) afforded 120 mg of product (66% yield).

$^1$H NMR (CDCl$_3$, 400 MHz): δ 8.70-8.30 (m, 2H), 7.88-7.87 (d, 1H), 7.63-7.61 (d, 1H), 7.54-7.52 (dd, 1H), 6.81 (s, 1H), 4.16-4.12 (m, 2H), 4.02-3.98 (m, 2H), 2.25 (s, 3H), 2.12-2.05 (m, 1H), 1.13-1.10 (m, 2H), 0.85-0.81 (m, 2H). LCMS Purity: 96%, m/z=368.1 (M+1). HPLC Purity: 97%

Example 25

Preparation of 1-(4-cyclopropyl-pyridin-3-yl)-3-(2-fluoro-benzo(b)thiophen-6-yl)-imidazolidin-2-one (25A)

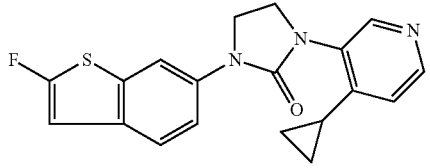

(25A)

Preparation of Intermediate 6-Bromo-benzo[b]thiophene-2-carboxylic acid methyl ester (I-25a)

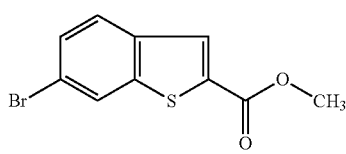

(I-25a)

TEA (1.29 g, 12.85 mmol) and mercapto-acetic acid methyl ester (1.14 g, 10.83 mmol) were added to acetonitrile (50 mL) previously purged with argon (10 minute). This was followed by the addition of 4-bromo-2-fluoro-benzaldehyde (2 g, 9.852 mmol) and the resulting mixture was heated to reflux at 85° C. overnight. The reaction was monitored by TLC (20% ethyl acetate in hexane). The reaction mixture was cooled, concentrated, basified with 10% NaOH solution and extracted with ethyl acetate to afford the crude product. Purification by column chromatography on silica gel (5% ethyl acetate in hexane) afforded 2.4 g of the product (90% yield).

$^1$H NMR (CDCl$_3$, 300 MHz): δ8.18-8.0 (dd, 2H), 7.8-7.7 (d, 1H), 7.65-7.59 (dd, 1H), 4.1-4.0 (s, 3H).

Preparation of Intermediate 6-Bromo-benzo[b]thiophene-2-carboxylic acid (I-25b)

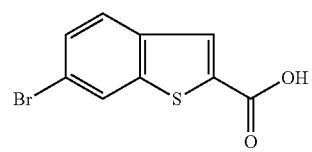

(I-25b)

LiOH.H$_2$O (1.85 g, 44 mmol) and water (20 mL) were added to a stirred solution of 6-bromo-benzo[b]thiophene-2-carboxylic acid methyl ester (I-25a: 2.4 g, 8.85 mmol) in THF (25 mL) at room temperature. The resulting mixture was stirred at room temperature for 2 hours. The reaction was monitored by TLC (100% ethyl acetate). The reaction mixture was concentrated, acidified with 2N HCl, filtered and the residue was washed with n-hexane to afford 1.9 g of the product (84% yield).

$^1$H NMR (DMSO-D$_6$, 300 MHz): δ14.0-14.03 (b, 1H), 8.4-8.39 (d, 1H), 8.28-8.1 (d, 1H), 8.18-8.0 (d, 1H), 7.78-7.62 (dd, 1H). LCMS Purity: 99%, m/z=255.9 (M+1)

Preparation of Intermediate 6-Bromo-benzo[b]thiophene (I-25c)

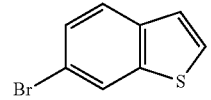

(I-25c)

DBU (1.21 g, 8.00 mmol) was added to a stirred solution of 6-bromo-benzo[b]thiophene-2-carboxylic acid (I-25b: 2.4 g, 8.85 mmol) in DMA (4 mL) at room temperature and the resulting mixture was heated in microwave at 200° C. for 1 hour. The reaction was monitored by TLC (50% ethyl acetate in hexane). The reaction mixture was acidified with 1N HCl and extracted with ethyl acetate. The organic layer was concentrated and purified by column chromatography on silica gel (100% hexane) to afford 320 mg of the product (78% yield).

$^1$H NMR (CDCl$_3$, 300 MHz): δ 8.18-8.0 (d, 1H), 7.7-7.6 (d, 1H), 7.5-7.59 (d, 1H), 7.59-7.42 (d, 1H), 7.3-7.29 (d, 1H).

Preparation of Intermediate
6-Bromo-2-fluoro-benzo[b]thiophene (I-25d)

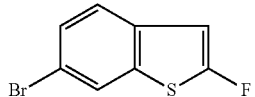
(I-25d)

Using analogous reaction condition and reagents as described Example 20 for the preparation of I-20a, 6-bromo-benzo[b]thiophene (I-25c: 0.5 g, 2.347 mmol) in dry THF was reacted with N-fluorobenzenesulfonimide (1.33 g, 4.22 mmol), n-butyl lithium (1.76 ml, 3.52 mmol), diisopropyl amine (0.57 ml, 3.99 mmol) to afford crude product. Purification by column chromatography on silica gel (100% hexane) afforded 176 mg of the product (33% yield).

$^1$H NMR (CDCl$_3$, 300 MH$_z$): δ 7.97-7.82 (d, 1H), 7.56-7.52 (dd, 2H), 6.5-6.3 (d, 1H).

Preparation of the title compound 1-(4-cyclopropyl-pyridin-3-yl)-3-(2-fluoro-benzo(b)thiophene-6-yl)-imidazolidin-2-one (25A)

Using analogous reagents and reaction conditions as described in Example 1 above, 1-(4-cyclopropylpyridin-3-yl)imidazolidin-2-one (I-1d: 150 mg, 0.738 mmol) was reacted with 6-Bromo-2-fluoro-benzo[b]thiophene (I-25d: 170.6 mg, 0.738 mmol), copper iodide (14.2, 0.071 mmol), trans-N,N'-dimethylcyclohexane-1,2-diamine (10.2 mg, 0.071 mmol), potassium phosphate (469.9 mg, 2.21 mmol) and 1,4-dioxane (5 mL) to afford the crude product. Purification by column chromatography on silica gel (1% methanol in CHCl$_3$), followed by preparative HPLC afforded 11.6 mg of the product (4% yield).

$^1$H NMR (CDCl$_3$, 400 MH$_z$): δ 8.51 (s, 1H), 8.42-8.41 (d, 1H), 8.04-8.03 (d, 1H), 7.61-7.54 (m, 2H), 6.81-6.80 (d, 1H), 6.66-6.65 (d, 1H), 4.14-4.10 (m, 2H), 4.02-3.97 (m, 2H), 2.11-2.04 (m, 1H), 1.21-1.10 (m, 2H), 0.88-0.81 (m, 2H). LCMS Purity: 99%, m/z=354.1 (M+1). HPLC Purity: 91%

Example 26

Preparation of 1-(4-cyclopropyl-pyridin-3-yl)-3-(4-fluoro-benzo[b]thiophen-6-yl)-imidazolidin-2-one (26A)

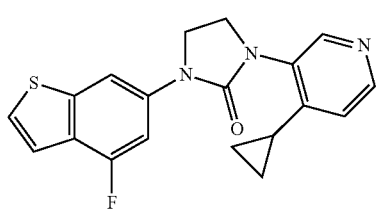
(26A)

Preparation of Intermediate
4-Bromo-2,6-difluoro-benzaldehyde (I-26a)

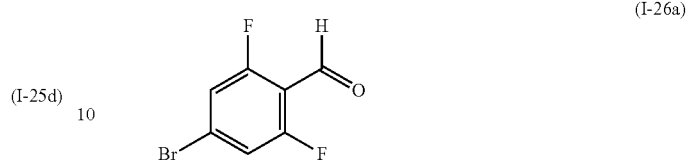
(I-26a)

Using analogous reaction condition and reagents as described in Example 20 for the preparation of I-20a above, 1-bromo-3,5-difluoro-benzene (2 g, 2.10.36 mmol) in THF was reacted with DMF (1.43 g, 19.68 mmol), n-butyl lithium (1.56 ml, 12.4 mmol) and diisopropyl amine (0.57 mL, 15.5 mmol) to afford crude product. Purification by column chromatography on silica gel (2% ethyl acetate in hexane) afforded 1.35 g of the product (61% yield).

$^1$H NMR (CDCl$_3$, 300 MH$_z$): δ11.5-11.0 (s, 1H), 7.4-7.2 (dd, 2H).

Preparation of intermediate
6-Bromo-4-fluoro-benzo[b]thiophene-2-carboxylic acid methyl ester (I-26b)

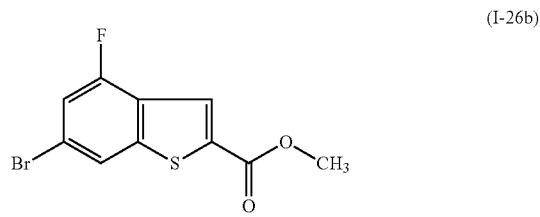
(I-26b)

Using analogous reaction condition and reagents as described in Example 25 for the preparation of I-25a, 4-bromo-2,6-difluoro-benzaldehyde (I-26a: 2.8 g, 12.8 mmol) was reacted with TEA (1.66 g, 16.47 mmol), mercapto-acetic acid methyl ester (1.47 g, 13.83 mmol) and acetonitrile (50 mL) to afford crude product. Purification by column chromatography on silica gel (2% ethyl acetate in hexane) afforded 2.3 g of the product (64% yield).

$^1$H NMR (CDCl$_3$, 400 MH$_z$): δ 8.098 (d, 1H), 7.80 (s, 1H), 7.26-7.23 (m, 1H), 3.96 (s, 3H).

Preparation of intermediate
6-Bromo-4-fluoro-benzo[b]thiophene-2-carboxylic acid (I-26c)

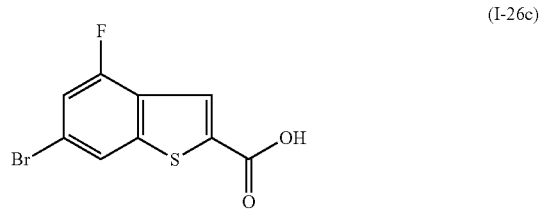 [SMILES: O=C(O)c1cc2c(F)cc(Br)cc2s1]
(I-26c)

Using analogous reagents and reaction conditions as described in Example 25 for the preparation of I-25b above, 6-bromo-4-fluoro-benzo[b]thiophene-2-carboxylic acid methyl ester (I-26b: 2.3 g, 7.85 mmol) in THF (25 mL) was hydrolyzed with LiOH (1.65 g, 39.38 mmol) and water (20 mL) to afford 1.9 g of the product (83% yield).

$^1$H NMR (DMSO-D$_6$, 300 MH$_Z$): δ 14.0-14.03 (b, 1H), 8.38-8.32 (d, 1H), 8.18-8.0 (s, 1H), 7.7-7.6 (dd, 1H).

Preparation of intermediate
6-Bromo-4-fluoro-benzo[b]thiophene (I-26d)

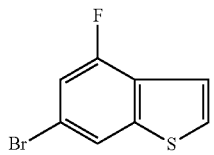

(I-26d)

Using analogous reaction condition and reagents as described in Example 25 for the preparation of I-25c above, 6-bromo-4-fluoro-benzo[b]thiophene-2-carboxylic acid (I-26c: 1.8 g, 6.47 mmol) in DMA (4 mL) and DBU (4.0 g, 26.54 mmol) were heated in microwave to afford the crude product. Purification by column chromatography on silica gel (100% hexane) afforded 1.45 g of the product (97% yield).

$^1$H NMR (CDCl$_3$, 300 MH$_Z$): δ 7.9-7.8 (d, 1H), 7.5-7.48 (dd, 2H), 7.3-7.22 (d, 1H).

Preparation of the title compound 1-(4-cyclopropyl-pyridin-3-yl)-3-(4-fluoro-benzo[b]thiophen-6-yl)-imidazolidin-2-one (26A)

Using analogous reagents and reaction conditions as described in Example 1 above, 1-(4-cyclopropylpyridin-3-yl) imidazolidin-2-one (I-1d: 120 mg, 0.591 mmol) was reacted with 6-bromo-4-fluoro-benzo[b]thiophene (I-26d: 163.6 mg, 0.738 mmol), copper iodide (11.2 mg, 0.059 mmol), trans-N, N'-dimethylcyclohexane-1,2-diamine (8.9 mg, 0.0591 mmol), potassium phosphate (375.9 mg, 1.7 mmol) and 1,4-dioxane (5 mL). Purification by column chromatography on silica gel (0.3% methanol in CHCl$_3$) afforded 51.2 mg of the product (26% yield).

$^1$H NMR (CDCl$_3$, 400 MH$_Z$): δ 9.20-8.20 (m, 2H), 7.80 (s, 1H), 7.61-7.57 (dd, 1H), 7.40-7.37 (d, 1H), 7.35-7.32 (d, 1H), 6.83-6.81 (d, 1H), 4.15-4.10 (m, 2H), 4.03-4.00 (m, 2H), 2.08-2.04 (m, 1H), 1.15-1.10 (m, 2H), 0.88-0.82 (m, 2H). LCMS Purity: 93%, m/z=354.1 (M+1). HPLC Purity: 94%

Example 27

Preparation of 1-(4-cyclopropyl-pyridin-3-yl)-3-(5-fluoro-benzo[b]thiophen-6-yl)-imidazolidin-2-one (27A)

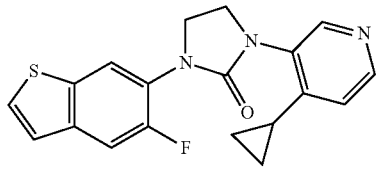

(27A)

Preparation of Intermediate
4-Bromo-2,5-difluoro-benzaldehyde (I-27a)

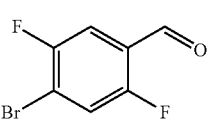

(I-27a)

n-Butyl lithium (3.6 ml, 7.7 mmol) was added drop wise to a solution of 1,4-dibromo-2,5-difluoro-benzene (2 g, 7.35 mmol) in dry ether at −78° C. under nitrogen atmosphere and the resulting mixture was stirred at −78° C. for 30 minutes. This was followed by the addition of DMF (0.85 ml, 11.03 mmol) in dry THF. The resultant was stirred at room temperature for 1 hour. The reaction was monitored by TLC (5% ethyl acetate in hexane). The reaction mixture was partitioned between ethyl acetate and saturated ammonium chloride. The organic layer was concentrated and purified by column chromatography on silica gel (2% ethyl acetate in hexane) to afford 600 mg of the product (37% yield).

$^1$H NMR (CDCl$_3$, 300 MH$_Z$): δ 10.27-10.26 (d, 1H), 7.61-7.57 (t, 1H), 7.49-7.44 (q, 1H)

Preparation of Intermediate
6-Bromo-5-fluoro-benzo[b]thiophene-2-carboxylic acid methyl ester (I-27b)

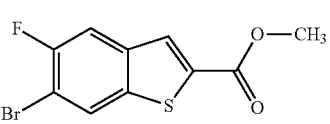

(I-27b)

Using analogous reaction condition and reagents as described in Example 25 for the preparation of I-25a above, 4-bromo-2,5-difluoro-benzaldehyde (I-27a: 1.71 g, 7.73 mmol) was reacted with TEA (1.4 mL, 10.05 mmol), mercapto-acetic acid methyl ester (920 mg, 8.51 mmol) and acetonitrile (50 mL) to afford crude product. Purification by column chromatography on silica gel (5% ethyl acetate in hexane) afforded 2.3 g of the product (Yield 64%).

$^1$H NMR (CDCl$_3$, 300 MH$_Z$): δ 8.1-7.95 (m, 2H), 7.65-7.55 (d, 1H), 3.95 (s, 3H).

Preparation of Intermediate
6-Bromo-5-fluoro-benzo[b]thiophene-2-carboxylic acid (I-27c)

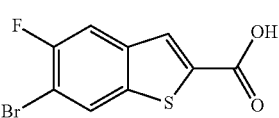

(I-27c)

Using analogous reagents and reaction conditions as described in Example 25 for the preparation of I-25b above, 6-bromo-5-fluoro-benzo[b]thiophene-2-carboxylic acid methyl ester (I-27b: 0.3 g, 10 mmol) in THF (10 mL) was hydrolyzed with LiOH (87 mg, 2.04 mmol) and water (2 mL) to afford 250 mg of the product (yield 88%)

$^1$H NMR (DMSO-D6, 300 MH$_Z$): δ 8.54-8.48 (d, 1H), 8.06-7.94 (m, 2H).

Preparation of Intermediate
6-Bromo-5-fluoro-benzo[b]thiophene (I-27d)

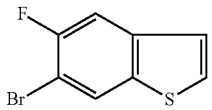
(I-27d)

Using analogous reaction condition and reagents as described in Example 25 for the preparation of I-25c above, 6-bromo-5-fluoro-benzo[b]thiophene-2-carboxylic acid (I-27c: 250 mg 0.89 mmol) in DMA (4 mL) and DBU (550 mL, 3.6 mmol) were heated in microwave to afford the crude product. Purification by column chromatography on silica gel (100% hexane) afforded 180 mg of the product (86% yield).

$^1$H NMR (CDCl$_3$, 300 MH$_Z$): δ 8.06-8.0 (d, 1H), 7.58-7.48 (t, 2H), 7.28-7.24 (d, 1H)

Preparation of the title compound 1-(4-cyclopropyl-pyridin-3-yl)-3-(5-fluoro-benzo[b]thiophen-6-yl)-imidazolidin-2-one (27A)

Using analogous reagents and reaction conditions as described in Example 1 above, 1-(4-cyclopropylpyridin-3-yl) imidazolidin-2-one (I-1d: 100 mg, 0.491 mmol) was reacted with 6-bromo-5-fluoro-benzo[b]thiophene (I-27d: 136 mg, 0.5901 mmol), copper iodide (28 mg, 0.147 mmol), trans-N, N'-dimethylcyclohexane-1,2-diamine (21 mg, 0.147 mmol), potassium phosphate (313.9 mg, 1.7 mmol) and 1,4-dioxane (5 mL) to afford the crude product. Purification by column chromatography on silica gel (1% methanol in CHCl$_3$) afforded 80 mg of the product (46% yield).

$^1$H NMR (CDCl$_3$, 300 MH$_Z$): δ 8.85-8.20 (m, 2H), 8.10-8.0 (d, 1H), 7.60-7.48 (m, 2H), 7.32-7.20 (s, 1H), 7.0-6.8 (bs, 1H), 4.20-4.10 (m, 4H), 2.20-2.05 (m, 1H), 1.20-1.10 (m, 2H), 0.88-0.82 (m, 2H). LCMS Purity: 99%, m/z=354.0 (M+1). HPLC Purity: 96%

Example 28

Preparation of 1-(4-cyclopropylpyridin-3-yl)-3-(6-fluorobenzo[b]thiophen-5-yl)imidazolidin-2-one (28A)

(28A)

Preparation of Intermediate
5-bromo-2,4-difluorobenzaldehyde (I-28a)

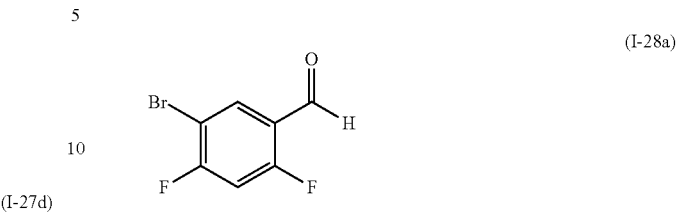
(I-28a)

Using analogous reagents and reaction conditions as described in Example 27 for the preparation of I-27a above, 1,5-dibromo-2,4-difluorobenzene (3 g, 11.07 mmol) in dry ether was reacted with DMF (1.05 mL, 14.39 mmol) and n-butyl lithium (6.08 ml, 11.56 mmol to afford the crude product. Purification by column chromatography on silica gel (2% ethyl acetate in hexane) afforded 1.5 g of the product (61% yield).

$^1$H NMR (CDCl$_3$, 300 MH$_Z$): δ 10.2 (s, 1H), 8.14-8.06 (t, 1H), 7.06-6.98 (t, 1H).

Preparation of intermediate methyl
5-bromo-6-fluorobenzo[b]thiophene-2-carboxylate (I-28b)

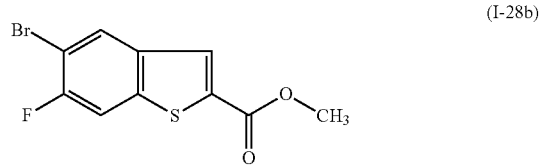
(I-28b)

Using analogous reaction condition and reagents as described in Example 25 for the preparation of I-25a above, 5-bromo-2,4-difluorobenzaldehyde (I-28a: 475 mg, 2.149 mmol) was reacted with TEA (0.748 mL, 5.372 mmol), mercapto-acetic acid methyl ester (0.211 mL, 2.36 mmol) and DMSO (4 mL) to afford crude product. Purification by column chromatography on silica gel (1.5% ethyl acetate in hexane) afforded 30 mg of the product (5% yield).

$^1$H NMR (DMSO-D$_6$, 300 MHz): δ 8.08-8.06 (d, 1H), 7.95 (s, 1H), 7.62-7.59 (d, 1H), 3.95 (s, 1H).

Preparation of Intermediate
5-bromo-6-fluorobenzo[b]thiophene-2-carboxylic acid (I-28c)

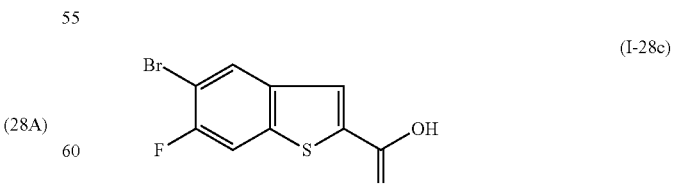
(I-28c)

Using analogous reagents and reaction conditions as described in Example 25 for the preparation of I-25b above, methyl 5-bromo-6-fluorobenzo[b]thiophene-2-carboxylate (I-28b: 0.3 g, 1.038 mmol) in THF (10 mL) was hydrolyzed with LiOH (300 mg, 1.038 mmol) and water (2 mL) to afford 240 mg of the product (85% yield)

$^1$H NMR (DMSO D$_6$, 300 MHz): δ 8.40-8.38 (d, 1H), 8.19-8.16 (m, 1H), 8.09-8.05 (m, 1H).

Preparation of Intermediate 5-bromo-6-fluorobenzo[b]thiophene (I-28d)

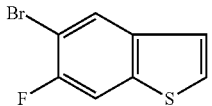
(I-28d)

Using analogous reaction condition and reagents as described in Example 25 for the preparation of I-25c above, 5-bromo-6-fluorobenzo[b]thiophene-2-carboxylic acid (I-28c: 240 mg 0.875 mmol) in DMA (4 mL) and DBU (0.523 mL, 3.503 mmol) were heated in microwave to afford the crude product. Purification by column chromatography on silica gel (100% hexane) afforded 110 mg of the product (55% yield).

$^1$H NMR (CDCl$_3$, 400 MHz): δ 8.00-7.98 (d, 1H), 7.63-7.61 (d, 1H), 7.44-7.43 (d, 1H), 7.26-7.24 (t, 1H).

Preparation of title compound 1-(4-cyclopropylpyridin-3-yl)-3-(6-fluorobenzo-[b]thiophen-5-yl)imidazolidin-2-one (28A)

Using analogous reagents and reaction conditions as described in Example 1 above, 1-(4-cyclopropylpyridin-3-yl) imidazolidin-2-one (I-1d: 90 g, 0.443 mmol) was reacted with 5-bromo-6-fluorobenzo[b]thiophene (I-28d: 102 mg, 0.443 mmol), 1,4-dioxane (4 mL), copper iodide (9 mg, 0.044 mmol), trans-N,N'-dimethylcyclohexane-1,2-diamine (19 mg, 0.132 mmol) and potassium phosphate (282 mg, 1.329 mmol) to afford the crude product. Purification by preparative HPLC afforded 9 mg of the product (6% yield).

$^1$H NMR (CDCl$_3$, 300 MHz): δ 8.55 (s, 1H), 8.43-8.41 (d, 1H), 8.0-7.97 (d, 1H), 7.66-7.62 (d, 1H), 7.43-7.41 (d, 1H), 7.29-7.26 (d, 1H), 6.83-6.81 (d, 1H), 4.10-4.01 (m, 4H), 2.13-2.10 (m, 1H), 1.18-1.15 (m, 2H), 0.84-0.82 (m, 2H). LCMS Purity: 98%, m/z=354.1 (M+1). HPLC Purity: 96%

Example 29

Preparation of 1-(4-cyclopropylpyridin-3-yl)-3-(5-fluoro-3-methylbenzo[b]thiophen-6-yl)imidazolidin-2-one (29A)

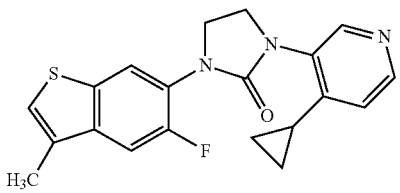
(29A)

Preparation of Intermediate 1-(3-bromo-4-fluorophenylthio) propan-2-one (I-29a)

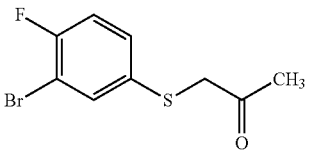
(I-29a)

Using analogous reagents and reaction conditions as described in Example 24 for the preparation of I-24a above, 3-bromo-4-fluoro-benzenethiol (2.0 g, 9.756 mmol) was reacted with 1-chloro-propan-2-one (0.86 mL, 10.73 mmol), DMF (6.0 mL), and potassium carbonate (2.69 g, 19.51 mmol) to afford crude product which was purified by column on silica gel (5% ethyl acetate in hexane) to afford 2.1 g of the product (82% yield).

$^1$H NMR (CDCl$_3$, 300 MHz): δ 7.6-7.5 (dd, 1H), 7.3-7.2 (m, 1H), 7.1-7.0 (t, 1H), 3.6 (s, 2H), 2.25 (s, 3H). LCMS Purity: 94%, m/z=320.0 (M+1)

Preparation of Intermediate 6-bromo-5-fluoro-3-methylbenzo[b]thiophene (I-29b)

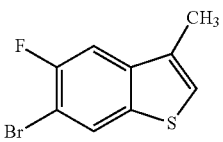
(I-29b)

Using analogous reagents and reaction conditions as described in Example 24 for the preparation of I-24b above, 1-(3-bromo-4-fluoro-phenylsulfanyl)-propan-2-one (I-29a: 2.1 g, 8.015 mmol) in toluene (10 mL) was cyclized with polyphosphoric acid (8 g) to yield crude product which was purified by column chromatography on silica gel (100% hexane) to afford 1.4 g of product (72% yield).

$^1$H NMR (CDCl$_3$, 300 MHz): δ 8.02-7.96 (d, 1H), 7.72-7.64 (q, 1H), 7.44-7.38 (d, 1H), 2.4 (s, 3H).

Preparation of the title compound 1-(4-cyclopropylpyridin-3-yl)-3-(5-fluoro-3-methylbenzo[b]thiophen-6-yl)imidazolidin-2-one (29A)

Using analogous reagents and reaction conditions as described in Example 1 above, 4-cyclopropyl-pyridin-3-yl)-imidazolidin-2-one (I-1d: 150 mg, 0.7389 mmol) was reacted with 6-bromo-5-fluoro-3-methyl-benzo[b]thiophene (I-29b: 216 mg, 0.8866 mmol), 1,4-dioxane (5 mL), copper iodide (14.07 mg, 0.0738 mmol), trans-N,N'-dimethylcyclohexane-1,2-diamine (10.4 mg, 0.0.0738 mmol) and potassium phosphate (469.9 mg, 2.2167 mmol) to afford the crude product. Purification by column chromatography on silica gel (1% methanol in chloroform), followed by preparative HPLC afforded 62 mg of the product (22% yield).

¹H NMR (CDCl₃, 400 MHz): δ 8.52 (s, 1H), 8.41-8.40 (d, 1H), 8.03-8.01 (d, 1H), 7.46-7.43 (d, 1H), 7.14 (s, 1H), 6.81-6.80 (d, 1H), 4.20-4.10 (m, 2H), 4.05-3.99 (m, 2H), 2.40 (s, 3H) 2.2-2.1 (m, 1H), 1.17-1.14 (m, 2H), 0.83-0.82 (m, 2H). LCMS Purity: 100%, m/z=368.1 (M+1). HPLC Purity: 97%

Example 30

Preparation of (1R,5S)-2-(2-chloropyridin-4-yl)-4-(4-cyclopropylpyridin-3-yl)-2,4-diazabicyclo[3.1.0]hexan-3-one (Enantiomer I: 30A-I) and (1S,5R)-2-(2-chloropyridin-4-yl)-4-(4-cyclopropylpyridin-3-yl)-2,4-diazabicyclo[3.1.0]hexan-3-one (Enantiomer II: 30A-II)

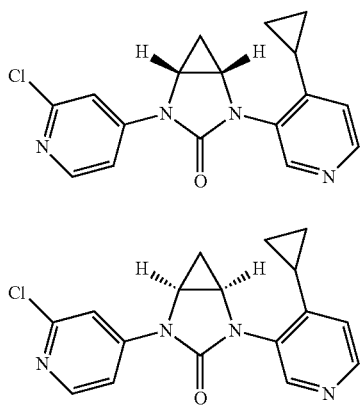

Preparation of Intermediate 4-cyclopropyl-3-iodopyridine (I-30a)

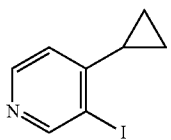

Isoamyl nitrite (2.62 gm, 22.38 mmol) was added to the stirred solution of 4-cyclopropylpyridin-3-amine (1.0 g, 7.46 mmol) in dry THF (15 mL) under argon atmosphere. This was followed by the addition of diiodomethane (3.0 mL, 22.38 mmol) and copper iodide (1.42 g, 7.46 mmol). The resulting mixture was refluxed at 80° C. for 1 hour. The reaction mixture was cooled, filtered and the filtrate was partitioned between ethyl acetate and water. The organic layer was concentrated to yield the crude product. Purification by column chromatography on silica gel (15% ethyl acetate in hexane) afforded 600 mg of the product (34% yield).

¹H NMR (CDCl₃, 400 MHz): δ 8.84 (s, 1H), 8.35-8.34 (d, 1H), 6.73-6.71 (d, 1H) 2.10-2.04 (m, 1H), 1.17-1.12 (m, 2H), 0.78-0.74 (m, 2H).

Preparation of Intermediate benzyl 4-(2-chloropyridin-4-yl)-3-oxo-2,4-diazabicyclo[3.1.0]hexane-2-carboxylate (I-30b)

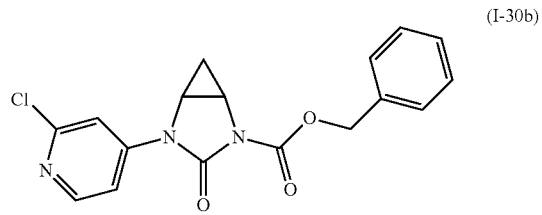 [SMILES: O=C(OCc1ccccc1)N1C(=O)N(c2ccnc(Cl)c2)C2CC21]

Using analogous reagents and reaction conditions as described in Example 1 above, benzyl 3-oxo-2,4-diazabicyclo[3.1.0]hexane-2-carboxylate (200 mg, 0.861 mmol) was reacted with 2-chloro-4-iodopyridine (227 mg, 0.947 mmol), xantphos (45 mg, 0.077 mmol), Pd₂(dba)₃ (24 mg, 0.025 mmol), cesium carbonate (421 mg, 1.29 mmol) and 1,4-dioxane (12 mL) at 100° C. for 3 hours. Purification by column chromatography on silica gel (50% ethyl acetate in hexane) afforded 220 mg of the product (75% yield).

LCMS Purity: 96%, m/z=344.0 (M+1)

Preparation of Intermediate 2-(2-chloropyridin-4-yl)-2,4-diazabicyclo[3.1.0]hexan-3-one (I-30c)

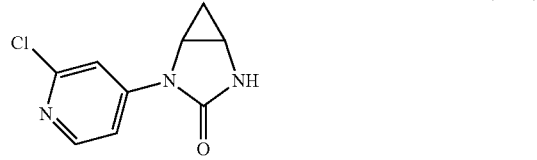

A solution of benzyl 4-(2-chloropyridin-4-yl)-3-oxo-2,4-diazabicyclo-[3.1.0]hexane-2-carboxylate (I-30b: 20.0 mg, 0.058 mmol) in 3.0 mL of 6N HCl was heated to 100° C. for 1 hour. The resulting mixture was basified with 1N NaOH. The reaction mixture was cooled and partitioned between ethyl acetate and water. The organic layer was concentrated and washed with hexane to afford 10 mg of the product (83% yield).

¹H NMR (CDCl₃, 300 MHz): δ 8.28-8.26 (d, 1H), 7.61-7.60 (t, 2H), 5.7 (s, 1H), 3.6-3.5 (m, 1H), 3.35-3.25 (m, 1H), 1.05-1.02 (q, 1H), 0.62-0.59 (q, 1H). LCMS Purity: 90%, m/z=210.0 (M+1)

Preparation of the title compound 2-(2-chloropyridin-4-yl)-4-(4-cyclopropylpyridin-3-yl)-2,4-diazabicyclo[3.1.0]hexan-3-one (racemic mixture) (30A)

Using analogous reagents and reaction conditions as described in Example 1 above, 2-(2-chloropyridin-4-yl)-2,4-diazabicyclo[3.1.0]hexan-3-one (I-30c: 90 mg, 0.43 mmol) was reacted with 4-cyclopropyl-3-iodopyridine (I-30a: 116 mg, 0.47 mmol), copper iodide (8 mg, 0.043 mmol), trans-N,N'-dimethylcyclohexane-1,2-diamine (6.1 mg, 0.043 mmol), potassium phosphate (228 mg, 1.07 mmol) and 1,4-dioxane (5 mL) to afford the crude product. Purification by column chromatography on silica gel (1.5% methanol in CHCl₃) afforded 15 mg of the product (11% yield).

¹H NMR (CDCl₃, 400 MH$_Z$): δ 8.51 (s, 1H), 8.45-8.44 (d, 1H), 8.32-8.31 (d, 1H), 7.71-7.67 (m, 2H), 6.85-6.84 (d, 1H), 3.72-3.61 (m, 2H), 2.07-2.03 (m, 1H), 1.28-1.10 (m, 3H), 0.93-0.78 (m, 3H). LCMS Purity: 97%, m/z=327.1 (M+1). HPLC Purity: 96%

The racemic mixture of 2-(2-chloropyridin-4-yl)-4-(4-cyclopropylpyridin-3-yl)-2,4-diazabicyclo[3.1.0]hexan-3-one (30A) was further separated by chiral preparative HPLC (mobile phases: A: n-hexane; B: IPA, column: CHIRALPAK AD-H (250×10 mm, 5µ), flow: 7 mL/minute, elution: isocratic (80% of A: 20% of B), diluent: IPA, approximate retention times of peaks: 15.0 minutes (peak I) and 24.0 minutes (peak II)) to obtain two pure isomers: Enantiomer I (30A-I) and Enantiomer II (30A-II).

Enantiomer I (30A-I):

¹H NMR (CDCl₃, 400 MH$_Z$): δ 8.60-8.38 (m, 2H), 8.31-8.29 (d, 1H), 7.69-7.66 (m, 2H), 6.86 (s, 1H), 3.71-3.66 (m, 1H), 3.64-3.60 (m, 1H), 2.09-2.01 (m, 1H), 1.35-1.10 (m, 3H), 0.95-0.75 (m, 3H). LCMS Purity: 100%, m/z=327.1 (M+1). HPLC Purity: 99%

Enantiomer II (30A-II):

¹H NMR (CDCl₃, 400 MH$_Z$): δ 8.60-8.40 (m, 2H), 8.31-8.29 (d, 1H), 7.69-7.66 (m, 2H), 6.85 (s, 1H), 3.71-3.59 (m, 2H), 2.08-2.01 (m, 1H), 1.24-1.09 (m, 3H), 0.92-0.77 (m, 3H). LCMS Purity: 100%, m/z=327.1 (M+1). HPLC Purity: 100%

Example 31

Preparation of (1S,5R)-2-(4-cyclopropylpyridin-3-yl)-4-(2-methoxypyridin-4-yl)-2,4-diazabicyclo [3.1.0]hexan-3-one (Enantiomer I: 31A-I), and (1R,5S)-2-(4-cyclopropylpyridin-3-yl)-4-(2-methoxypyridin-4-yl)-2,4-diazabicyclo[3.1.0]hexan-3-one (Enantiomer II: 31A-II)

(31A)

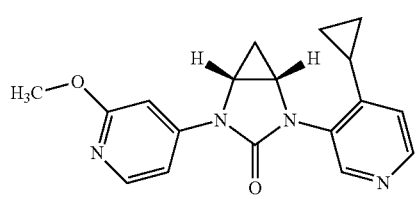

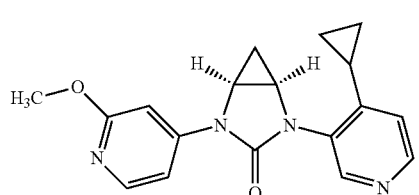

Preparation of Intermediate benzyl 4-(2-methoxypyridin-4-yl)-3-oxo-2,4-diazabicyclo[3.1.0]hexane-2-carboxylate (I-31a)

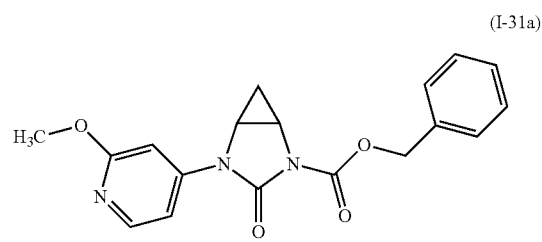 [SMILES: COc1cc(N2C(=O)N(C(=O)OCc3ccccc3)C3CC32)ccn1]

(I-31a)

Using analogous reagents and reaction conditions as described in Example 1 above, benzyl 3-oxo-2,4-diazabicyclo[3.1.0]hexane-2-carboxylate (50 mg, 0.215 mmol) was reacted with 4-bromo-2-methoxypyridine (44.5 mg, 0.237 mmol), xantphos (11 mg, 0.019 mmol), Pd₂(dba)₃ (6.0 mg, 0.006 mmol), cesium carbonate (105 mg, 0.32 mmol) and 1,4-dioxane (3.0 mL) in seal tube at 100° C. for 2.5 hours. Purification by column chromatography on silica gel (50% ethyl acetate in hexane) afforded (35% ethyl acetate in hexane) afforded 30 mg of the product (41% yield).

¹H NMR (CDCl₃, 300 MH$_Z$): δ 8.12-8.10 (d, 1H), 7.47-7.34 (m, 6H), 6.95-6.94 (d, 1H), 5.4-5.3 (q, 2H), 3.95 (s, 3H), 3.94-3.82 (m, 1H), 3.48-3.43 (m, 1H), 1.2-1.14 (q, 1H), 0.75-0.70 (m, 1H).

Preparation of Intermediate 2-(2-methoxypyridin-4-yl)-2,4-diazabicyclo[3.1.0]hexan-3-one (I-31b)

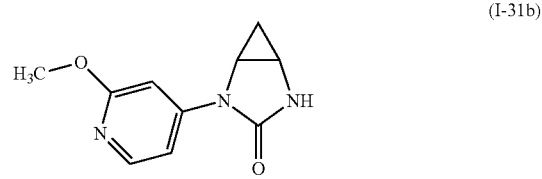

(I-31b)

Using analogous reagents and reaction conditions as described in Example 30 for the preparation of I-30c above, benzyl 4-(2-methoxypyridin-4-yl)-3-oxo-2,4-diazabicyclo [3.1.0]hexane-2-carboxylate (150.0 mg, 0.442 mmol) was treated with 10.0 mL of 6N HCl to yield the crude product. Purification by column chromatography on silica gel (1.5% methanol in chloroform) afforded 60 mg of the product (67% yield).

¹H NMR (DMSO-D₆, 300 MH$_Z$): δ 8.18 (s, 1H), 8.02-8.00 (d, 1H), 7.38-7.32 (dd, 1H), 6.957-6.951 (d, 1H).

Preparation of the title compound 2-(4-cyclopropylpyridin-3-yl)-4-(2-methoxypyridin-4-yl)-2,4-diazabicyclo[3.1.0]hexan-3-one (31A)

Using analogous reagents and reaction conditions as described in Example 1 above, 2-(2-methoxypyridin-4-yl)-2,4-diazabicyclo[3.1.0]hexan-3-one (I-31b: 140 mg, 0.682 mmol) was reacted with 4-cyclopropyl-3-iodopyridine (I-30a: 200 mg, 0.819 mmol), copper iodide (13 mg, 0.0682 mmol), trans-N,N'-dimethylcyclohexane-1,2-diamine (10 mg, 0.0682 mmol), potassium phosphate (435 mg, 2.05 mmol) and 1,4-dioxane (10 mL) to yield the crude product. Purification by column chromatography on silica gel (1.5% methanol in chloroform) afforded 120 mg of the product (57% yield).

¹H NMR (CDCl₃, 400 MHz): δ 8.51 (s, 1H), 8.42-8.41 (d, 1H), 8.11-8.09 (d, 1H), 7.47-7.46 (dd, 1H), 6.96 (d, 1H), 6.83-6.82 (d, 1H), 3.95 (s, 3H), 3.68-3.55 (m, 2H), 2.09-2.04 (m, 1H), 1.20-0.9 (m, 3H), 0.91-0.79 (m, 3H). LCMS Purity: 98%, m/z=323.1 (M+1). HPLC Purity: 99%

The racemic mixture of 2-(4-cyclopropylpyridin-3-yl)-4-(2-methoxypyridin-4-yl)-2,4-diazabicyclo[3.1.0]hexan-3-one (31A) was further separated by chiral preparative HPLC (mobile phases: A: n-hexane, B: IPA, column: CHIRALPAK AD-H (250×10 mm, 5µ), flow: 5 mL/minute, elution: isocratic (75% of A: 25% of B), diluent: ethanol, approximate retention times of peaks: 18.8 minutes (peak I) & 26.5 minutes (peak II)) to obtain two pure isomers: Enantiomer I (31A-I) and Enantiomer II (31A-II).

Enantiomer I (31A-I)

¹H NMR (CDCl₃, 400 MHz): δ 8.51 (s, 1H), 8.42-8.41 (d, 1H), 8.11-8.10 (d, 1H), 7.48-7.46 (dd, 1H), 6.96 (d, 1H), 6.83-6.82 (d, 1H), 3.95 (s, 3H), 3.68-3.58 (m, 2H), 2.10-2.04 (m, 1H), 1.25-1.07 (m, 3H), 0.91-0.79 (m, 3H). LCMS Purity: 100%, m/z=323.2 (M+1)

HPLC Purity: 97%

Enantiomer II (31A-II).

¹H NMR (CDCl₃, 400 MHz): δ 8.16-8.06 (bs, 1H), 7.48-7.46 (dd, 1H), 7.0-6.4 (bs, 1H), 3.96 (s, 3H), 3.68-3.57 (m, 2H), 2.06-2.04 (m, 1H), 1.25-1.10 (m, 3H), 0.91-0.77 (m, 3H). LCMS Purity: 100%, m/z=323.3 (M+1) HPLC Purity: 98%

Example 32

Preparation of (1S,5R)-2-(4-cyclopropylpyridin-3-yl)-4-(2-(trifluoromethyl)pyridin-4-yl)-2,4-diazabicyclo[3.1.0]hexan-3-one (Enantiomer I: 32A-I), and (1R,5S)-2-(4-cyclopropylpyridin-3-yl)-4-(2-(trifluoromethyl)pyridin-4-yl)-2,4-diazabicyclo[3.1.0]hexan-3-one (Enantiomer II: 32A-II)

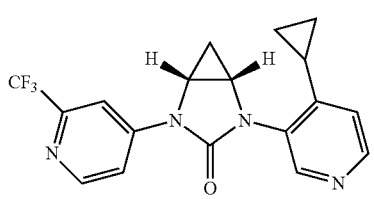

(32A-I)

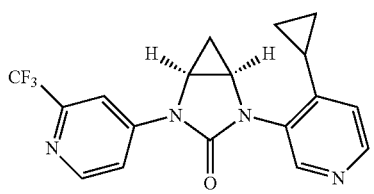

(32A-II)

Preparation of Intermediate benzyl 3-oxo-4-(2-(trifluoromethyl)pyridin-4-yl)-2,4-diazabicyclo[3.1.0]hexane-2-carboxylate (I-32a)

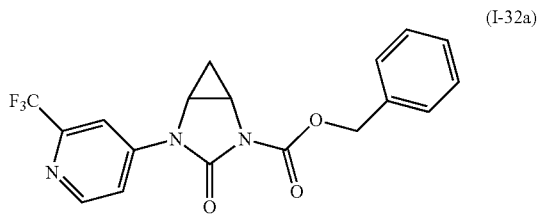 [SMILES: O=C(OCc1ccccc1)N1C(=O)N(c2ccnc(C(F)(F)F)c2)C2CC21]

(I-32a)

Using analogous reagents and reaction conditions as described in Example 1 above, benzyl 3-oxo-2,4-diazabicyclo[3.1.0]hexane-2-carboxylate (100 mg, 0.43 mmol) was heated with 4-bromo-2-(trifluoromethyl)pyridine (107 mg, 0.474 mmol), xantphos (22.36 mg, 0.038 mmol), Pd₂(dba)₃ (12 mg, 0.012 mmol), cesium carbonate (210 mg, 0.64 mmol) and 1,4-dioxane (6.0 mL) at 100° C. for 1 hour to yield the crude product. Purification by column chromatography on silica gel (35% ethyl acetate in hexane) afforded 120 mg of the product (74% yield).

¹H NMR (CDCl₃, 300 MHz): δ 8.67-8.65 (d, 1H), 8.01 (s, 1H), 7.85-7.83 (dd, 1H), 7.5-7.34 (m, 5H), 5.42-5.3 (m, 2H), 3.94-3.90 (m, 1H), 3.56-3.51 (m, 1H), 0.81-0.76 (m, 2H). LCMS Purity: 82%, m/z=378.1 (M+1)

Preparation of Intermediate 2-(2-(trifluoromethyl)pyridin-4-yl)-2,4-diazabicyclo-[3.1.0]hexan-3-one (I-32b)

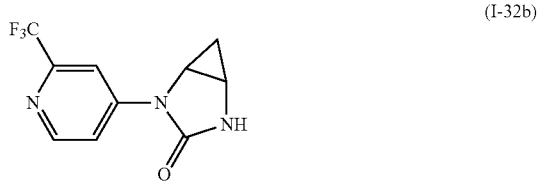 [SMILES: O=C1NC2CC2N1c1ccnc(C(F)(F)F)c1]

(I-32b)

Using analogous reagents and reaction conditions as described in Example 30 for the preparation of I-30c, benzyl 3-oxo-4-(2-(trifluoromethyl)pyridin-4-yl)-2,4-diazabicyclo[3.1.0]hexane-2-carboxylate (I-32a: 55 mg, 0.1458 mmol) was treated with 4.0 mL of 6N HCl to yield the 40 mg of the product (85% yield).

¹H NMR (CDCl₃, 300 MHz): δ 8.61-8.59 (d, 1H), 7.97-7.96 (d, 1H), 7.79-7.77 (dd, 1H), 5.74 (s, 1H), 3.61-3.57 (m, 1H), 3.35-3.28 (m, 1H), 1.1-1.05 (q, 1H), 0.64-0.61 (q, 1H).

Preparation of the title compound 2-(4-cyclopropylpyridin-3-yl)-4-(2-(trifluoromethyl)pyridin-4-yl)-2,4-diazabicyclo[3.1.0]hexan-3-one as a racemic mixture (32A)

Using analogous reagents and reaction conditions as described in Example 1 above, 2-(2-(trifluoromethyl)pyridin- 4-yl)-2,4-diazabicyclo[3.1.0]hexan-3-one (I-32b: 60 mg, 0.2469 mmol) was treated with 4-cyclopropyl-3-iodopyridine (I-30a: 66.5 mg, 0.2716 mmol), copper iodide (4.7 mg, 0.02469 mmol), trans-N,N'-dimethylcyclohexane-1,2-diamine (3.5 mg, 0.02469 mmol), potassium phosphate (157.02 mg, 0.7407 mmol), 1-4-dioxane (2 mL) was heated to reflux at 115° C. for 4 hours to yield the crude product. Purification by column chromatography on silica gel (1.5% methanol in chloroform), followed by preparative HPLC afforded 45 mg of the product (51% yield)

$^1$H NMR (CDCl$_3$, 400 MH$_Z$): δ 8.66-8.64 (d, 1H), 8.52-8.46 (d, 2H), 8.07-8.06 (d, 1H), 7.89-7.87 (dd, 1H), 6.86-6.85 (d, 1H), 3.77-3.73 (m, 1H), 3.68-3.64 (m, 1H), 2.09-2.02 (m, 1H), 1.29-1.23 (q, 1H), 1.22-1.10 (m, 2H), 0.95-0.89 (m, 2H), 0.87-0.78 (m, 1H). LCMS Purity: 100%, m/z=361.2 (M+1). HPLC Purity: 99%

The racemic mixture of 2-(4-cyclopropylpyridin-3-yl)-4-(2-(trifluoromethyl)pyridin-4-yl)-2,4-diazabicyclo[3.1.0]hexan-3-one (32A) was further separated by chiral preparative HPLC (mobile phases: A: n-hexane: B: IPA, column: CHIRALPAK AD-H (250×10 mm) 5 μm, flow: 5.0 mL/minute, elution: isocratic (80% of A: 20% of B), diluent: IPA, approximate retention times of peaks: 13.0 minutes (peak I) & 21.0 minutes (peak II)) to obtain two pure isomers: Enantiomer I (32A-I) and Enantiomer II (32A-II).

Enantiomer I (32A-I):

$^1$H NMR (CDCl$_3$, 400 MH$_Z$): δ 8.65-8.64 (d, 1H), 8.51 (s, 1H), 8.45-8.44 (d, 1H), 8.06 (s, 1H), 7.89-7.87 (d, 1H), 6.85-6.84 (d, 1H), 3.76-3.64 (m, 2H), 2.06-2.03 (m, 1H), 1.35-1.10 (m, 3H), 0.95-0.75 (m, 3H). LCMS Purity: 100%, m/z=361.1 (M+1). HPLC Purity: 100%

Enantiomer II (32A-II):

$^1$H NMR (CDCl$_3$, 400 MH$_Z$): δ 8.65-8.64 (d, 1H), 8.51 (s, 1H), 8.45-8.44 (d, 1H), 8.06 (s, 1H), 7.89-7.87 (d, 1H), 6.85-6.84 (d, 1H), 3.76-3.64 (m, 2H), 2.06-2.03 (m, 1H), 1.35-1.10 (m, 3H), 0.95-0.75 (m, 3H). LCMS Purity: 100%, m/z=361.2 (M+1). HPLC Purity: 99%

Example 33

Preparation of 1-(2-chloro-pyridin-4-yl)-3-[4-(1-hydroxy-cyclobutyl)-pyridin-3-yl]-imidazolidin-2-one (33A)

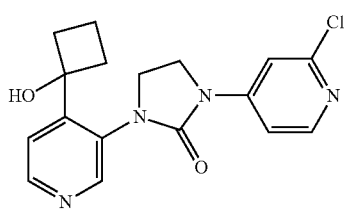

(33A)

Preparation of Intermediate 1-(2-chloroethyl)-3-(2-chloro-pyridin-4-yl)urea (I-34a)

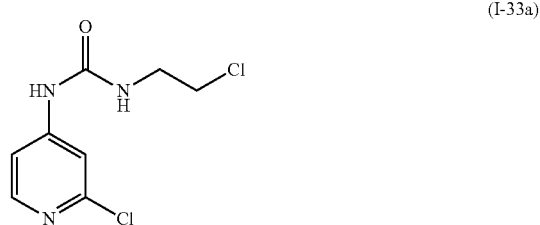 [SMILES: O=C(NCCCl)Nc1ccnc(Cl)c1]

(I-33a)

Using analogous reagents and reaction conditions as described in Example 1 above, 4-amino-2-chloro pyridine (3.0 g, 23.33 mmol) in toluene (30 mL) was reacted with 1-chloro-2-isocyanatoethane (3.69 g, 350 mmol) and purified by column chromatography on silica gel (1.5% methanol in DCM) to afford 3.3 g of the product (61% yield).

$^1$H NMR (CDCl$_3$, 300 MH$_Z$): δ 8.50 (s, 1H), 8.10 (d, 1H), 7.50 (d, 1H), 7.30-7.20 (m, 1H), 6.1 (bs, 1H), 3.70-3.60 (m, 4H).

Preparation of Intermediate 1-(2-chloro-pyridin-4-yl)imidazolidin-2-one (I-33b)

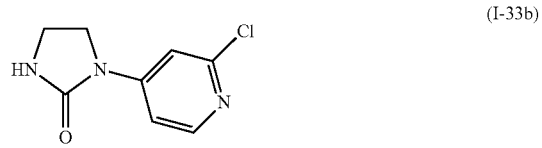 [SMILES: O=C1NCCN1c1ccnc(Cl)c1]

(I-33b)

Using analogous reagents and reaction conditions as described in Example 1 above, 1-(2-chloroethyl)-3-(2-chloro-pyridin-4-yl)urea (I-33a: 7.0 g, 30.042 mmol) in dry THF (40 mL) was reacted with 60% NaH (1.08 g, 45.06 mmol) in dry THF (30 mL) to afford the crude product. Purification by column chromatography on silica gel (1% methanol in DCM) afforded 5.40 g of the product (92% yield).

$^1$H NMR (DMSO-D$_6$, 300 MH$_Z$): δ 8.20-8.18 (d, 1H), 7.65 (d, 1H), 7.53-7.49 (m, 2H), 3.90-3.84 (m, 2H), 3.47-3.41 (m, 2H). LCMS Purity: 98%, m/z=198.1 (M+1). HPLC Purity: 98%

Preparation of Intermediate 1-(3-Bromo-pyridin-4-yl)-cyclobutanol (I-33c)

(I-33c)

3-bromopyridine (1 g, 6.329 mmol) was reacted with cylcobutanone (0.93 mL, 6.369 mmol), n-butyl lithium (4.02 mL, 7.64 mmol) and diisopropyl amine (0.99 mL, 7.005 mmol) in dry THF to afford the crude product. Purification by column chromatography on silica gel (40% ethyl acetate in hexane) afforded 802 mg of the product (55% yield). LCMS Purity: 79%, m/z=227.9 (M+1)

Preparation of the title compound 1-(2-chloro-pyridin-4-yl)-3-[4-(1-hydroxy-cyclobutyl)-pyridin-3-yl]-imidazolidin-2-one (33A)

Using analogous reagents and reaction conditions as described in Example 1 above, 1-(2-chloro-pyridin-4-yl)-imidazolidin-2-one (I-33b: 100 mg, 0.5076 mmol) was reacted with 1-(3-bromo-pyridin-4-yl)-cyclobutanol (I-33c: 127 mg, 0.5583 mmol) copper iodide (9.6 mg, 0.0507 mmol), trans-N,N'-dimethylcyclohexane-1,2-diamine (21 mg, 0.1522 mmol), potassium phosphate (269 mg, 1.269 mmol) and 1,4-dioxane (3 mL) to afford crude product. Purification by column chromatography on silica gel (2% methanol in CHCl₃), followed by preparative HPLC afforded 25 mg of pure product (14% yield)

¹H NMR (CDCl₃, 400 MHz): δ 8.59-8.53 (d, 2H), 8.31-8.29 (d, 1H), 7.57-7.55 (dd, 1H), 7.49 (d, 1H), 7.33-7.32 (d, 1H), 4.76 (s, 1H), 4.10-4.09 (m, 4H), 2.45-2.34 (m, 6H). LCMS Purity: 96%, m/z=345.1 (M+1). HPLC Purity: 99%

Example 34

Preparation of 1-(2-chloropyridin-4-yl)-3-(4-cyclopentyl-pyridin-3-yl)-imidazolidin-2-one (34A)

(34A)

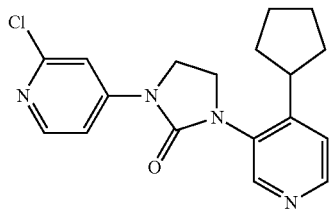

Preparation of Intermediate 1-(3-Bromo-pyridin-4-yl)-cyclopentanol (I-35a)

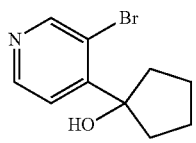

(I-34a)

Using analogous reaction condition and reagents as described in Example 20 for the preparation of I-20a above, 3-bromo pyridine solution (1.0 g, 6.36 mmol) was reacted with cyclopentanone solution (0.6 mL, 70 mmol) in dry THF (6 mL), n-BuLi solution (4.0 mL, 7.6 mmol) and diisopropylethyl amine (1.0 mL, 70 mmol) in dry THF (6 mL) to afford the crude product. The crude was purified by column chromatography on silica gel (20% ethyl acetate in hexane) afforded 520 mg of the product (34% yield).

¹H NMR (CDCl₃, 300 MHz): δ 8.68 (s, 1H), 8.48-8.46 (d, 1H), 7.60-7.58 (d, 1H), 2.41-2.34 (m, 3H), 2.05-1.90 (m, 7H), 1.25-1.21 (m, 1H) LCMS Purity: 97%, m/z=242.1 (M+1)

Preparation of Intermediate 3-bromo-4-cyclopent-1-enyl-pyridine (I-34b)

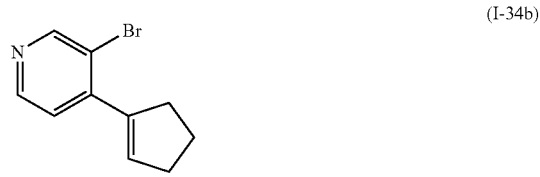 [SMILES: Brc1cnccc1C1=CCCC1]

PTSA (819 mg, 4.315 mmol) was added portionwise to a stirred mixture of 1-(3-bromo-pyridin-4-yl)-cyclopentanol (I-34a: 520 mg, 2.15 mmol) in 25 mL of toluene. The resulting mixture was heated to reflux at 120° C. for 4 hours. The reaction was monitored by TLC (20% ethyl acetate in hexane). The reaction mixture was concentrated, basified with aqueous sodium bicarbonate solution and extracted with ethyl acetate. The organic layer was washed with water, brine solution, dried over anhydrous sodium sulphate and concentrated to afford the crude product. Purification by column chromatography on silica gel (8% ethyl acetate in hexane) afforded 350 mg of the product (73% yield).

LCMS Purity: 100%, m/z=224.1 (M+1)

Preparation of Intermediate 3-bromo-4-cyclopentyl-pyridine (I-34c)

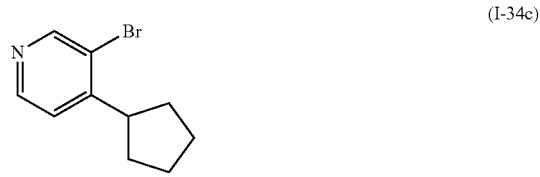 [SMILES: Brc1cnccc1C1CCCC1]

Platinum oxide (20 mg) was added to a mixture of 3-bromo-4-cyclopent-1-enyl-pyridine (I-34b: 140 mg, 0.622 mmol) in toluene (5 mL) and stirred overnight under hydrogen atmosphere. The reaction was monitored by TLC (20% ethyl acetate in hexane). The reaction mixture was filtered through celite pad and washed with toluene and concentrated to afford crude product. Purification by column chromatography (8% ethyl acetate in hexane) afforded 98 mg of the product (71% yield).

¹H NMR (CDCl₃, 300 MH$_z$): δ 8.64 (s, 1H), 8.42-8.40 (d, 1H), 7.21-7.19 (d, 1H), 3.37-3.34 (m, 1H), 2.18-2.12 (m, 2H), 1.87-1.73 (m, 6H).

Preparation of the title compound 1-(2-chloropyridin-4-yl)-3-(4-cyclopentyl-pyridin-3-yl)-imidazolidin-2-one (34A)

Using analogous reagents and reaction conditions as described in Example 1 above, 1-(2-chloro-pyridin-4-yl)imidazolidin-2-one (I-33b: 75 mg, 0.38 mmol) was reacted with and 3-bromo-4-cyclopentyl-pyridine (I-34c: 95 mg, 0.418 mmol) copper iodide (7.22 mg, 0.38 mmol), trans-N,N'-dimethylcyclohexane-1,2-diamine (16.21 mg, 0.114 mmol), potassium phosphate (241.9 mg, 1.15 mmol) and 1,4-dioxane (5 mL) to yield the crude product. Purified by preparative HPLC afforded 2.50 mg of the product (2% yield).

$^1$H NMR (CDCl$_3$, 300 MH$_Z$): δ 8.70-8.40 (m, 2H), 8.30-8.28 (d, 1H), 7.70-7.45 (m, 2H), 7.36 (s, 1H), 4.1-3.90 (m, 4H), 3.30-3.0 (m, 1H), 2.30-2.0 (m, 3H), 1.95-1.70 (m, 5H). LCMS Purity: 100%, m/z=343.3 (M+1). HPLC Purity: 96%

Example 35

Preparation of 1-(2-chloropyridin-4-yl)-3-[4-(1-hydroxy cyclopentyl)-pyridin-3-yl]-imidazolidin-2-one (35A)

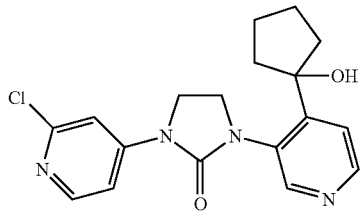

(35A)

Using analogous reagents and reaction conditions as described in Example 1 above, 1-(2-chloro-pyridin-4-yl)imidazolidin-2-one (I-33b: 100 mg, 0.5 mmol) was reacted with 1-(3-bromo-pyridin-4-yl)-cyclopentanol (I-34a: 135 mg, 0.558 mmol), copper iodide (9.6 mg, 0.05 mmol), trans-N,N'-dimethylcyclohexane-1,2-diamine (21.62 mg, 0.15 mmol), potassium phosphate (322.87 mg, 1.52 mmol) and 1,4-dioxane (5 mL) to yield the crude product. Purification by preparative HPLC afforded 20 mg of the product (11% yield).

$^1$H NMR (DMSO-D$_6$, 400 MH$_Z$): δ 8.52-8.51 (m, 2H), 8.26-8.24 (d, 1H), 7.69 (d, 1H), 7.61-7.59 (dd, 1H), 7.56-7.55 (d, 1H), 5.09 (s, 1H), 4.1-3.99 (m, 3H), 3.90-3.75 (bs, 1H), 2.10-1.9, (m, 3H), 1.78-1.63 (m, 5H). LCMS Purity: 98%, m/z=359.1 (M+1). HPLC Purity: 96%

Example 36

Preparation of 1-[4-(1-hydroxy-cyclopropyl)-pyridin-3-yl]-3-(3-trifluoromethyl-phenyl)-imidazolidin-2-one (36A)

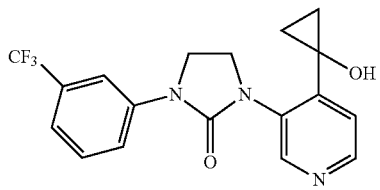

(36A)

Preparation of Intermediate 1-(2-Chloro-ethyl)-3-(3-trifluoromethyl-phenyl)-urea (I-36a)

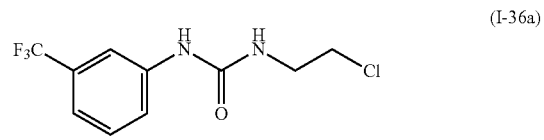 [SMILES: O=C(NCCCl)Nc1cccc(C(F)(F)F)c1]

(I-36a)

Using analogous reagents and reaction conditions as described in Example 1 above, 3-trifluoromethyl-phenylamine (2.0 g, 12.412 mmol) in toluene (20 mL) was reacted with 1-chloro-2-isocyanatoethane (1.96 g, 18.618 mmol to give 3.2 g of pure product (96%)

$^1$H NMR (CDCl$_3$, 300 MH$_Z$): δ 7.60-7.20 (m, 5H), 5.75 (bs, 1H), 3.80-3.45 (m, 4H). LCMS Purity: 100%, m/z=266.9 (M+1)

Preparation of Intermediate 1-(3-trifluoromethyl-phenyl)-imidazolidin-2-one (I-36b)

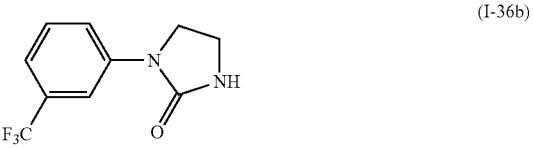 [SMILES: O=C1NCCN1c1cccc(C(F)(F)F)c1]

(I-36b)

Using analogous reagents and reaction conditions as described in Example 1 above, 1-(2-chloro-ethyl)-3-(3-trifluoromethyl-phenyl)-urea (I-36a: 3.2 g, 12.02 mmol) was reacted with sodium hydride (870 mg, 18.03 mmol) in dry THF (35 mL to give 2.9 g of product (95%)

$^1$H NMR (CDCl$_3$, 300 MH$_Z$): δ 7.86-7.70 (m, 2H), 7.50-7.40 (t, 1H), 7.35-7.24 (m, 1H), 5.20 (bs, 1H), 4.0-3.90 (t, 2H), 3.70-3.60 (t, 2H). LCMS Purity: 100%, m/z=231 (M+1)

Preparation of Intermediate 3-[2-Oxo-3-(3-trifluoromethyl-phenyl)-imidazolidin-1-yl]-isonicotinic acid ethyl ester (I-36c)

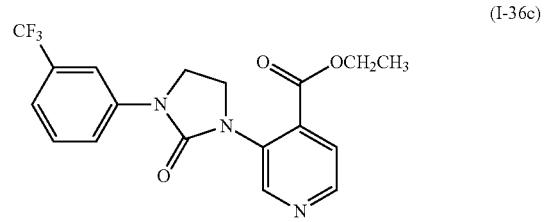 [SMILES: CCOC(=O)c1ccncc1N1CCN(c2cccc(C(F)(F)F)c2)C1=O]

(I-36c)

Using analogous reagents and reaction conditions as described in Example 1 above, 1-(3-trifluoromethyl-phenyl)-imidazolidin-2-one (I-36b: 200 mg, 0.869 mmol) was reacted with 3-bromo-isonicotinic acid ethyl ester (239 mg, 1.042 mmol), copper iodide (16.5 mg, 0.869 mmol), trans-N,N'-dimethylcyclohexane-1,2-diamine (37.01 mg, 0.26 mmol), potassium phosphate (460.5 mg, 2.172 mmol) and 1,4-dioxane (5 mL) to afford crude product. Purification by column chromatography on silica gel (60% ethyl acetate in hexane) afforded 280 mg of pure product (85% yield).

¹H NMR (CDCl₃, 300 MHz): δ 8.64-8.61 (m, 1H), 7.84-7.82 (d, 2H), 7.73-7.72 (d, 1H), 7.47 (t, 1H), 7.40-7.32 (m, 1H), 4.38-4.31 (q, 2H), 4.13-4.09 (m, 4H), 1.34-1.30 (t, 3H).

Preparation of the title compound 1-[4-(1-hydroxy-cyclopropyl)-pyridin-3-yl]-3-(3-trifluoromethyl-phenyl)-imidazolidin-2-one (36A)

2.5 M Solution of EtMgBr (0.8 mL, 1.974 mmol) was added drop wise to a solution of titanium(IV)isopropoxide (187.3 mg, 0.659 mmol) in diethyl ether (10 mL) for a period of 15 minutes at −78° C. under nitrogen atmosphere. The resulting mixture was stirred for 90 minutes. This was followed by the addition of 3-[2-oxo-3-(3-trifluoromethyl-phenyl)-imidazolidin-1-yl]-isonicotinic acid ethyl ester (I-36c: 125 mg, 0.329 mmol) in diethyl ether (3 mL) at −78° C. and continued stirring at room temperature overnight. The reaction was monitored by TLC (80% ethyl acetate in hexane). The reaction mixture was cooled and partitioned between ethyl acetate and 1N HCl. The organic layer was concentrated to yield crude product which was purified by preparative HPLC to afford 8 mg of the product (6% yield).

¹H NMR (CDCl₃, MHz): δ 8.52 (s, 1H), 8.41 (d, 1H), 7.99-7.98 (d, 1H), 7.87-7.85 (d, 1H), 7.76-7.74 (dd, 1H), 7.47-7.46 (d, 1H), 7.32-7.31 (d, 1H), 6.82-6.80 (d, 1H), 4.17-4.14 (m, 2H), 4.03-3.99 (m, 2H), 2.15-2.05 (m, 1H), 1.15-1.11 (m, 2H), 0.86-0.82 (m, 2H). LCMS Purity: 95%, m/z=336.1 (M+1). HPLC Purity: 98%

Example 37

Preparation of 1-(2-chloro-6-(trifluoromethyl)pyridin-4-yl)-3-(4-cyclopropylpyridin-3-yl)imidazolidin-2-one (37A)

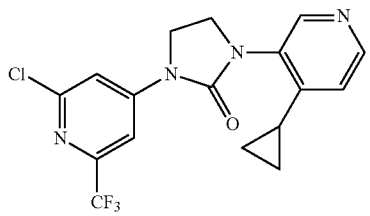

(37A)

Using analogous reagents and reaction conditions as described in Example 1 above, 1-(4-cyclopropylpyridin-3-yl)imidazolidin-2-one (I-1d: 110 mg, 0.5412 mmol) was reacted with 2-chloro-4-iodo-6-(trifluoromethyl)pyridine (200 mg, 0.6494 mmol), 1,4-dioxane (5 mL), copper iodide (10 mg, 0.0541 mmol), trans-N1,N2-dimethylcyclohexane-1,2-diamine (23 mg, 0.1623 mmol) and potassium phosphate (345 mg, 1.6236 mmol) to afford the crude product. Purification by column chromatography on silica gel (1.5% methanol in CHCl₃), followed by prep HPLC afforded 22 mg of the product (10% yield).

¹H NMR (CDCl₃, 300 MHz): δ 8.65-8.35 (bs, 2H), 8.0 (s, 1H), 7.7 (s, 1H), 6.90-6.80 (bs, 1H), 4.15-4.05 (m, 4H), 2.0-1.9 (m, 1H), 1.20-1.10 (m, 2H), 0.92-0.80 (m, 2H). LCMS Purity: 98%, m/z=383.1 (M+1). HPLC Purity: 99%

Example 38

Preparation of 1-(4-cyclopropylpyridin-3-yl)-3-(6-cyclopropylpyrimidin-4-yl)imidazolidin-2-one (38A)

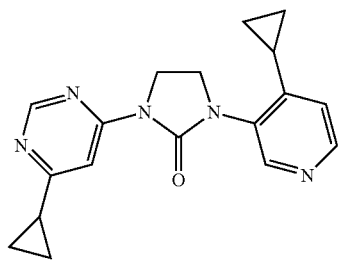

(38A)

Preparation of Intermediate 1-(6-chloropyrimidin-4-yl)-3-(4-cyclopropylpyridin-3-yl)imidazolidin-2-one (I-38a)

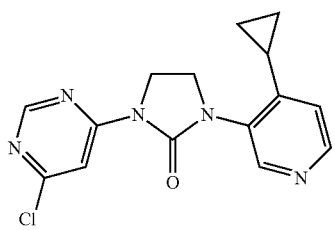

(I-38a)

Using analogous reagents and reaction conditions as described in Example 11 above, 1-(4-cyclopropylpyridin-3-yl)imidazolidin-2-one (I-1d: 500 mg, 2.46 mmol) was reacted with 4,6-dichloro-pyrimidine (403 mg, 2.70 mmol), 2-dicyclohexylphosphino-2',4',6'-triisopropylbiphenyl (117 mg, 0.246 mmol), Pd₂(dba)₃ (112 mg, 0.123 mmol), cesium carbonate (2.009 g, 6.15 mmol) and toluene (10 mL) in seal tube at 110° C. for 14 hours. Purification by column chromatography on silica gel (1.5% methanol in chloroform) afforded 140 mg of the product (18.18% yield).

¹HNMR (CDCl₃, 300 MHz): δ 8.688-8.684 (d, 1H), 8.48-8.46 (m, 2H), 8.375-8.371 (d, 1H), 6.85-6.83 (d, 1H), 4.33-4.27 (t, 2H), 4.03-3.98 (t, 2H), 2.05-1.95 (m, 1H), 1.21-1.12 (m, 2H), 0.88-0.82 (m, 2H). LCMS: 99.53%, m/z=315.9 (M+1).

Preparation of 1-(4-cyclopropylpyridin-3-yl)-3-(6-cyclopropylpyrimidin-4-yl)imidazolidin-2-one (38A)

Using analogous reagents and reaction conditions as described in Example 1 above, 1-(6-chloropyrimidin-4-yl)-3-(4-cyclopropylpyridin-3-yl)imidazolidin-2-one (I-38a: 140 mg, 0.44 mmol) was reacted with cyclopropyl boronic acid (46 mg, 0.533 mmol), Pd(PPh₃)₄ (26 mg, 0.02 mmol), potassium carbonate (123 mg, 0.888 mmol) and xylene (10 mL) in seal tube at 125° C. for 14 hours. Purification by column chromatography on silica gel (1% methanol in chloroform) afforded 55 mg of the product (38.73% yield).

¹HNMR (CDCl₃, 300 MHz): δ 8.70 (s, 1H), 8.48 (s, 1H), 8.45-8.43 (d, 1H), 8.15 (s, 1H), 6.83-6.81 (d, 1H), 4.30-4.25 (t, 2H), 4.00-3.94 (t, 2H), 2.00-1.96 (m, 2H), 1.16-1.04 (m, 6H), 0.86-0.83 (m, 2H). LCMS: 98.39%, m/z=322.2 (M+1). HPLC: 90.41%.

Example 39

Preparation of 1-(4-cyclopropylpyridin-3-yl)-3-(2-cyclopropylpyridin-4-yl)imidazolidin-2-one (39A)

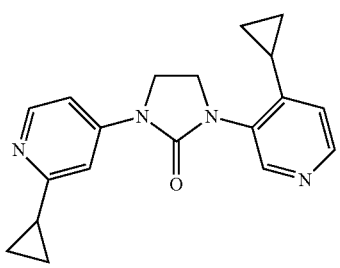

(39A)

Preparation of Intermediate 1-(2-chloropyridin-4-yl)-3-(4-cyclopropylpyridin-3-yl)imidazolidin-2-one (I-39a)

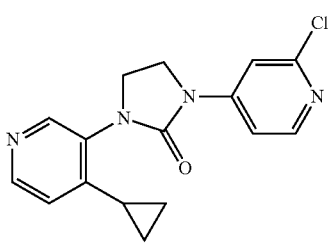

(I-39a)

Using analogous reagents and reaction conditions as described in Example 1 above, 1-(4-cyclopropylpyridin-3-yl)imidazolidin-2-one (I-1d: 200 mg, 0.985 mmol) was reacted with 2-chloro-4-iodo pyridine (283 mg, 0.118 mmol) 1,4-dioxane (10 mL), copper iodide (19 mg, 0.0985 mmol), trans-N,N'-dimethylcyclohexane-1,2-diamine (14 mg, 0.0985 mmol) and potassium phosphate (626 mg, 2.95 mmol) to afford the crude product. Purification by column chromatography on silica gel (2% methanol in chloroform) afforded 220 mg of the product (71.10% yield).

LCMS: 100%, m/z=315.1 (M+1).

Preparation of 1-(4-cyclopropylpyridin-3-yl)-3-(2-cyclopropylpyridin-4-yl)imidazolidin-2-one (39A)

1-(2-chloropyridin-4-yl)-3-(4-cyclopropylpyridin-3-yl)imidazolidin-2-one (I-39a: 220 mg, 0.7 mmol) was reacted with cyclopropyl boronic acid (72 mg, 0.84 mmol), Pd(PPh₃)₄ (41 mg, 0.035 mmol), potassium carbonate (194 g, 1.4 mmol) and xylene (10 mL) in seal tube at 125° C. for 14 hours. Purification by column chromatography on silica gel (1% methanol in chloroform) afforded 75 mg of the product (33.48% yield).

¹HNMR (CDCl₃, 400 MHz): δ 8.48 (s, 1H), 8.43-8.42 (d, 1H), 8.34-8.33 (d, 1H), 7.50-7.49 (d, 1H), 7.24-7.22 (dd, 1H), 6.81-6.80 (d, 1H), 4.09-3.97 (m, 4H), 2.05-1.98 (m, 2H), 1.15-1.10 (m, 2H), 1.05-0.94 (m, 4H), 0.85-0.81 (m, 2H). LCMS: 100%, m/z=321.2 (M+1). HPLC: 98.90%.

Example 40

Preparation of 1-(4-cyclopropylpyridin-3-yl)-3-(6-methoxypyrimidin-4-yl)imidazolidin-2-one (40A)

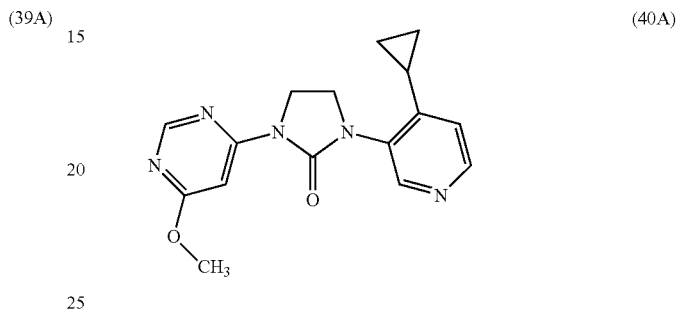

(40A)

Using analogous reagents and reaction conditions as described in Example 11 above, 1-(4-cyclopropylpyridin-3-yl)imidazolidin-2-one (I-1d: 100 mg, 0.492 mmol) was reacted with 4-chloro-6-methoxypyrimidine (78 mg, 0.541 mmol), 2-dicyclohexyl-phosphino-2',4',6'-triisopropylbiphenyl (23 mg, 0.0492 mmol), Pd₂(dba)₃ (23 mg, 0.024 mmol), cesium carbonate (400 mg, 1.23 mmol) and toluene (10 mL) in seal tube at 115° C. for 14 hours. Purification by column chromatography on silica gel (2% methanol in chloroform) afforded 50 mg of the product (34.6% yield).

¹HNMR (CDCl₃, 400 MHz): δ 8.53 (s, 1H), 8.47 (s, 1H), 8.43-8.42 (d, 1H), 7.66 (s, 1H), 6.82-6.80 (d, 1H), 4.30-4.26 (t, 2H), 3.97-3.93 (m, 5H), 2.02-1.98 (m, 1H), 1.15-1.10 (m, 2H), 0.85-0.80 (m, 2H). LCMS: 98.15%, m/z=313.1 (M+1). HPLC: 99.04%.

Example 41

Preparation of 1-(4-cyclopropylpyridin-3-yl)-3-(6-methylpyrimidin-4-yl)imidazolidin-2-one (41A)

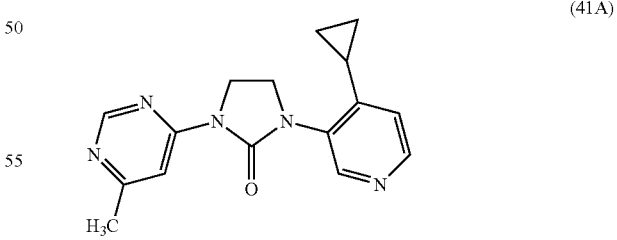

(41A)

Using analogous reagents and reaction conditions as described in Example 11 above, 1-(4-cyclopropylpyridin-3-yl)imidazolidin-2-one (I-1d: 100 mg, 0.492 mmol) was reacted with 4-chloro-6-methylpyrimidine (73 mg, 0.541 mmol), 2-dicyclohexyl-phosphino-2',4',6'-triisopropylbiphenyl (23 mg, 0.0492 mmol), Pd₂(dba)₃ (23 mg, 0.024 mmol), cesium carbonate (400 mg, 1.23 mmol) and toluene (10 mL) in seal tube at 115° C. for 14 hours. Purification by column chromatography on silica gel (2% methanol in chloroform) afforded 30 mg of the product (21.1% yield).

¹HNMR (CDCl₃, 300 MHz): δ 8.78 (s, 1H), 8.48 (s, 1H), 8.45-8.43 (d, 1H), 8.16 (s, 1H), 6.83-6.81 (d, 1H), 4.31-4.28 (t, 2H), 4.01-3.95 (t, 2H), 2.49 (s, 3H), 2.02-1.98 (m, 1H), 1.18-1.11 (m, 2H), 0.88-0.82 (m, 2H). LCMS: 100%, m/z=296.1 (M+1). HPLC: 92.00%.

Example 42

Preparation of 1-(4-cyclopropylpyridin-3-yl)-3-(5-fluoro-4-methylpyridin-2-yl)imidazolidin-2-one (42A)

(42A)

Using analogous reagents and reaction conditions as described in Example 1 above, 1-(4-cyclopropylpyridin-3-yl) imidazolidin-2-one (I-1d: 100 mg, 0.492 mmol) was reacted with 2-bromo-5-fluoro-4-methylpyridine (102 mg, 0.541 mmol) 1,4-dioxane (5 mL), copper iodide (9 mg, 0.0492 mmol), trans-N,N'-dimethylcyclohexane-1,2-diamine (21 mg, 0.147 mmol) and potassium phosphate (313 mg, 1.47 mmol) to afford the crude product. Purification by column chromatography on silica gel (80% ethyl acetate in hexane) afforded 60 mg of the product (39.21% yield).

¹HNMR (CDCl₃, 300 MHz): δ 8.19-8.17 (d, 1H), 8.05 (s, 1H), 7.27 (s, 1H), 4.27-4.22 (t, 2H), 3.96-3.91 (t, 2H), 2.30 (s, 3H), 2.08-2.00 (m, 1H), 1.13-1.10 (m, 2H), 0.83-0.81 (m, 2H). LCMS: 100%, m/z=314.1 (M+1). HPLC: 92.09%.

Example 43

Preparation of 1-(4-cyclopropylpyridin-3-yl)-3-(2-cyclopropylpyrimidin-4-yl)imidazolidin-2-one (43A)

(43A)

Preparation of Intermediate 4-chloro-2-cyclopropylpyrimidine (I-43a)

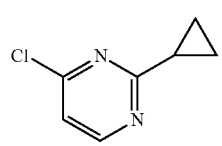

(I-43a)

POCl₃ (5 mL) was added to 2-cyclopropylpyrimidin-4-ol (100 mg, 0.735 mmol) and refluxed at 150° C. for 2.5 hours. The resulting mixture was concentrated, the concentrate was basified with dilute sodium bicarbonate solution and diluted with DCM. The organic layer was washed with brine, dried over sodium sulphate and concentrated to afford 125 mg of the crude product as a pale brown liquid.

¹HNMR (CDCl₃, 300 MHz): δ 8.42-8.40 (d, 1H), 7.09-7.07 (d, 1H), 2.25-2.20 (m, 1H), 1.24-1.14 (m, 4H).

Preparation of 1-(4-cyclopropylpyridin-3-yl)-3-(2-cyclopropylpyrimidin-4-yl)imidazolidin-2-one (43A)

Using analogous reagents and reaction conditions as described in Example 11 above, 1-(4-cyclopropylpyridin-3-yl)imidazolidin-2-one (I-1d: 100 mg, 0.492 mmol) was reacted with 4-chloro-2-cyclopropylpyrimidine (I-43a: 92 mg, 0.591 mmol), 2-dicyclohexylphosphino-2',4',6'-triisopropylbiphenyl (24 mg, 0.0492 mmol), Pd₂(dba)₃ (23 mg, 0.0246 mmol), cesium carbonate (400 mg, 1.23 mmol) and toluene (5 mL) in seal tube at 110° C. for 14 hours. Purification by column chromatography on silica gel (2% methanol in chloroform), followed by preparative HPLC afforded 25 mg of the product (% yield).

¹HNMR (CDCl₃, 300 MHz): δ 8.46 (s, 1H), 8.43-8.42 (d, 1H), 8.36-8.34 (d, 1H), 8.00-7.97 (dd, 1H), 6.81-6.80 (d, 1H), 4.28-4.23 (t, 2H), 3.97-3.92 (t, 2H), 2.19-2.14 (m, 1H), 2.01-1.95 (m, 1H), 1.15-0.99 (m, 6H), 0.87-0.79 (m, 2H). LCMS: 96.64%, m/z=322.1 (M+1). HPLC: 98.82%.

Example 44

Preparation of 1-(4-cyclopropylpyridin-3-yl)-3-(2-methylpyrimidin-4-yl)imidazolidin-2-one (44A)

(44A)

Using analogous reagents and reaction conditions as described in Example 11 above, 1-(4-cyclopropylpyridin-3-yl)imidazolidin-2-one (I-1d: 100 mg, 0.492 mmol) was reacted with 4-chloro-2-methylpyrimidine (68 mg, 0.541 mmol), 2-dicyclohexyl-phosphino-2',4',6'-triisopropylbiphenyl (23 mg, 0.0492 mmol), Pd₂(dba)₃ (23 mg, 0.024 mmol), cesium carbonate (400 mg, 1.23 mmol) and toluene (5 mL) in seal tube at 110° C. for 14 hours. Purification by column chromatography on silica gel (1.5% methanol in chloroform) afforded 76 mg of the product (52% yield).

¹HNMR (CDCl₃, 400 MHz): δ 8.48-8.41 (m, 3H), 8.08-8.06 (d, 1H), 6.83-6.81 (d, 1H), 4.31-4.27 (t, 2H), 3.99-3.95 (t, 2H), 2.64 (s, 3H), 2.03-1.97 (m, 1H), 1.15-1.10 (m, 2H), 0.88-0.81 (m, 2H). LCMS: 98.50%, m/z=296.1 (M+1). HPLC: 96.16%.

Example 45

Preparation of 1-(6-chloro-2-(trifluoromethyl)pyrimidin-4-yl)-3-(4-cyclopropylpyridin-3-yl)imidazolidin-2-one (45A)

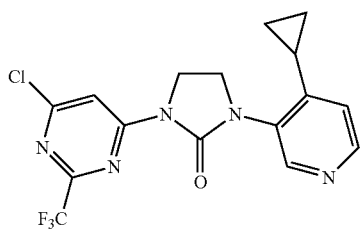

(45A)

Using analogous reagents and reaction conditions as described in Example 11 above, 1-(4-cyclopropylpyridin-3-yl)imidazolidin-2-one (I-1d: 100 mg, 0.492 mmol) was reacted with 4,6-dichloro-2-trifluoromethylpyrimidine (120 mg, 0.541 mmol), xantphos (25 mg, 0.04428 mmol), Pd₂(dba)₃ (15 mg, 0.01476 mmol), cesium carbonate (225 mg, 0.6888 mmol) and 1,4-dioxane (5 mL) in a sealed tube for 5 hours. Purification by column chromatography on silica gel (1% methanol in chloroform) followed by preparative HPLC afforded 25 mg of the product (13.24% yield).

¹HNMR (CDCl₃, 300 MHz): δ 8.51-8.46 (m, 2H), 7.26 (m, 1H), 6.85-6.83 (d, 1H), 4.38-4.32 (t, 2H), 4.05-4.00 (t, 2H), 2.00-1.90 (m, 1H), 1.16-1.11 (m, 2H), 0.88-0.84 (m, 2H). LCMS: 96.71%, m/z=383.6 (M+1). HPLC: 98.68%.

Example 46

Preparation of 1-(4-cyclopropylpyridin-3-yl)-3-(2,6-dichloropyridin-4-yl)imidazolidin-2-one (46A)

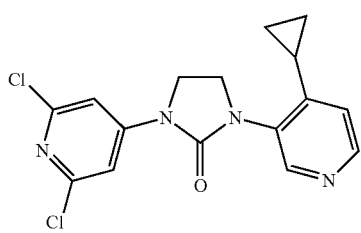

(46A)

Using analogous reagents and reaction conditions as described in Example 1 above, 1-(4-cyclopropylpyridin-3-yl)imidazolidin-2-one (I-1d: 500 mg, 2.4630 mmol) was reacted with 2,6-dichloro-4-iodopyridine (810 mg, 2.9556 mmol), copper iodide (47 mg, 0.2463 mmol), trans-cyclohexane-1,2-diamine (0.089 mL, 0.7389 mmol), potassium phosphate (1.56 g, 7.3891 mmol) and 1,4-dioxane (10 mL) to afford crude product. Purification by column chromatography on silica gel (2% methanol in chloroform) afforded 800 mg of pure product (93.02% yield).

¹HNMR (CDCl₃, 300 MHz): δ 8.48-8.43 (m, 2H), 7.57 (s, 2H), 6.85-6.81 (d, 1H), 4.04 (s, 4H), 2.00-1.90 (m, 1H), 1.20-1.10 (m, 2H), 0.9-0.8 (m, 2H). LCMS: 97.01%, m/z=348.8 (M+1). HPLC: 99.40%.

Example 47

Preparation of 1-(2-chloro-6-cyclopropylpyridin-4-yl)-3-(4-cyclopropylpyridin-3-yl)imidazolidin-2-one (47A)

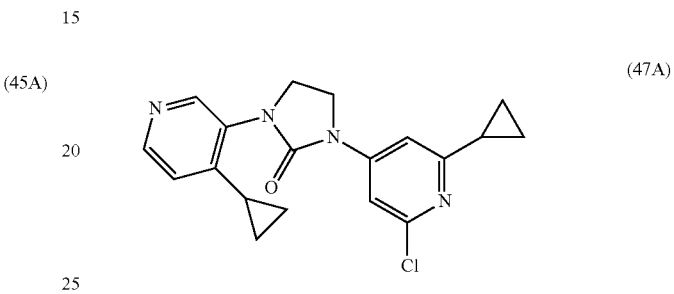

(47A)

Using analogous reagents and reaction conditions as described in Example 1 above, 1-(4-cyclopropyl pyridin-3-yl)-3-(2,6-dichloropyridin-4-yl)imidazolidin-2-one (I-46a: 100 mg, 0.2865 mmol) was reacted with cyclopropyl boronic acid (74 mg, 0.8593 mmol), Pd(PPh₃)₄ (7 mg, 0.0057 mmol), sodium carbonate (69 g, 0.6590 mmol) and toluene (5 mL) in seal tube at 120° C. for 12 hours. Purification by column chromatography on silica gel (1% methanol in chloroform), followed by preparative HPLC afforded 20 mg of the product (20% yield).

¹HNMR (CDCl₃, 400 MHz): δ 8.49-8.45 (m, 2H), 7.524-7.520 (d, 1H), 7.21-7.20 (d, 1H), 6.84-6.82 (d, 1H), 4.08-3.99 (m, 4H), 2.03-1.96 (m, 2H), 1.17-1.12 (m, 2H), 1.07-0.96 (m, 4H), 0.87-0.83 (m, 2H). LCMS: 100%, m/z=355.1 (M+1). HPLC: 98.74%.

Example 48

Preparation of 1-(2-cyclopropyl-6-(trifluoromethyl)pyridin-4-yl)-3-(4-cyclopropylpyridin-3-yl)imidazolidin-2-one (48A)

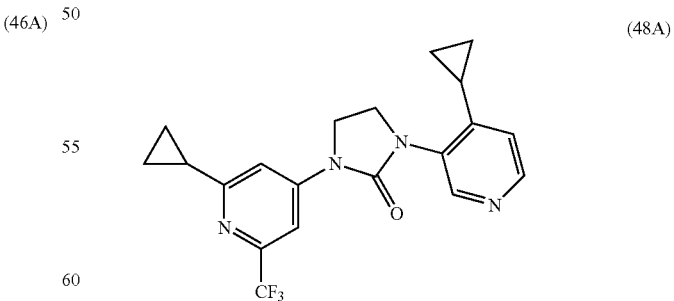

(48A)

Using analogous reagents and reaction conditions as described in Example 1 above, 1-(4-cyclopropylpyridin-3-yl)imidazolidin-2-one (I-1d: 260 mg, 1.2807 mmol) was reacted with 2-chloro-4-iodo-6-(trifluoromethyl)pyridine (471 mg, 1.5369 mmol), copper iodide (24 mg, 0.1280 mmol), transcyclohexane-1,2-diamine (15 mg, 0.1280 mmol), potassium phosphate (816 mg, 3.8421 mmol) and 1,4-dioxane (5 mL) to afford crude product. Purification by column chromatography on silica gel (1% methanol in chloroform) afforded 250 mg of pure product (51.1% yield).

$^1$HNMR (CDCl$_3$, 400 MHz): δ 8.55-8.42 (bs, 2H), 7.64-7.62 (d, 2H), 6.85 (s, 1H), 4.13-4.02 (m, 4H), 2.10-1.98 (m, 2H), 1.18-0.99 (m, 6H), 0.87-0.83 (m, 2H). LCMS: 98.89%, m/z=388.9 (M+1). HPLC: 99.67%.

Example 49

Preparation of 1-(2,6-bis(trifluoromethyl)pyridin-4-yl)-3-(4-cyclopropylpyridin-3-yl)imidazolidin-2-one (49A)

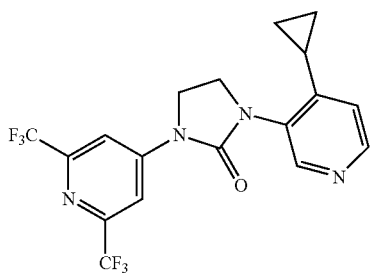

(49A)

Using analogous reagents and reaction conditions as described in Example 11, 1-(4-cyclopropylpyridin-3-yl)imidazolidin-2-one (I-1d: 90 mg, 0.4408 mmol) was reacted with 4-chloro-2,6-trifluoromethylpyridine (100 mg, 0.4007 mmol), 2-dicyclohexyl-phosphino-2',4',6'-triisopropylbiphenyl (10 mg, 0.02 mmol), Pd$_2$(dba)$_3$ (19 mg, 0.02 mmol), cesium carbonate (183 mg, 0.5610 mmol) and toluene (5 mL) in seal tube at 110° C. for 14 hours. Purification by column chromatography on silica gel (2% methanol in chloroform) followed by preparative HPLC afforded 81 mg of the product (48.79% yield).

$^1$HNMR (CDCl$_3$, 300 MHz): δ 8.48-8.46 (m, 2H), 8.12 (s, 2H), 6.85-6.84 (d, 1H), 4.20-4.07 (m, 4H), 1.98-1.93 (m, 1H), 1.18-1.11 (m, 2H), 0.88-0.83 (m, 2H). LCMS: 100%, m/z=417.4 (M+1). HPLC: 98.38%.

Example 50

Preparation of 1-(4-cyclopropyl-2-hydroxypyridin-3-yl)-3-(2-(trifluoromethyl)pyridin-4-yl)imidazolidin-2-one (50A)

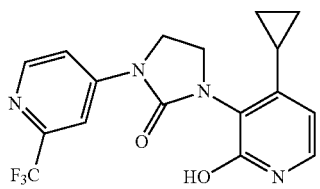

(50A)

Preparation of Intermediate 4-cyclopropyl-3-iodopyridine 1-oxide (I-50a)

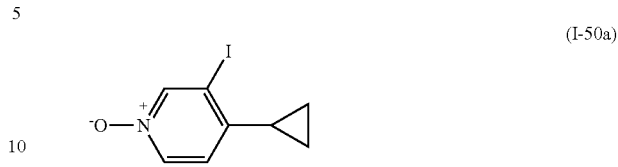

(I-50a)

m-Chloroperbenzoic acid (408 mg, 2.36 mmol) was added to the solution of 4-cyclopropyl-3-iodopyridine (I-30a: 200 mg. 0.816 mmol) in DCM (10 mL) and the resulting mixture was stirred at room temperature for 3 hours. The reaction was monitored by TLC. The reaction mixture was quenched with ice and diluted with DCM. The organic layer was washed with dilute NaOH solution, water and brine solution, dried over sodium sulphate and concentrated to afford 200 mg of the product (94.7% yield).

$^1$HNMR (DMSO-D$_6$, 300 MHz): δ 8.59-8.58 (d, 1H), 8.09-8.06 (dd, 1H), 6.91-6.89 (d, 1H), 2.05-1.90 (m, 1H), 1.08-1.04 (m, 2H), 0.74-0.72 (m, 2H). LCMS: 99.45%, m/z=261.4 (M+1).

Preparation of Intermediate 4-cyclopropyl-3-(2-oxo-3-(2-(trifluoromethyl)pyridin-4-yl)imidazolidin-1-yl)pyridine 1-oxide (I-50b)

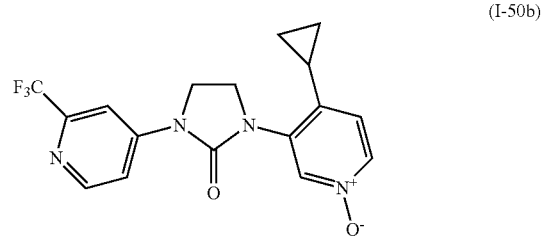 [SMILES: O=C1N(c2ccnc(C(F)(F)F)c2)CCN1c1c[n+]([O-])ccc1C1CC1]

(I-50b)

I-50b

Using analogous reagents and reaction conditions as described in Example 1 above, 1-(3-trifluoromethyl-phenyl)-imidazolidin-2-one (I-36b: 60 mg, 0.259 mmol) was reacted with 4-cyclopropyl-3-iodopyridine 1-oxide (I-50a: 81 mg, 0.31 mmol), copper iodide (5 mg, 0.025 mmol), trans-N,N'-dimethylcyclohexane-1,2-diamine (4 mg, 0.025 mmol), potassium phosphate (165 mg, 0.77 mmol) and 1,4-dioxane (5 mL) to afford crude product. Purification by column chromatography on silica gel (1.5% methanol in chloroform) afforded 65 mg of pure product (71.4% yield).

$^1$HNMR (CDCl$_3$, 400 MHz): δ 8.63-8.62 (d, 1H), 8.19-8.18 (d, 1H), 8.10-8.08 (dd, 1H), 7.92-7.91 (d, 1H), 7.73-7.71 (dd, 1H), 6.84-6.83 (d, 1H), 4.15-4.11 (m, 2H), 4.05-4.01 (m, 2H), 1.96-1.92 (m, 1H), 1.16-1.11 (m, 2H), 0.81-0.78 (m, 2H). LCMS: 100%, m/z=365.1 (M+1). HPLC: 99.70%.

Preparation of 1-(4-cyclopropyl-2-hydroxypyridin-3-yl)-3-(2-(trifluoromethyl)pyridin-4-yl)imidazolidin-2-one (50A)

4-Cyclopropyl-3-(2-oxo-3-(2-(trifluoromethyl)pyridin-4-yl)imidazolidin-1-yl)pyridine 1-oxide (I-50b: 100 mg, 0.273 mmol) was heated with acetic anhydride (5 mL) at 120° C. for 3 hours. The resulting mixture was concentrated, basified with dilute sodium bicarbonate solution, and diluted with DCM. The organic layer was dried over sodium sulphate and concentrated to afford the crude product. Purification by column chromatography on silica gel (3% methanol in chloroform), followed by preparative HPLC afforded 8 mg of the product (8% yield).

$^1$HNMR (CD$_3$OD, 300 MHz): δ 8.53-8.51 (d, 1H), 8.30-8.29 (d, 1H), 7.68-7.65 (dd, 1H), 7.36-7.33 (d, 1H), 5.90-5.88 (d, 1H), 4.18-3.93 (m, 4H), 3.81-3.75 (m, 1H), 2.18-2.13 (m, 1H), 1.15-1.11 (m, 2H), 0.95-0.93 (m, 2H). LCMS: 98.62%, m/z=364.9 (M+1). HPLC: 96.87%.

PHARMACOLOGICAL TESTING

The abbreviations listed below and used in the preparations below have the corresponding meanings.
CYP Cytochrome P450
CPM Counts per minute
Cyt b5 Cytochrome b5
DMSO Dimethyl sulfoxide
DHEA Dehydroepiandrosterone
NADPH Nicotinamide adenine dinucleotide phosphate Human and Rat-Cytochrome P450, 17-20 Lyase 1) Cytochrome P450, 17-20 lyase (CYP17-Lyase) Assay Dcyclopment Using Recombinant Human CYP17 Enzyme and 17-α-Hydroxy Pregnenolone [21-3H] as the Substrate.

Cytochrome P450, 17-α-Hydroxylase, 17-20 lyase (CYP17) is a multi functional enzyme that plays a key role in the biosynthesis of steroid hormones. It catalyses both conventional hydroxylation and also the carbon-carbon bond cleavage reactions (Peter Lee-Robichaud et al, *Biochem. J*, (1997) 321, 857-63). In the hydroxylation reaction, it converts progesterone and pregnenolone to the corresponding hydroxylated products 17-α-hydroxy progesterone and 17-α-hydroxy pregnenolone. In the lyase reaction, it catalyzes the conversion of these hydroxylated substrates to Androstenedione and Dehydroepiandrosterone (DHEA) respectively. In the Cyp17 lyase assay described here, the conversion of 17-α-hydroxy pregnenolone to Dehydroepiandrosterone and acetic acid is being monitored.

The hydroxylation and cleavage activities are catalyzed sequentially at the common active site of Cyp17 and proceed through transfer of two electrons from NADPH via its redox partner, cytochrome P450 reductase (CPR). The reaction mechanism for each activity is thought to involve formation of distinct iron-oxygen complexes. Cytochromeb5 selectively stimulates the lyase activity and has no significant effect on its hydroxylase activity. Lyase activity is stimulated by cytochrome b5 up to 10-fold in reconstituted assays with insignificant stimulation of the hydroxylase activity (MK Akthar et al, *Journal of Endocrinology* (2005) 187, 267-274 and Katagiri M et al, *Biophysical Research Communications* (1982) 108, 379-384).

Assay method was adopted from a published protocol with some modifications to suit our requirements (Dmitry N Grigoryev et al, *Analytical Biochemistry*, (1999) 267, 319-330). The conversion of 17-α-hydroxy pregnenolone to Dehydroepiandrosterone is accompanied by the release of acetic acid. In the Cyp17 lyase assay, 17-α-hydroxy pregnenolone labeled with tritium (3H) at position 21 is used as the substrate. Chloroform extraction removes the radioactive steroids and acetic acid is taken into aqueous layer. The tritiated acetic acid released in the assay thus extracted is quantified to determine the enzyme activity.

Initial buffer conditions were, 50 mM Phosphate buffer, pH 7.5 was used as the starting buffer for Cyp17 lyase activity based on the data published in US patent publication No. US2004/0198773 A1. This buffer was found to be suitable for regular Cyp17 lyase assay. Human Cyp 17 gene was cloned and expressed in Adenoviral expression system in A549 cell lines. The purified cell membrane preparations were used as the source for Human CYP17 enzyme. Total protein concentration: 8 mg/mL.

To identify the appropriate concentration of the enzyme required for the assay, concentration dependent enzyme activity was determined at a substrate (17-α-hydroxypregnenolone[21-3H]) concentration of 0.5 µM (Vincent C. O. Nijar, et al., *J Med Chem*, (1998) 41, 902-912). The protein activity was found to be in the linear range up to 20 µg, the highest concentration tested. Based on the enzyme concentration curve and stock concentration, 15 µg was selected for the assay. At this protein concentration, the S/N ratio was 30, with a good signal window ($CPM_{Pos.Ctrl}$-$CPM_{Blank}$=1650)

$K_m$ (Michaelis Menton constant) is a measure of the binding affinity of substrate to the enzyme. 17-α-hydroxy pregnenolone[21-3H] is a substrate for 17,20 lyase enzyme. $K_m$ for this substrate was determined by monitoring the tritiated acetic acid release as a function of substrate concentration. Concentration of 17-α-hydroxypregnenolone [21-3H] was varied from 0.03125 µM to 1 µM. For the $K_m$ determination, the data was fit to a hyperbolic equation (Graphpad Prism® software IV). The $K_m$ was estimated as 0.25 µM, close to the reported value. (Dmitry N. Grigoryev et al, *Analytical Biochemistry* (1999) 267, 319-330)

For routine screening, the assay was set up with 16 µg of enzyme in 50 µL reaction volume. 17α-hydroxy pregnenolone [21-3H] was added to a final concentration of 0.25 µM. NADPH is used at a final concentration of 4.2 mM. Total reaction volume was made up to 50 µL with 50 mM Phosphate buffer pH 7.5. The reaction mixture was incubated at room temperature for 90 minutes with gentle shaking. The reaction was stopped by the addition of 100 µL of buffer. 500 µL of 5% freshly prepared activated charcoal was added to the solution and mixed well by vortexing. The samples were centrifuged at 17568×g for 5 minutes. (14000 rpm). The supernatant was carefully transferred to fresh tube and 1.3 mL of scintillation fluid was added, mixed by vortexing.

The radioactivity was measured in a 1450 MicroBeta Tri-Lux™ scintillation counter from Wallac-Perkin Elmer®, USA. The measurements were carried out in 2.0 mL Eppendorf™ tubes. Each tube was counted for 1 minute. The amount of tritiated acetic acid released is proportional to the lyase activity. Percent lyase activity in presence of inhibitor was calculated using the formula given below.

$$\% \text{ Lyase activity} = \frac{CPM_{sample} - CPM_{blank}}{CPM_{Pos.\ Ctrl} - CPM_{Blank}} \times 100$$

Sample: Enzyme reaction in presence of inhibitor.
Positive control: Enzyme reaction without inhibitor but containing DMSO at 1% final concentration.
Blank—Contains all reagents except enzyme.

% Inhibition=100%-% Lyase activity

For IC$_{50}$ determination, the % inhibition was plotted as a function of inhibitor concentration. The data was fitted to sigmoidal equation using Graphpad Prism® software IV to generate IC$_{50}$ values.

Dose-response studies by standard compounds Abiraterone and Ketoconazole were carried out as part of assay optimization.

For the Rat CYP17 Lyase Model:

The same procedure described above was used but using rat testes microsomes as the source and with a substrate concentration of 0.5 μM.

The results for the compounds tested from the Examples above using the assay above are listed in Table 1 below.

TABLE 1

| Example No. | Compounds | Lyase IC 50 nM Human/Rat |
|---|---|---|
| 1A | 1-(2-Chloropyridin-4-yl)-3-(4-cyclopropylpyridin-3-yl)imidazolidin-2-one | 8/2.7 |
| 2A | 1-(4-Cyclopropylpyridin-3-yl)-3-(2-(trifluoromethyl) pyridin-4-yl)imidazolidin-2-one | 9/1.1 |
| 3A | 1-(4-Cyclopropylpyridin-3-yl)-3-(naphthalen-2-yl) imidazolidin-2-one | 26/NA |
| 4A | 1-(Benzo[b]thiophen-5-yl)-3-(4-cyclopropylpyridin-3-yl)imidazolidin-2-one | 13/NA |
| 5A | 1-(4-Cyclopropylpyridin-3-yl)-3-(3-(trifluoromethyl) phenyl)imidazolidin-2-one | 6/NA |
| 6A | 1-(Benzo[b]thiophen-2-yl)-3-(4-cyclopropylpyridin-3-yl)imidazolidin-2-one | 13/NA |
| 7A | 1-(6-Chloro-2-methylpyrimidin-4-yl)-3-(4-cyclopropylpyridin-3-yl)imidazolidin-2-one | 41/NA |
| 8A | 1-(4-Cyclopropylpyridin-3-yl)-3-(4-(trifluoromethyl) pyridin-2-yl)imidazolidin-2-one | 22/NA |
| 9A | 1-(4-Cyclopropylpyridin-3-yl)-3-(2-methoxypyridin-4-yl)imidazolidin-2-one | 42/4.6 |
| 10A | 1-(6-Chloropyrimidin-4-yl)-3-(4-cyclopropylpyridin-3-yl)imidazolidin-2-one | 121/NA |
| 11A | 1-(4-Cyclopropylpyridin-3-yl)-3-(4-(trifluoromethyl) pyrimidin-2-yl) imidazolidin-2-one | 58%@10 mM/NA |
| 12A | 1-(4-Cyclopropylpyridin-3-yl)-3-(2-(trifluoromethyl) pyrimidin-4-yl) imidazolidin-2-one | 99/NA |
| 13A | 1-(4-Cyclopropylpyridin-3-yl)-3-(3-(trifluoromethyl) benzo[b]thiophen-5-yl) imidazolidin-2-one | 11/NA |
| 14A | 1-(4-Cyclopropylpyridin-3-yl)-3-(2-fluorobenzo[b]thiophen-5-yl) imidazolidin-2-one | 26/NA |
| 15A | 1-(4-Cyclopropylpyridin-3-yl)-3-(3-methylbenzo[b]thiophen-5-yl) imidazolidin-2-one | 6.7/NA |
| 16A | 1-(Benzo[b]thiophen-6-yl)-3-(4-cyclopropylpyridin-3-yl)imidazolidin-2-one | 7/NA |
| 17A | 1-(4-Cyclopropylpyridin-3-yl)-3-(2,2-difluorobenzo[d][1,3]dioxol-5-yl)imidazolidin-2-one | 58/NA |
| 18A | 1-(4-Cyclopropylpyridin-3-yl)-3-(3-methylbenzo[b]thiophen-6-yl)imidazolidin-2-one | 76/NA |
| 19A | 1-(4-Cyclopropylpyridin-3-yl)-3-(3-methylbenzofuran-5-yl)imidazolidin-2-one | 2.7/NA |
| 20A | 1-(2-Chlorobenzo[b]thiophen-5-yl)-3-(4-cyclopropylpyridin-3-yl)imidazolidin-2-one | 106/NA |
| 21A | 1-(4-Cyclopropylpyridin-3-yl)-3-(2,3-dihydro-1H-inden-5-yl)imidazolidin-2-one | 17/NA |
| 22A | 1-(4-Cyclopropylpyridin-3-yl)-3-(5-fluorobenzo[b]thiophen-2-yl)imidazolidin-2-one | 7/NA |
| 23A | 1-(4-Cyclopropylpyridin-3-yl)-3-(3-(trifluoromethyl) benzo[b]thiophen-6-yl)imidazolidin-2-one | 1213/NA |
| 24A | 1-(4-Cyclopropyl-pyridin-3-yl)-3-(2-fluoro-3-methyl-benzo[b]thiophen-5-yl)-imidazolidin-2-one | 19/NA |
| 25A | 1-(4-Cyclopropyl-pyridin-3-yl)-3-(2-fluoro-benzo(b)thiophene-6-yl)-imidazolidin-2-one | 30/NA |
| 26A | 1-(4-Cyclopropyl-pyridin-3-yl)-3-(4-fluoro-benzo[b]thiophen-6-yl)-imidazolidin-2-one | 6/NA |
| 27A | 1-(4-Cyclopropyl-pyridin-3-yl)-3-(5-fluoro-benzo[b]thiophen-6-yl)-imidazolidin-2-one | 461/NA |
| 28A | 1-(4-Cyclopropylpyridin-3-yl)-3-(6-fluorobenzo[b]thiophen-5-yl) imidazolidin-2-one | 548/NA |
| 29A | 1-(4-Cyclopropylpyridin-3-yl)-3-(5-fluoro-3-methylbenzo[b]thiophen-6-yl)imidazolidin-2-one | 65%@10 mM/NA |
| 30A-I | (1R,5S)-2-(2-Chloropyridin-4-yl)-4-(4-cyclopropylpyridin-3-yl)-2,4-diazabicyclo[3.1.0]hexan-3-one (Enantiomer I) | 161/NA |
| 30A-II | (1S,5R)-2-(2-Chloropyridin-4-yl)-4-(4-cyclopropylpyridin-3-yl)-2,4-diazabicyclo[3.1.0]hexan-3-one (Enantiomer II) | 6/NA |
| 31A-I | (1S,5R)-2-(4-Cyclopropylpyridin-3-yl)-4-(2-methoxypyridin-4-yl)-2,4-diazabicyclo[3.1.0]hexan-3-one (Enantiomer I) | 169/NA |
| 31A-II | (1R,5S)-2-(4-Cyclopropylpyridin-3-yl)-4-(2-methoxypyridin-4-yl)-2,4-diazabicyclo[3.1.0]hexan-3-one (Enantiomer II) | 12/NA |
| 32A-I | (1S,5R)-2-(4-Cyclopropylpyridin-3-yl)-4-(2-(trifluoromethyl)pyridin-4-yl)-2,4-diazabicyclo[3.1.0]hexan-3-one (Enantiomer I) | 184/NA |
| 32A-II | (1R,5S)-2-(4-Cyclopropylpyridin-3-yl)-4-(2-(trifluoromethyl)pyridin-4-yl)-2,4-diazabicyclo[3.1.0]hexan-3-one (Enantiomer II) | 6.9/3 |
| 33A | 1-(2-Chloro-pyridin-4-yl)-3-[4-(1-hydroxy-cyclobutyl)-pyridin-3-yl]-imidazolidin-2-one | 45/NA |
| 34A | 1-(2-Chloropyridin-4-yl)-3-(4-cyclopentyl-pyridin-3-yl)-imidazolidin-2-one | 13/NA |
| 35A | 1-(2-Chloropyridin-4-yl)-3-[4-(1-hydroxy cyclopentyl)-pyridin-3-yl]-imidazolidin-2-one | 341/NA |
| 36A | 1-[4-(1-Hydroxy-cyclopropyl)-pyridin-3-yl]-3-(3-trifluoromethyl-phenyl)-imidazolidin-2-one | 27/NA |
| 37A | 1-(2-Chloro-6-(trifluoromethyl)-pyridin-4-yl)-3-(4-cyclopropyl-pyridin-3-yl)imidazolidin-2-one | 5/NA |
| 38A | 1-(4-Cyclopropylpyridin-3-yl)-3-(6-cyclopropylpyrimidin-4-yl) imidazolidin-2-one | 48/NA |
| 39A | 1-(4-Cyclopropylpyridin-3-yl)-3-(2-cyclopropylpyridin-4-yl) imidazolidin-2-one | 12/NA |
| 40A | 1-(4-Cyclopropylpyridin-3-yl)-3-(6-methoxypyrimidin-4-yl) imidazolidin-2-one | 84/NA |

TABLE 1-continued

| Example No. | Compounds | Lyase IC 50 nM Human/Rat |
|---|---|---|
| 41A | 1-(4-Cyclopropylpyridin-3-yl)-3-(6-methylpyrimidin-4-yl)imidazolidin-2-one | 70/NA |
| 42A | 1-(4-Cyclopropylpyridin-3-yl)-3-(5-fluoro-4-methylpyridin-2-yl)imidazolidin-2-one | 22/NA |
| 43A | 1-(4-Cyclopropylpyridin-3-yl)-3-(2-cyclopropylpyrimidin-4-yl)imidazolidin-2-one | 36/NA |
| 44A | 1-(4-Cyclopropylpyridin-3-yl)-3-(2-methylpyrimidin-4-yl)imidazolidin-2-one | 397/NA |
| 45A | 1-(6-Chloro-2-(trifluoromethyl)pyrimidin-4-yl)-3-(4-cyclopropylpyridin-3-yl)imidazolidin-2-one | 10/NA |
| 46A | 1-(4-Cyclopropylpyridin-3-yl)-3-(2,6-dichloropyridin-4-yl)imidazolidin-2-one | 1.9/NA |
| 47A | 1-(2-Chloro-6-cyclopropylpyridin-4-yl)-3-(4-cyclopropylpyridin-3-yl)imidazolidin-2-one | 5.2/NA |
| 48A | 1-(2-Cyclopropyl-6-(trifluoromethyl) pyridin-4-yl)-3-(4-cyclopropylpyridin-3-yl)imidazolidin-2-one | 4.75/NA |
| 49A | 1-(2,6-Bis(trifluoromethyl)pyridin-4-yl)-3-(4-cyclopropylpyridin-3-yl)imidazolidin-2-one | 6/NA |
| 50A | 1-(4-Cyclopropyl-2-hydroxypyridin-3-yl)-3-(2-(trifluoromethyl) pyridin-4-yl)imidazolidin-2-one | 51%@10 μM/NA |

Comparison of the methyl pyridine compounds (i.e., compounds of Formula I where, $R^6$ is methyl) described in PCT Publication No. WO 2010/149755 with the corresponding cyclopropyl derivatives (compounds of Formula I where, $R^6$ is cyclopropyl) described herein showed that replacement of methyl by cyclopropyl typically resulted in improvement in potency of inhibition of human CYP17 in biochemical and cell based assays as well as improved selectivity over CYP1A2. In addition, the cyclopropyl pyridine derivatives typically exhibited improved metabolic stability in activated microsomes that resulted in longer half lives and lowering of clearance of the compound in vivo.

The compounds of present invention in free form or in salt form, exhibit valuable pharmacological properties, e.g. inhibition of CYP17 lyase, e.g. as indicated in the in vitro tests provided above and are therefore useful for therapy mediated by such inhibition. For example, the compounds of the present invention are useful in the treatment of inflammation and cancer (in particular, prostate cancer) in a mammal (preferably, a human).

Thus, as a further embodiment, the present invention provides the use of a compound of the present invention in therapy. In a further embodiment, the therapy is selected from a disease mediated by the regulation of 17α-hydroxylase/$C_{17,20}$-lyase.

In another embodiment, the invention provides a method of treating a disease which is treated by the regulation of 17α-hydroxylase/$C_{17,20}$-lyase comprising administration of a therapeutically acceptable amount of a compound of the present invention. In a further embodiment, the disease is prostate cancer.

What is claimed is:

1. A method for treating prostate cancer comprising the step of administering a compound of Formula (I)

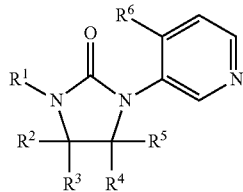

wherein $R^1$ is (i) phenyl optionally substituted with 1 to 3 substituents selected from halo, —CN, —OH, ($C_1$-$C_6$)alkyl, halo-substituted ($C_1$-$C_6$)alkyl, ($C_1$-$C_6$)alkoxy, —$NH_2$, —NH($C_1$-$C_4$)alkyl, —N(($C_1$-$C_4$)alkyl)$_2$, —NHC(O)—($C_1$-$C_4$)alkyl, —C(O)$NH_2$, —C(O)—NH($C_1$-$C_4$)alkyl, —C(O)—N(($C_1$-$C_4$)alkyl)$_2$, ($C_3$-$C_5$)cycloalkyl, or a 5- to 6-membered heterocycle, (ii) phenyl fused to an additional phenyl, a 5- to 6-membered heteroaryl, a 5- to 6-membered partially or fully saturated cycloalkyl, or a 5- to 6-membered partially or fully saturated heterocycle, where said fused phenyl is optionally substituted with 1 to 4 substituents each independently selected from halo, —CN, ($C_1$-$C_6$)alkyl, ($C_1$-$C_6$)alkoxy, hydroxy-substituted ($C_1$-$C_4$)alkyl, halo-substituted ($C_1$-$C_4$)alkyl, ($C_3$-$C_5$)cycloalkyl, oxo, —$NH_2$, —NH($C_1$-$C_4$)alkyl, —N(($C_1$-$C_4$)alkyl)$_2$, —NHC(O)—($C_1$-$C_4$)alkyl, or =N—OH, (iii) 5- to 6-membered heteroaryl optionally substituted with 1 to 3 substituents each independently selected from halo, —CN, —OH, ($C_1$-$C_6$)alkyl, halo-substituted ($C_1$-$C_6$)alkyl, ($C_1$-$C_6$)alkoxy, —$NH_2$, —NH($C_1$-$C_4$)alkyl, —N(($C_1$-$C_4$)alkyl)$_2$, —NHC(O)—($C_1$-$C_4$)alkyl, —C(O)$NH_2$, —C(O)—NH($C_1$-$C_4$)alkyl, —C(O)—N(($C_1$-$C_4$)alkyl)$_2$, ($C_3$-$C_5$)cycloalkyl, or a 5- to 6-membered heterocycle, or (iv) 5- to 6-membered heteroaryl fused to another 5- to 6-membered heteroaryl, phenyl, 5- to 6-membered partially or fully saturated cycloalkyl, or a 5- to 6-membered partially or fully saturated heterocycle, where said fused heteroaryl is optionally substituted with 1 to 4 substituents each independently selected from halo, —CN, ($C_1$-$C_6$)alkyl, ($C_1$-$C_6$)alkoxy, hydroxy-substituted ($C_1$-$C_4$)alkyl, halo-substituted ($C_1$-$C_4$)alkyl, ($C_3$-$C_5$)cycloalkyl, oxo, —$NH_2$, —NH($C_1$-$C_4$)alkyl, —N(($C_1$-$C_4$)alkyl)$_2$, —NHC(O)—($C_1$-$C_4$)alkyl, or =N—OH;

$R^2$ and $R^5$ are each independently $CH_3$ or H;

$R^3$ and $R^4$ are each independently $CH_3$ or H, or taken together with the carbon atoms to which they are attached form a cyclopropyl; and $R^6$ is ($C_3$-$C_5$)cycloalkyl, where the cycloalkyl is optionally substituted with hydroxy;

or a pharmaceutically acceptable salt thereof, to a subject in need of such treatment.

2. The method of claim 1, wherein the compound of Formula (I) has the structure of:

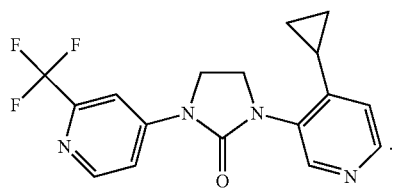 [SMILES: O=C1N(c2ccnc(C(F)(F)F)c2)CCN1c1cnccc1C1CC1]
* * * * *